United States Patent
Aben et al.

(10) Patent No.: US 12,190,504 B2
(45) Date of Patent: Jan. 7, 2025

(54) METHOD AND SYSTEM FOR CALCULATING MYOCARDIAL INFARCTION LIKELIHOOD BASED ON LESION WALL SHEAR STRESS DESCRIPTORS

(71) Applicant: Pie Medical Imaging B.V., Maastricht (NL)

(72) Inventors: Jean-Paul Michel Maria Aben, Limbricht (NL); Carlos Collet Bortone, Herne (BE); Dennis Koehn, Voerendaal (NL)

(73) Assignee: Pie Medical Imaging B.V., Maastricht (NL)

( * ) Notice: Subject to any disclaimer, the term of this patent is extended or adjusted under 35 U.S.C. 154(b) by 508 days.

(21) Appl. No.: 17/530,514

(22) Filed: Nov. 19, 2021

(65) Prior Publication Data

US 2022/0164950 A1     May 26, 2022

Related U.S. Application Data

(60) Provisional application No. 63/116,246, filed on Nov. 20, 2020.

(51) Int. Cl.
    *G06T 7/00*           (2017.01)
    *G06T 7/10*           (2017.01)
    (Continued)

(52) U.S. Cl.
    CPC .............. *G06T 7/0012* (2013.01); *G06T 7/10* (2017.01); *G06T 17/20* (2013.01); *G16H 30/20* (2018.01);
    (Continued)

(58) Field of Classification Search
CPC ......... G06T 7/0012; G06T 2207/30096; G06T 2207/30104; A61B 6/504
See application file for complete search history.

(56) References Cited

U.S. PATENT DOCUMENTS 7,155,046 B2    12/2006   Aben et al.
8,155,422 B2    4/2012    Zeigler et al.
                  (Continued)

OTHER PUBLICATIONS

De Nisco G, Tasso P, Calò K, Mazzi V, Gallo D, Condemi F, Farzaneh S, Avril S, Morbiducci U. Deciphering ascending thoracic aortic aneurysm hemodynamics in relation to biomechanical properties. Med Eng Phys. Aug. 2020;82:119-129. doi: 10.1016/j.medengphy.2020.07.003. Epub Jul. 12, 2020. PMID: 32709262. (Year: 2020).*

(Continued)

*Primary Examiner* — Bobbak Safaipour
*Assistant Examiner* — Michael Kim Maiden
(74) *Attorney, Agent, or Firm* — Dean D. Small; The Small Patent Law Group, LLC

(57) ABSTRACT

Method and systems are described that create a 3D reconstruction of a vessel of interest that represents a subset of a coronary tree that includes a lesion; calculate at least one of pressure parameters or anatomical parameters based at least in part on a portion of the 3D reconstruction that includes the lesion; calculate a wall shear stress (WSS) descriptor, based on the 3D reconstruction, for a segment of a surface of the vessel that includes the lesion, wherein the WSS descriptor includes information regarding an amount of variation in contraction or expansion applied at surface elements within the segment during at least a portion of a cardiac cycle; and calculate a myocardial infarction (MI) index based on the WSS descriptor and the at least one of the pressure or anatomical parameters, the MI index representing a likelihood that the lesion will result in an MI.

25 Claims, 40 Drawing Sheets

(51) Int. Cl.
    G06T 17/20    (2006.01)
    G16H 30/20    (2018.01)
    G16H 50/30    (2018.01)
(52) U.S. Cl.
    CPC ... G16H 50/30 (2018.01); *G06T 2207/10081*
        (2013.01); *G06T 2207/10116* (2013.01); *G06T
        2207/30096* (2013.01); *G06T 2207/30104*
            (2013.01); *G06T 2210/41* (2013.01)

(56) References Cited

U.S. PATENT DOCUMENTS

| | | | |
|---|---|---|---|
| 10,229,516 | B2 | 3/2019 | Aben et al. |
| 11,064,897 | B2* | 7/2021 | Tu .................. A61B 5/6852 |
| 11,083,377 | B2 | 8/2021 | Bouwman et al. |
| 11,341,645 | B2* | 5/2022 | Samady .................. G16H 30/40 |
| 11,694,339 | B2 | 7/2023 | Schormans et al. |
| 11,707,242 | B2 | 7/2023 | van Walsum et al. |
| 2017/0236326 | A1 | 8/2017 | Aben et al. |

OTHER PUBLICATIONS

Marchandise, Emilie & Crosetto, Paolo & Geuzaine, Christophe & Remacle, Jean-François & Sauvage, Emilie. (2011). Quality open source mesh generation for cardiovascular flow simulations. Modelling Physiological Flow. 5. 10. 1007/978-88-470-1935-5_13. (Year: 2011).*

Onuma Y, Girasis C, Aben JP, Sarno G, Piazza N, Lokkerbol C, Morel MA, Serruys PW. A novel dedicated 3-dimensional quantitative coronary analysis methodology for bifurcation lesions. EuroIntervention. Sep. 2011;7(5):629-35. doi: 10.4244/EIJV715A100. PMID: 21930468. (Year: 2011).*

Masdjedi et al., "Validation of 3-Dimensional Quantitative Coronary Angiography based software to calculate Fractional Flow Reserve: Fast Assessment of STenosis severity (FAST)-study", EuroIntervention : journal of EuroPCR in collaboration with the Working Group on Interventional Cardiology of the European Society of Cardiology. 2019.

Baka et al., "Oriented Gaussian mixture models for nonrigid 2D/3D coronary artery registration", IEEE Trans Med Imaging. May 2014;33(5):1023-34.

Chen et al, "Kinematic and Deformation Analysis of 4-D Coronary Arterial Trees Reconstructed From Cine Angiograms", IEEE Transactions on medical imaging, vol. 22, No. 6, Jun. 2003 pp. 710-721.

Ciusdel et al. in "Deep Neural Networks for ECG-free Cardiac Phase and End-Diastolic Frame Detection on Coronary Angiographies", Computerized Medical Imaging and Graphics Sep. 2020;84:101749.

Collet at al. in "Measurement of Hyperemic Pullback Pressure Gradients to Characterize Patterns of Coronary Atherosclerosis", J Am Coll Cardiology Oct. 8, 2019;74(14):1772-1784.

Dadvand et al., "An Object-oriented Environment for Developing Finite Element Codes for Multi-disciplinary Applications", Arch Computat Methods Eng 17, 2010, pp. 253-297.

De Nisco et al., "Deciphering ascending thoracic aortic aneurysm hemodynamics in relation to biomechanical properties", Med Eng Phys. 2020;82:119-29.

Dehkordi et al. in "Extraction of the best frames in coronary angiograms for diagnosis and analysis", J Med Signals Sens 2016;6:150-7 or by.

Dibildox et al., "3D/3D registration of coronary CTA and biplane XA reconstructions for improved image guidance", Med Phys. Sep. 2014;41(9).

Dodge et al., "Lumen Diameter of Normal Human Coronary Arteries Influence of Age, Sex, Anatomic Variation, and Left Ventricular Hypertrophy or Dilation" Circulation, vol. 86, No. 1, Jul. 1992 pp. 232-246.

Girasis C, et al., "Advanced three-dimensional quantitative coronary angiographic assessment of bifurcation lesions: methodology and phantom validation", EuroIntervention 2013; 8: 1451-1460.

Girasis et al. "Advances in two-dimensional quantitative coronary angiographic assessment of bifurcation lesions: improved small lumen diameter detection and automatic reference vessel diameter derivation", EuroIntervention Mar. 2012;7(11):1326-35.

Gould et al. in "Physiologic basis for assessing critical coronary stenosis. Instantaneous flow response and regional distribution during coronary hyperemia as measures of coronary flow reserve", Am J Cardiol. Jan. 1974;33(1):87-94 and.

Griffiths et al., "4D Quantitative Coronary Artery Motion Analysis: a Novel Method for Culprit Lesion Prediction", international Journal of Cardiovascular and Cerebrovascular Disease 6(1): 7-12, 201.

Grisan et al., "A novel method for the automatic evaluation of retinal vessel tortuosity", IEEE Transactions on Medical Imaging Mar. 2008;27(3):310-9.

Gronenschild E, et al. in "CAAS II: a Second Generation system for Off-Line and On-Line Quantitative Coronary Angiography", Cardiovascular Diagnosis 1994; 33: 61-75.

Kassab et al., "Scaling laws of vascular trees: of form and function", Am J Physiol Heart Circ Physiol 2006;290(2): H894-903.

Kim et al., "Patient-specific modeling of blood flow and pressure in human coronary arteries", Ann Biomed Eng 2010;38(10):3195-209.

Kirişsli et al. "Standardized evaluation framework for evaluating coronary artery stenosis detection, stenosis quantification and lumen segmentation algorithms in computed tomography angiography".

Kirkeeide et al. in "Assessment of coronary stenoses by myocardial perfusion imaging during pharmacologic coronary vasodilation. VII. Validation of coronary flow reserve as a single integrated functional measure of stenosis severity reflecting all its geometric dimensions", J Am Coll Cardiol. Jan. 1986;7(1):103-13.

Krams et al., "Evaluation of Endothelial Shear Stress and 3D Geometry as Factors Determining the Development of Atherosclerosis and Remodeling in Human Coronary Arteries in Vivo Combining 3D Reconstruction from Angiography and IVUS (ANGUS) with Computational Fluid Dynamics" Arteriosclerosis, Thrombosis, and Vascular Biology, vol. 17, No. 10, Oct. 1997, pp. 2061-2065.

Krijger et al., "Computation of steady three dimensional flow in a model of the basilar artery", J Biomechanics.. 1992;25:1451-1465.

Lesage et al, "Bayesian Maximal Paths for Coronary Artery Segmentation from 3D CT Angiograms", MICCAI 2009, Part 1, LNCS 5761, pp. 222-229.

Marchandise et al, "Quality open source mesh generation for cardiovascular flow simulations", Modeling of Physiological Flows, MS&A—Modeling, Simulation and Applications, vol. 5, 2012, pp. 395-414.

Morbiducci et al., "Wall shear stress topological skeleton independently predicts long-term restenosis after carotid bifurcation endarterectomy", Annals of Biomedical Engineering 2020; 1-14.

Murray et al., "The Physiological Principle of Minimum Work: I. The Vascular System and the Cost of Blood Volume", Proceedings of the National Academy of Sciences of the United States of America 1926;12(3):207-14).

Niu et al, "Radial Basis Function Mesh Deformation Based on Dynamic Control Points", Aerospace Science and Technology vol. 64, May 2017, pp. 122-132.

Onuma at at., "A novel dedicated 3-dimensional quantitative coronary analysis methodology for bifurcation lesions", EuroIntervention Sep. 2011;7(5):629-35.

Pan et al., "A Real-Time QRS Detection Algorithm", IEEE Transactions on Biomedical Engineering. BME-32 (3): 230-236.

Saltelli, "Making best use of model evaluations to compute sensitivity indices", Comput. Phys. Commun., vol. 145, No. 2, pp. 280-297, 2002 or by Saltelli et al., "Sensitivity analysis in practice. A guide to assessing scientific models", 2004, ISBN 0-470-87093-1.

Schoeberl in "NETGEN: an advancing front 2D/3D-mesh generator based on abstract rules", Computing and Visualization in Science 1:41-52, 1997.

Sochi "Non-Newtonian Rheology in Blood Circulation", 2013.

Van der Giessen et al., "The influence of boundary conditions on wall shear stress distribution in patients specific coronary trees", J Biomech 2011;44(6):1089-95.

(56) References Cited

OTHER PUBLICATIONS

Zhang et al. in "Automatic coronary blood flow computation: validation in quantitative flow ratio from coronary angiography", The International Journal of Cardiovascular Imaging vol. 35, pp. 587-595 (2019).
Zheng et al., "Sequential reconstruction of vessel skeletons from X-ray coronary angiographic sequences", Computerized Medical Imaging and Graphics 34 (2010) 333-345.

* cited by examiner

Grey zones contains discarded datapoint for healthy fit (3803)

METHOD AND SYSTEM FOR CALCULATING MYOCARDIAL INFARCTION LIKELIHOOD BASED ON LESION WALL SHEAR STRESS DESCRIPTORS

RELATED APPLICATIONS

The present application claims priority to U.S. Provisional Application No. 63/116,246, Titled "METHOD AND SYSTEM FOR CALCULATING MYOCARDIAL INFARCTION LIKELIHOOD BASED ON LESION WALL SHEAR STRESS DESCRIPTORS" which was filed on 20 Nov. 2020, the complete subject matter of which is expressly incorporated herein by reference in its entirety.

FIELD OF THE INVENTION

The present application relates to the technical field of medical imaging, particularly in percutaneous interventions that calculate a likelihood of myocardial infarctions.

STATE OF THE ART

Acute coronary syndrome (ACS) and sudden cardiac death can be the first manifestation of coronary artery disease and are the leading causes of death in the majority of the world's population. Although percutaneous coronary intervention (PCI) and pharmacologic therapies have improved the prognosis of patients suffering from coronary artery disease (CAD), myocardial infarction remains the deadliest complication of CAD and originates in most of the cases due to plaque rupture from mild obstructive coronary lesions. Intracoronary rheological quantities, such as wall shear stress (WSS) and pressure gradients, have been implicated as mechanisms in plaque destabilization. Moreover, vessel remodeling and atherosclerotic plaque phenotype play also a role predisposing plaque rupture. Finally, rupture occurs when the applied forces exceed plaque strength. Wall shear stress (WSS) describes hemodynamic stimuli acting at the blood-endothelium interface. Certain WSS patterns have been associated with development and vulnerable transformation of atherosclerotic lesions. Low WSS has been linked to atherosclerosis progression, whereas high WSS has been associated with plaque rupture and platelet activation. Likewise, pressure gradients across epicardial lesions have been recognized as an independent hemodynamic predictor of acute coronary syndromes. Both WSS and fractional flow reserve (FFR) can be accurately derived from invasive coronary angiography using computational fluid dynamics (CFD) simulations.

However, a need remains for improved methods and systems that more accurately identify lesions prone to rupture. A need remains for methods and systems that are able to reliably combine shear- and pressure-based descriptors and anatomical parameters to quantify plaque stress and to provide reliable predictive capability for plaque rupture and MI.

SUMMARY OF THE INVENTION

In accordance with new and unique aspects herein, a computer-implemented method is described that comprises: retrieving patient specific image data; creating a 3D reconstruction of a vessel of interest from the patient specific image data, wherein the vessel of interest represents a subset of a coronary tree that includes a lesion; calculating at least one of pressure parameters or anatomical parameters based at least in part on a portion of the 3D reconstruction that includes the lesion; calculating a wall shear stress (WSS) descriptor, based on the 3D reconstruction, for a segment of a surface of the vessel that includes the lesion, wherein the WSS descriptor includes information regarding an amount of variation in contraction or expansion applied at surface elements within the segment during at least a portion of a cardiac cycle; and calculating a myocardial infarction (MI) index based on the WSS descriptor and the at least one of the pressure or anatomical parameters, the MI index representing a likelihood that the lesion will result in an MI.

In accordance with aspects herein, the calculation of the WSS descriptor further comprises: calculating WSS vectors at corresponding surface elements within the segment; and calculating the WSS descriptors based on the WSS vectors. In accordance with aspects herein, the boundary conditions include inlet conditions that represent a set of velocity profiles over the at least the portion of the cardiac cycle at a proximal side of the 3D reconstruction. In accordance with aspects herein, a first velocity profile, from the set of velocity provides, represents a velocity profile across a cross-section of the vessel at a proximal side of the 3D reconstruction at a corresponding momentum in the cardiac cycle. In accordance with aspects herein, the WSS descriptor includes a topological shear variation index (TSVI), the TSVI representing the amount of variation in contraction or expansion applied at the surface elements, the method comprising calculating the TSVI based a divergence of the WSS vector. In accordance with aspects herein, the TSVI is based on instantaneous divergence at corresponding moments in the cardiac cycle and an average divergence over the cardiac cycle. In accordance with aspects herein, the negative and positive values for the divergence are indicative of contraction and expansion, respectively, at the corresponding surface elements. In accordance with aspects herein, for each of the surface elements, the method calculates a time-average WSS (TAWSS) by averaging a magnitude of the WSS vector over the cardiac cycle. In accordance with aspects herein, the calculating the MI index includes calculating a weighted sum of the WSS descriptor, the anatomical parameter and the pressure parameter.

In accordance with aspects herein, the method further comprises dividing the vessel into a legion segment, an upstream segment and a downstream segment, the lesion segment including a region of the vessel having a minimum lumen area (MLA) and delimited by proximal and distal boundaries, the upstream segment extending proximally from the proximal boundary by a proximal length that has a predetermined relation to a diameter of the vessel at the proximal boundary, the downstream segment extending distally from the distal boundary by a distal length that has a predetermined relation to a diameter of the vessel at the distal boundary. In accordance with aspects herein, the WSS represents a WSS vector includes an axial component and a circumferential component. In accordance with aspects herein, the MI index represents the likelihood that the lesion will rupture.

In accordance with aspects herein, the calculating the WSS descriptor further comprises: converting 3D reconstruction into a 3D volume mesh; utilizing computational fluid dynamics (CFD), to obtain velocities at volumetric elements throughout the 3D volume mesh, based on boundary conditions for the at least the portion of the cardiac cycle; calculating WSS vectors at the corresponding volumetric elements along the surface of the 3D volume mesh; and calculating the WSS descriptors based on the WSS vectors.

In accordance with new and unique aspects herein, the system is provided that comprises: memory to store program instructions; a processor that, when executing the program instructions, is configured to: retrieve patient specific image data; create a 3D reconstruction of a vessel of interest from the patient specific image data, wherein the vessel of interest represents a subset of a coronary tree that includes a lesion; calculate at least one of pressure parameters or anatomical parameters based at least in part on a portion of the 3D reconstruction that includes the lesion; calculate a wall shear stress (WSS) descriptor, based on the 3D reconstruction, for a segment of a surface of the vessel that includes the lesion, wherein the WSS descriptor includes information regarding an amount of variation in contraction or expansion applied at surface elements within the segment during at least a portion of a cardiac cycle; and calculate a myocardial infarction (MI) index based on the WSS descriptor and the at least one of the pressure or anatomical parameters, the MI index representing a likelihood that the lesion will result in an MI.

In accordance with aspects herein, the processor is further configured to calculate the WSS vectors at corresponding surface elements within the segment; and to calculate the WSS descriptors based on the WSS vectors. In accordance with aspects herein, the boundary conditions include inlet conditions that represent a set of velocity profiles over the at least the portion of the cardiac cycle at a proximal side of the 3D reconstruction. In accordance with aspects herein, a first velocity profile, from the set of velocity provides, represents a velocity profile across a cross-section of the vessel at a proximal side of the 3D reconstruction at a corresponding momentum in the cardiac cycle. In accordance with aspects herein, the WSS descriptor includes a topological shear variation index (TSVI), the TSVI representing the amount of variation in contraction or expansion applied at the surface elements, the processor is further comprised to calculate the TSVI based a divergence of the WSS vector. In accordance with aspects herein, the TSVI is based on instantaneous divergence at corresponding moments in the cardiac cycle and an average divergence over the cardiac cycle. In accordance with aspects herein, the negative and positive values for the divergence are indicative of contraction and expansion, respectively, at the corresponding surface elements.

In accordance with aspects herein, the processor is further configured to calculate, for each of the surface elements, a time-averaged WSS (TAWSS) by averaging a magnitude of the WSS vector over the cardiac cycle. In accordance with aspects herein, the processor is further configured to calculate the MI index by calculating a weighted sum of the WSS descriptor, the anatomical parameter and the pressure parameter. In accordance with aspects herein, the processor is further configured to: divide the vessel into a legion segment, an upstream segment and a downstream segment, the lesion segment including a region of the vessel having a minimum lumen area (MLA) and delimited by proximal and distal boundaries, the upstream segment extending proximally from the proximal boundary by a proximal length that has a predetermined relation to a diameter of the vessel at the proximal boundary, the downstream segment extending distally from the distal boundary by a distal length that has a predetermined relation to a diameter of the vessel at the distal boundary.

In accordance with aspects herein, the MI index represents the likelihood that the lesion will rupture. In accordance with aspects herein, the processor is further configured to calculate the WSS descriptor by: converting 3D reconstruction into a 3D volume mesh; utilizing computational fluid dynamics (CFD), to obtain velocities at volumetric elements throughout the 3D volume mesh, based on boundary conditions for the at least the portion of the cardiac cycle; calculating WSS vectors at the corresponding volumetric elements along the surface of the 3D volume mesh; and calculating the WSS descriptors based on the WSS vectors.

BRIEF DESCRIPTION OF THE DRAWINGS

The characteristics of the invention and the advantages derived therefrom will be more apparent from the following description of non-limiting embodiments, illustrated in the annexed drawings, in which.

DETAILED DESCRIPTION OF EMBODIMENTS

Figure 1:
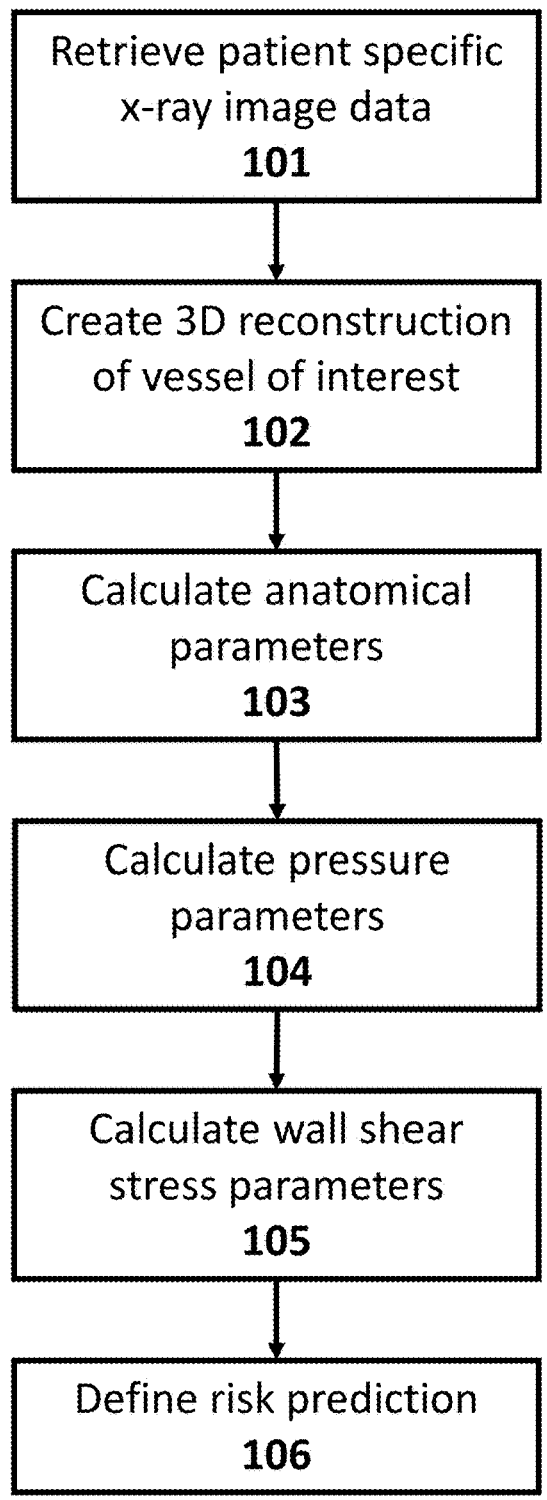
FIG. 1 shows a flow chart in accordance with an embodiment herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), at least one input device, and at least one output device. For example and without limitation, the programmable computers may be a personal computer, laptop, personal data assistant, and cellular telephone. Program code is applied to input data to perform the functions described herein and generate output information. The output information is applied to one or more output devices, in known fashion.

Each program is preferably implemented in a high-level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

The term image or image frame refers to a single image, and the term image sequence or image stream refers to a multiple images acquired over time using a stable perspective. The X-ray angiography image sequence may contain the contrast agent administration, and image frames which precedes the contrast agent administration will contain no contrast agent and thus no enhancement of the vasculature. The X-ray angiography image sequence may comprise multiple image frames covering one or more phases of the cardiac cycle. An angiographic projection or image projection or patient specific image data referrers to an image sequence acquired using a single perspective (in x-ray angiography using a specific rotation and angulation of the C-arm which does not change during the acquisition). Throughout this patent application, a cardiac cycle is specific to a patent and is defined as the period in which covers one heartbeat of the patient. The cardiac cycle can be defined as the period of time between successive R-tops within the electrocardiogram (ECG) signal of the patient. A phase refers to a moment (or period) of time within the cardiac cycle of the patient.

In accordance with new and unique aspects herein, embodiments are described to perform all analyses, that are derived from conventional angiography, using one or more software applications that are fully integrated with one another into a common software package. Prior to the present application, conventional systems utilized separate independent software packages to perform subsets of the operations, such as one software package to perform and manage three-dimensional reconstructions, a separate software package to manage mesh creation and yet a further separate software package to implement fluid dynamic simulations. In conventional approaches, each of the separate software packages further required support by separate engineering experts in the field of vascular biology.

In accordance with new and unique aspects herein, methods and systems are described that bring the calculation of WSS closer to the clinicians and may increase the feasibility of adopting WSS analysis in the routine clinical practice.

Overview

Myocardial infarction remains the deadliest complication of coronary artery disease (CAD) and originates in most cases due to plaque rupture from mild obstructive lesions. Intracoronary rheological quantities, such as wall shear stress (WSS) and pressure gradients, have been implicated as mechanisms in plaque destabilization. Moreover, vessel remodeling and atherosclerotic plaque phenotype play also a role predisposing plaque rupture. Finally, rupture occurs when the applied forces exceed plaque strength. WSS describes hemodynamic stimuli acting at the blood-endothelium interface. Certain WSS patterns have been associated with development and vulnerable transformation of atherosclerotic lesions. Low WSS has been linked to atherosclerosis progression, whereas high WSS has been associated with plaque rupture and platelet activation. Likewise, pressure gradients across epicardial lesions have been recognized as an independent hemodynamic predictor of acute coronary syndromes. Both WSS and fractional flow reserve (FFR) can be accurately derived from invasive coronary angiography using computational fluid dynamics (CFD) simulations.

Identification of lesions prone to rupture may personalize medical management in patients with CAD. The combination of shear- and pressure-based descriptors to quantify plaque stress may prove to have predictive capability for plaque rupture and MI. The present study aims evaluate the potential usefulness of a comprehensive hemodynamic assessment based on coronary angiography and CFD for the identification of lesions prone to MI.

In accordance with new and unique aspects herein, methods and systems are described that utilize computational fluid dynamics (CFD) and wall shear stress (WSS) descriptors to calculate a likelihood of a future potential myocardial infarction (MI). In accordance with new and unique aspects herein, a patient population of approximately 6885 patients with MI was analyzed. 80 of the patients had previous invasive angiograms suitable for three-dimensional coronary reconstruction. Quantitative coronary angiography (QCA), fractional flow reserve derived from angiography (vFFR) and wall shear stress (WSS) were analyzed in 76 future culprit lesions and in 102 nonculprit lesions (controls). Endothelium-blood flow interaction was assessed by two WSS descriptors, namely time-averaged wall shear stress (TAWSS) and topological shear variation index (TSVI). The patient mean age was 70.3±12.7 years, and 29% of the patients were female.

Patients presenting with acute MI admitted for invasive coronary catheterization were screened to identify those who (1) had a previous coronary angiography (here forth referred as baseline angiography) performed between 1 month and 5 years before the index event, (2) had the visually identifiable mild lesion (≤50% visual diameter stenosis) culprit for the future MI at the baseline angiography, and (3) had at least one additional non-culprit lesion (NCL) in at least one of the other two major epicardial vessels. Thus, each patient served as its own control. Patient exclusion criteria were post-coronary artery bypass graft (CABG) status, MI as result of in-stent restenosis or thrombosis, MI in absence of angiographically identifiable coronary lesions, ostial lesions or lesions involving a coronary bifurcation with a branching vessel diameter ≥2 mm. In case of multiple coronary angiographies before the acute event, the latest angiography was selected for analysis.

Future culprit lesions (FCL) and NCL were identified at the baseline angiography. Lesion adjudication (for both FCL and NCL) was performed blinded to the MI location information. Subsequently, three-dimensional reconstruction derived from coronary angiography of both FCL and NCL were generated for blood flow simulations.

In accordance with new and unique aspects herein, it was found that culprit lesions showed higher percent area stenosis (% AS), delta lesion vFFR, and TAWSS and TSVI as compared to non-culprit lesions (p<0.05 for all). It was also found that TSVI was superior to TAWSS in predicting MI (AUC$_{TSVI}$=0.75, 95% CI 0.69-0.81 vs. AUC$_{TAWSS}$=0.61, 95% CI 0.55-0.67, p<0.001). The addition of TSVI unexpectedly increased the predictive capacity by a significant amount, and TSVI unexpectedly increased the reclassification ability also by a significant amount (net reclassification improvement=1.04, p<0.001, relative integrated discrimination improvement=0.21, p<0.001) compared to a model based on % AS and delta lesion vFFR.

Based on the unexpected results derived herein, new and unique methods and systems have been derived to identify lesions culprit for future MI using QCA-based CFD. Embodiments utilize a weighted combination of luminal stenosis, pressure gradients and WSS descriptors to derive an MI index indicative of a likelihood or prediction of an occurrence of MI. An accuracy of the MI index to identify lesions prone to rupture was unexpectedly improved by a substantial amount when calculating the MI index in part based on the WSS-based descriptor that accounts for the variation in the contraction and expansion action of shear forces on the endothelium along the cardiac cycle.

As described herein, three-dimensional quantitative coronary angiography (3D-QCA) reconstructions were performed using two angiographic views at least 30 degrees apart as first step using the CAAS Workstation WSS software (Pie Medical Imaging, Maastricht, the Netherlands). Automated lumen contour detection was enabled, and manually corrected when needed. 3D coronary reconstruction included at least 20 mm proximally and 20 mm distally from the minimal lumen diameter (MLD). Using the 3D coronary reconstruction, CFD simulations were carried out using a finite element-based code (CAAS Workstation WSS prototype software, Pie Medical Imaging) to quantify WSS distribution along the cardiac cycle. Inflow boundary conditions were prescribed based on patient-specific mean flow rates. In detail, a generic Doppler velocity curve distinctive for the right and left coronary arteries was scaled by applying a diameter-based scaling law using the patient-specific lumen diameter, and was prescribed in terms of parabolic velocity profile at the inflow boundary. A reference pressure was imposed as outlet boundary condition. Vessel walls were assumed to be rigid and no-slip condition was applied at the wall boundary. Blood was assumed as a homogeneous, incompressible Newtonian fluid with a density of 1050 kg/m$^3$ and dynamic viscosity of 0.0035 Pa s.

Thirty coronary artery models were randomly selected and the analysis was repeated to assess the reproducibility of the CAAS Workstation WSS software.

The 3D-QCA and the angiography-derived fractional flow reserve (vFFR) were obtained using the CAAS Workstation vFFR software (Pie Medical Imaging) on the same angiographic projections selected for the WSS calculation. Anatomical descriptors included percentage area and diameter stenoses (% AS), minimal lumen area (MLA) and diameter, reference vessel diameter, lesion length and distance of MLA from the ostium. Distal vFFR, pressure gradients across the lesion, i.e. delta lesion vFFR (or lesion vFFR), and the absolute pressure drop in millimetres of mercury (mmHg) at the distal part of the vessel, i.e. distal pressure gradient, were extracted as described by Masdjedi et al., "*Validation of* 3-*Dimensional Quantitative Coronary Angiography based software to calculate Fractional Flow Reserve: Fast Assessment of STenosis severity (FAST)-study*", EuroIntervention: journal of EuroPCR in collaboration with the Working Group on Interventional Cardiology of the European Society of Cardiology. 2019.

The action of shear forces on the endothelium was quantified using the canonical WSS-based hemodynamic quantity time-averaged wall shear stress (TAWSS), obtained by averaging the local values of WSS magnitude along the cardiac cycle. The definition of TAWSS as well as an explanatory example of two possible flow regimes corresponding to low and high TAWSS, is presented herein. Additionally, the action exerted by shear forces on the endothelium was further characterized by identifying WSS contraction/expansion regions along the endothelial surface. Mathematically, endothelial surface areas experiencing contraction/expansion of the WSS vector field can be identified through the divergence of the WSS unit vector field (DIV$_{WSS}$). Negative/positive DIV$_{WSS}$ values identify WSS contraction/expansion regions. The quantity topological shear variation index (TSVI) was used as a measure of the variability of the local action of contraction/expansion exerted by the WSS along the cardiac cycle. Technically, the TSVI is defined as the root mean square deviation of the instantaneous divergence of the unit WSS vector field with respect to its average over the cardiac cycle:

$$TSVI = \left\{ \frac{1}{T} \int_0^T [DIV_{WSS} - \overline{DIV_{WSS}}]^2 dt \right\}^{1/2} \quad \text{(equation 1)}$$

where T is the cardiac cycle duration and the overbar denotes a time-average quantity. By definition, TAWSS are expressed in pascals whereas TSVI in $m^{-1}$. An explanatory example of two possible WSS vector field configurations along the cardiac cycle corresponding to low and high TSVI experienced by endothelial cells, is presented herein.

Each coronary vessel was divided in three segments: (1) lesion, defined as the segment including the minimal lumen area (MLA) and delimited proximal and distally by the intersection of the area function line with the interpolated reference line, (2) an upstream segment with a length of three times the diameter of the proximal boundary of the lesion, and (3) a downstream segment with a length of three times the diameter of the distal boundary of the lesion. TAWSS and TSVI are presented as averaged values at the lesion, upstream and downstream segments.

All statistical analyses were performed on a per-lesion basis to compare FCL and NCL lesion characteristics. Continuous variables with normal distribution are presented as mean±standard deviation (SD) and non-normally distributed variables as median (inter-quartile range, IQR). Categorical variables are presented as percentages. Chi-squared tests were used for comparing categorical variables, while Student's t (or Mann-Whitney tests as appropriate) for continuous ones. Multicollinearity was assessed by examining tolerance and the Variance Inflation Factor (VIF). Continuous hemodynamic parameters were converted to binary variables based on optimal cut-off values. The best cut-off values of angiographic, functional and WSS parameters were calculated using the receiving operator characteristics curve (ROC) analysis. The predictive capacity of WSS descriptors (i.e. TAWSS and TSVI) was assessed using C-statistics and compared using the DeLong method. The stronger WSS predictor for the prediction of MI was used to assess the incremental predictive value of WSS over % AS and pressure gradients. Three prediction models were constructed to determine the incremental discriminatory and reclassification ability of hemodynamic parameters in identifying culprit lesions associated with subsequent myocardial infarction. An anatomy-based model was based from percent area stenosis (% AS); subsequently, lesion vFFR was added (model 1=% AS and lesion vFFR) and, finally WSS was integrated first using TAWSS (i.e. model 2=% AS, lesion vFFR and TAWSS) and TSVI (model 3=% AS, lesion vFFR and TSVI). The discriminatory ability was assessed by c-statistics and the reclassification performance of each model was compared using category-free net reclassification index (NRI) and relative integrated discrimination improvement (IDI). WSS reproducibility was assessed with inter-class coefficient (ICC) analysis. All analyses were performed using R statistical software (R Foundation for Statistical Computing, Vienna, Austria).

From January 2008 to December 2019, 6885 patients underwent coronary catheterization for acute MI in the three participant centres, 775 (11.3%) patients had a previous angiography, among which 80 (vessel n=190; 2.37±0.47 vessel/patient) were included. Mean age of patients was 70.3±12.7 years and 28.7% were female. At the time of the myocardial infarction 76.3% were medicated with Aspirin and 90.0% with a statin. Sixty five percent of the patients presented with non-ST elevation myocardial infarction (NSTEMI) while 35.0% with a STEMI. Percutaneous coronary intervention was performed in 97.5% (78/80) of cases. The culprit lesion was located in 43.75% of cases in the LAD, 28.75% in the LCX and 27.5% in the RCA. Median time between baseline and index angiography was 25.9 (IQR 21.9-29.8) months. The vFFR analysis was feasible in 94.7% (n=76 patients, 180 vessels) whereas WSS analysis in 98.9% of vessels (n=80 patients, 188 vessels).

Angiographic characteristics of FCL (n=76) and NCL (n=104). % AS was significantly higher in the FCL group (63.58±12.49 vs. 56.01±12.38, p<0.001). Distal vFFR was lower in FCL compared to NFC (0.81±0.12 vs. 0.86±0.08, p=0.001), whereas lesion vFFR was higher in FCL compared to NFC (0.11±0.09 vs. 0.07±0.06, p<0.001) with a pressure drop of 17.59±11.86 mmHg in FCL vs. 12.72±7.9 mmHg in NFC (p=0.001). Both % AS and lesion vFFR exhibited moderate predictive capacity for MI (% AS AUC 0.61, 95% CI 0.54 to 0.68, p=0.001 and lesion vFFR AUC 0.58, 95% CI 0.52 to 0.64, p=0.002). The addition of lesion vFFR to % AS (model 1) improved the predictive performance for the occurrence of MI (model 1 AUC 0.64, 95% CI 0.57 to 0.72, p=0.051).

WSS-based descriptors (i.e. TAWSS and TSVI) were obtained in 188 vessels (FCL n=80; NCL=108). TAWSS and TSVI were significantly higher in the FCL group at the level of the lesion (4.58 Pa FCL vs. 3.38 Pa NFC, p=0.01 and 89.0 $m^{-1}$ FCL vs 49.12 $m^{-1}$ NFC, p<0.0001, respectively). The two WSS-based descriptors showed statistically significant predictive capacity for MI (TAWSS AUC 0.61, 95% CI 0.55 to 0.67, p<0.001 and TSVI AUC 0.75, 95% CI 0.69 to 0.81, p<0.001). The best cut-off values of TAWSS and TSVI were 5.01 Pa and 40.5 $m^{-1}$, respectively. TSVI showed significantly stronger predictive capacity compared to TAWSS (p<0.001). The reproducibility of the WSS analysis was excellent (TAWSS ICC 0.98, 95% CI 0.95 to 0.99 and TSVI ICC 0.96, 95% CI 0.91 to 0.98)).

Anatomical, pressure and WSS-based variables were available in 188 vessels (FCL=80 and NCL=108). Compared with the anatomical model (% AS), the inclusion of lesion vFFR (model 1) added discriminant capacity (% AS AUC 0.61, 95% CI 0.54 to 0.68 vs. model 1 AUC 0.64, 95% CI 0.57 to 0.72, p=0.05) without a significant improvement in the reclassification capacity (NRI: −0.13, p=0.39) for the identification of lesions culprit of subsequent MI. The addition of TAWSS demonstrated a non-significant increase in the predictive capacity for detecting FCL (model 1 AUC 0.64, 95% CI 0.57 to 0.72 vs. model 2 AUC 0.69, 95% CI 0.61 to 0.76; p=0.058) with a significant improvement in the reclassification capacity and with discriminatory improvement (NRI: 0.46, 95% CI 0.22 to 0.7, p<0.001 and relative DI: 0.05, 95% CI 0.01 to 0.08, p=0.006). The addition of TSVI to model 1 showed a significant increase in predictive capacity for MI (model 1 AUC 0.64, 95% CI 0.57 to 0.72 vs. model 3 AUC 0.79, 95% CI 0.73 to 0.86; p<0.001) with incremental reclassification and discriminatory capacity (NRI: 1.04, 95% CI 0.8 to 1.29, p<0.001; relative DI: 0.21, 95% CI 0.15 to 0.27, p<0.001).

Embodiments herein provide a comprehensive CFD evaluation based on invasive coronary angiography for the identification of lesions culprit of future MI. Culprit lesions have a higher area stenosis, higher pressure gradients, and higher TAWSS and TSVI than non-culprit lesions. A predictive model integrating anatomical stenosis severity, pressure gradients and WSS-based descriptors showed improved discriminatory and reclassification capacity in identifying lesions culprit of future MI compared with a model based on anatomy and pressure gradients. A QCA-based software application calculates WSS from standard angiographic images and has proved to be useful in identifying lesions at risk of rupture. The WSS-based descriptor, TSVI, showed a strong predictive capacity for future MI.

Plaque vulnerability and risk of plaque rupture have been the focus of extensive research in cardiovascular medicine over the last three decades. Early observations linked plaque vulnerability to lipid-rich atheromatous plaque and thin-cap fibroatheroma (TCFA). Studies based on intravascular imaging led to the identification of several markers of vulnerability such as TCFA, plaque burden ≥70% (PB) and MLA under 4 $mm^2$ as predictors of major adverse cardiovascular events. Near-infrared spectroscopy (NIRS) integrating lipid-core burden showed also to carry prognostic information for the occurrence of MI. Nevertheless, despite the association between plaque adverse characteristics and MI, the vast majority of these 'high-risk plaques' become quiescent over time, thus challenging the vulnerable plaque concept. Recently, using coronary computed tomography angiography (CCTA), a modality able to combine adverse plaque characteristic with rheological factor such as pressure drop and shear stress, the EMERALD study demonstrated the added value of the integration of hemodynamic features on the identifying of lesion prone to rupture. Therefore, an extended approach integrating luminal narrowing, plaque phenotype, adverse hemodynamic features (e.g., pressure drop and shear stress) and patients risk profile (e.g., diabetes mellitus, residual inflammatory risk) has been advocated. The present study combined both anatomical and hemodynamic descriptors aiming at understanding the contribution of forces exerted at the endothelium on the risk of plaque rupture and subsequent MI. Lesions were classified as culprit and non-culprit according to an overt clinical event, and NCL served as internal control, thus accounting for the intrinsic biological variability. In contrast to previous studies, the culprit criterion referred to a clinically relevant endpoint (i.e. MI), thus, minimizing biases related to softer endpoints such as anatomical plaque progression or target vessel revascularization. Furthermore, the occurrence of MI carries important prognostic implication.

Anatomical lesion severity (% AS) and the pressure drop across the lesions derived from blood flow simulations (lesion vFFR) had a significant albeit modest capacity in detecting future culprit. These two features showed improved predictive performance for the occurrence of MI. This study further investigated the action of fluid forces at the blood-endothelium interface. Shear forces transmitted by the flowing blood to the intraluminal surface of the endothelial cells play a central role in regulating local homeostasis, triggering pro-inflammatory plaque phenotypes associated with plaque destabilization and activation of platelets and Von Willebrand factor. Previous studies have shown that low TAWSS (<1.5 Pa) was associated with endothelial dysfunction and plaque progression, while high TAWSS (>4.71 Pa) in the proximal segments of the atherosclerotic plaque was predictive of plaque disruption and MI. More recently, a maximal TAWSS above 4.95 Pa over 3 mm vascular segment was found to independently predict major adverse cardiovascular events requiring revascularization. We also found a significantly association between TAWSS and FCL (4.58 Pa vs 3.38 Pa, p=0.01), with a moderate discriminative capacity (TAWSS AUC=0.61, 95% CI 0.55 to 0.67, p<0.001) and with a similar cut-off as previous reports (i.e. 5.01 Pa). In contrast with the EMERALD study and the FAME 2 WSS sub-analysis, our study cohort had a lower functional lesion severity as depicted by the proportion of hemodynamically significant lesions (20.5% vs. 49% vs. 100% in the EMERALD and FAME 2, respectively). This finding highlights the potential usefulness of the current approach in stratifying mild lesions and therefore tailoring preventive and therapeutic strategies.

Additionally, the link was investigated between WSS vector field skeleton features (i.e. TSVI) and the occurrence of MI. TSVI describes the contraction/expansion action exerted by fluid forces on the vessel wall, i.e. the push/pull action exerted by the WSS on the endothelium along the cardiac cycle. TSVI was previously linked to plaque progression by relating with the near-wall mass transport in carotid and coronary arteries. In the present study, TSVI outperformed the canonical TAWSS and, when integrated to the anatomic-functional model with % AS and lesion vFFR, resulted in a significantly improved reclassification and discriminatory capacity. Translating this into mechanistic implications, high temporal variation of WSS contraction/expansion action on the endothelium (quantified by TSVI), combined with area stenosis (% AS) and the hemodynamical strain on the plaque (lesion vFFR), may with time result in fibrous cap fragility, accelerated disease progression and plaque rupture with impact on clinical outcomes. This hypothesis warrants further investigation.

Embodiments herein provide comprehensive physiological evaluation of epicardial lesions which included (1) the pressure decay profile, (2) the instantaneous WSS vectors per degree of vessel circumference, (3) and TSVI, a novel descriptor, the WSS vector field skeleton of the lesion.

Anatomical lesion severity and pressure drop along the vessel showed modest capacity in identifying coronary lesions leading to MI. The extension of the functional evaluation to WSS-based descriptors—TAWSS and TSVI—derived from coronary angiography and CFD improved the predictive capacity for MI. TAWSS, the canonical WSS-based descriptor, was able to identify culprit lesions of a future MI, but with a modest predictive capacity. In contrast, TSVI, based on cardiac cycle- and topology-dependent heterogeneity of the shear stress variability, was strongly predictive for future MI.

System

Figure 2:
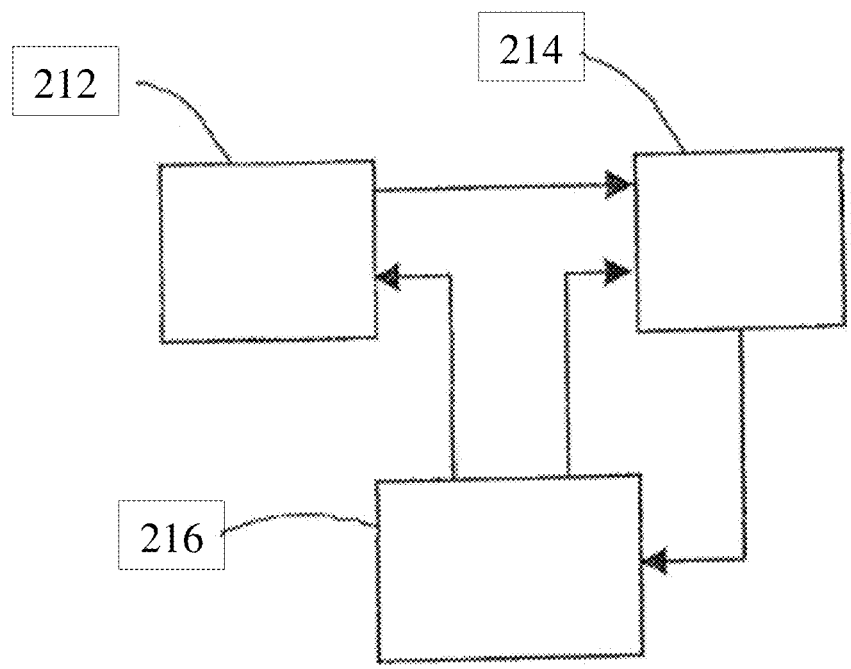
FIG. 2 shows a functional block diagram of an exemplary single plane angiographic system.
Figure 3:
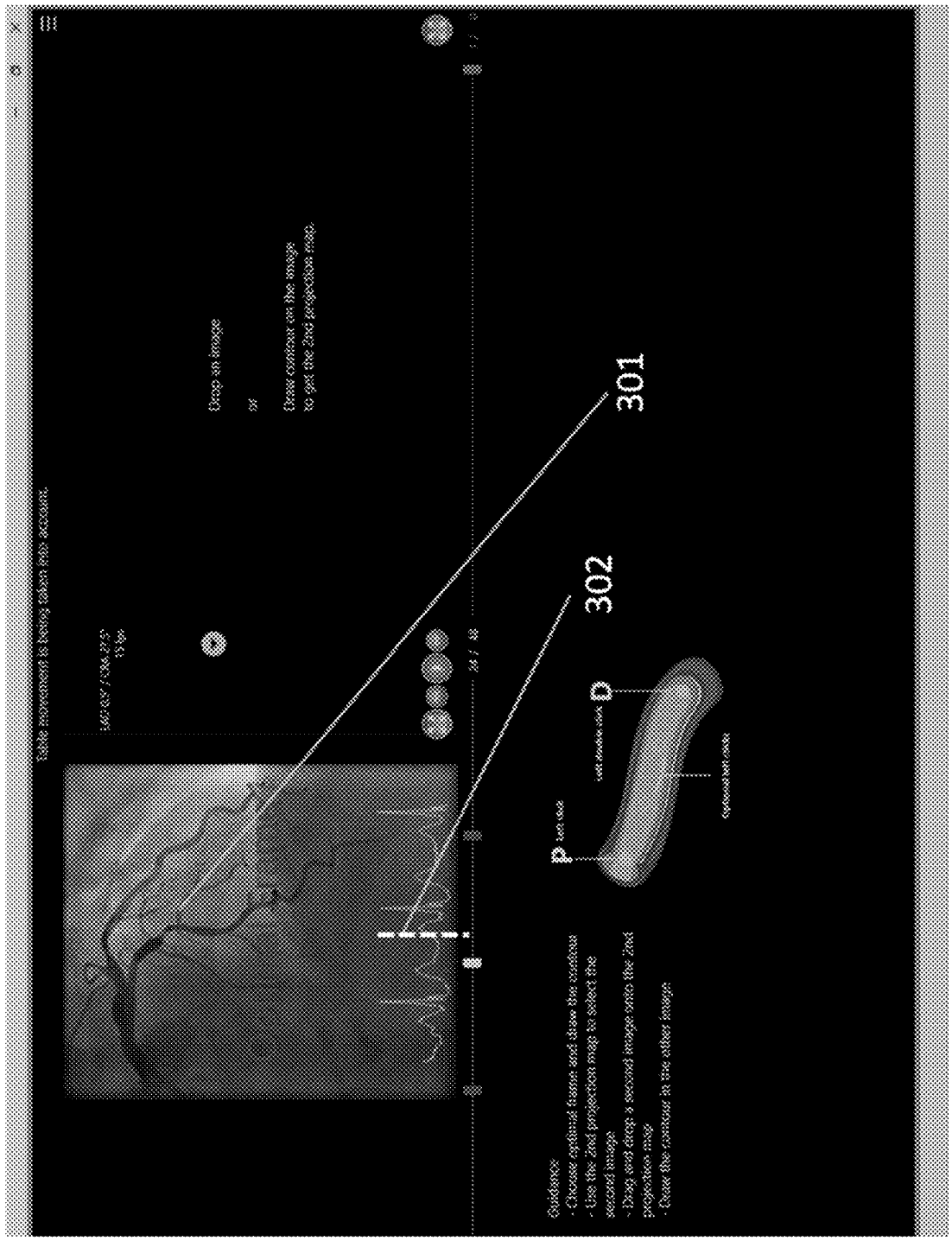
FIG. 3 shows an exemplary workflow screenshot to obtain the first image frame.

FIG. 2 is a functional block diagram of an exemplary single plane angiographic system, which includes an angiographic imaging apparatus 212 that operates under commands from user interface module 216 and will provide data to data processing module 214. The single plane angiographic imaging apparatus 212 captures a two-dimensional X-ray image sequence of the vessel organ of interest for example in the postero-anterior (PA) direction. The single plane angiographic imaging apparatus 212 typically includes an X-ray source and detector pair mounted on an arm of a supporting gantry. As can be seen in FIG. 1, the workflow comprises of number of steps. First patient specific image data is obtained as described in step 101 of FIG. 1. The patient specific image data is obtained during X-ray coronary angiography. This is a common step of a PCI intervention. Of the patient specific image data, as obtained during the X-ray coronary angiography, one image sequence is selected by the clinician in which the coronary vessel of interest is clearly visible as can be seen in step 301 of FIG. 3 and step 401 of FIG. 4. The system then automatically defines the select (e.g., optimal) frame within the image sequence to initiate the analysis as described in step 402 of FIG. 4. An image sequence comprises multiple frames covering one or more phases of the cardiac cycle. Furthermore, during an acquisition at a certain moment in time the contrast agent injection is started resulting in visual enhancement of the coronary vessels. The select frame is defined as a frame with the least coronary motion in which contract liquid is present. The select frame can for instance be determined using the ECG signal of the patient (if present), signal as available through the "headers" of the Digital Imaging and Communications in Medicine (DICOM) file, as shown as reference 302 in FIG. 3. Detection of specific features within the ECG signal, in our case the r-tops, can be performed as for example taught by Pan et al., "*A Real-Time QRS Detection Algorithm*", IEEE Transactions on Biomedical Engineering. BME-32 (3): 230-236. The select frame(s) can be defined as a percentage between two consecutive r-peaks. This percentage is typically 75%. Before the contrast is injected, the global frame image intensity will be different than after the contrast is injected within the sequence. Frames at the start of the sequence shows a relatively high mean pixel intensity, whereas frames after the injection of contrast shows a relative low mean pixel intensity. This due to the lower pixel values when the x-ray radiation is absorbed by the injected contrast liquid. This behavior can be taken into account by selection of the select frame; a frame with the least coronary motion in which contract liquid is present. In case the ECG signal is not present, the select frame can be identified based on machine learning techniques, as for instance taught by Dehkordi et al. in "*Extraction of the best frames in coronary angiograms for diagnosis and analysis*", J Med Signals Sens 2016; 6:150-7 or by Ciusdel et al. in "*Deep Neural Networks for ECG-free Cardiac Phase and End-Diastolic Frame Detection on Coronary Angiographies*", Computerized Medical Imaging and Graphics 2020 September; 84:101749.

Figure 4:
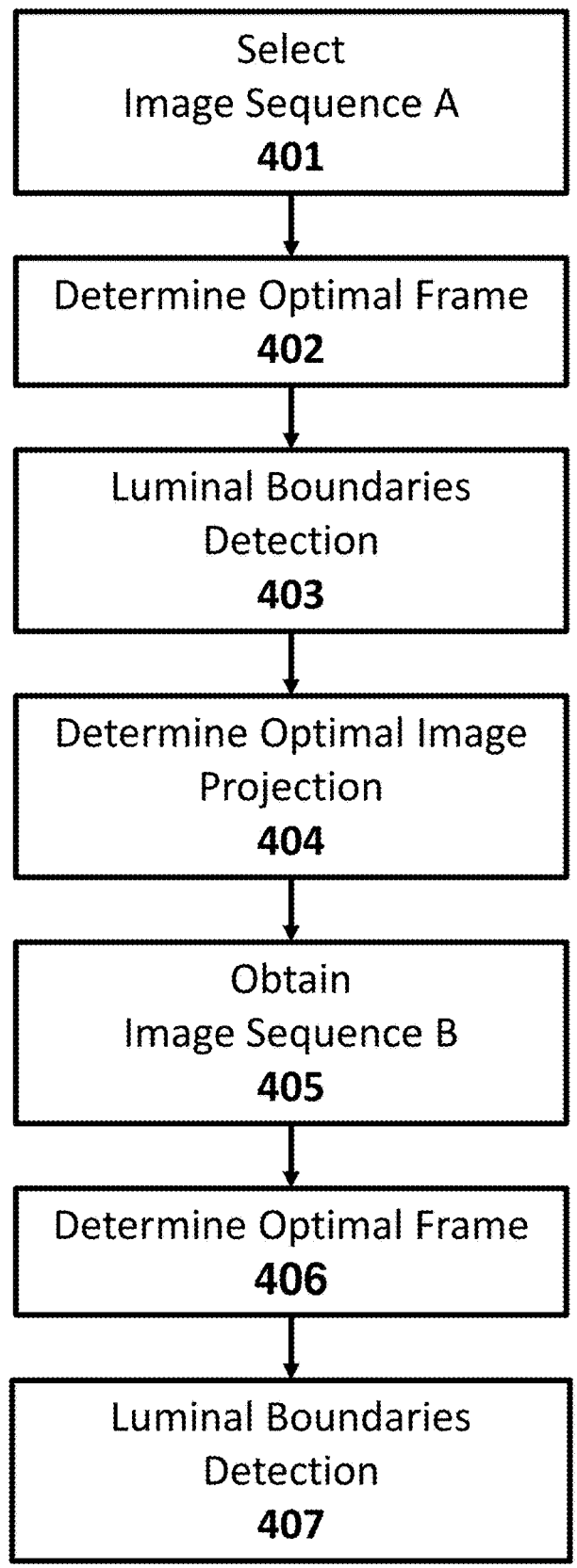
FIG. 4 shows a flow chart of a method for the contours required to perform a 3D reconstruction.
Figure 5:
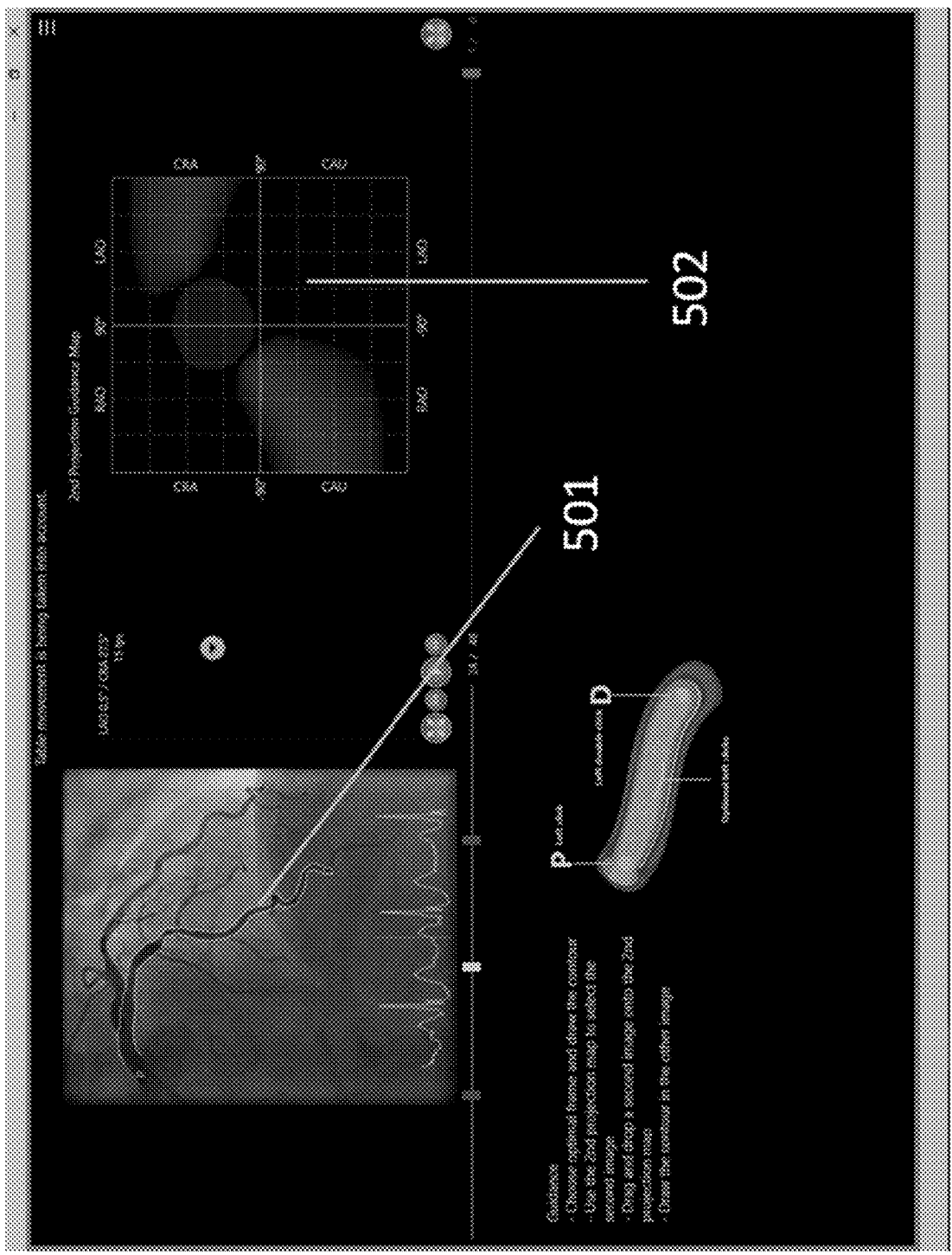
FIG. 5 shows an exemplary workflow screenshot with projection guidance.

In this select frame, the luminal boundaries of the coronary vessel of interest are detected as described by step 403 of FIG. 4. This detection can for instance be done semi-automatically where the clinician identifies a proximal and a distal end point within the vessel of interest, and in case of a vessel tree a distal end point in each vessel branch, and the processor then automatically detects the luminal boundaries as for instance described by Girasis et al. "*Advances in two-dimensional quantitative coronary angiographic assessment of bifurcation lesions: improved small lumen diameter detection and automatic reference vessel diameter derivation*", EuroIntervention 2012 March; 7(11):1326-35. The detected luminal boundaries can be seen in step 501 of FIG. 5. Optionally, the clinician can correct the detected luminal boundaries if needed.

One of the difficulties for a clinician during a standard PCI procedure or diagnostic x-ray angiography is selecting a second image projection that is desired (e.g., most optimal) in combination with the first image sequence to be used for generating an accurate 3D reconstruction, whereby an accurate 3D reconstruction is defined as a 3D reconstruction generated using the maximum amount of information concerning an object of interest. The two image sequences combined should contain as much information as possible regarding the object of interest. As the choice of this second image projection therefor largely determines the accuracy of the 3D reconstruction, it is important that it is chosen correctly. To simplify and facilitate this standard procedure step for the clinician, guidance is provided for the choice of the second image projection as for instance taught by US2017236326, "Method and Apparatus for User Guidance for the Choice of a Two-Dimensional Angiographic Projection". This guidance results in a color map, in which for each combination of rotation and angulation of the X-ray system a desired value (e.g., an optimal value) is shown using a corresponding color or grey value as can be seen in step 502 of FIG. 5. In the color map the whitest projection is the most optimal one, where the darkest projection is the less suitable one.

Using this color map the clinician can accurately and quickly determine which image projection is best suitable to obtain the second image sequence as described in step 404 of FIG. 4. This guidance for the clinician therefore can reduce standard procedure time.

Figure 6:
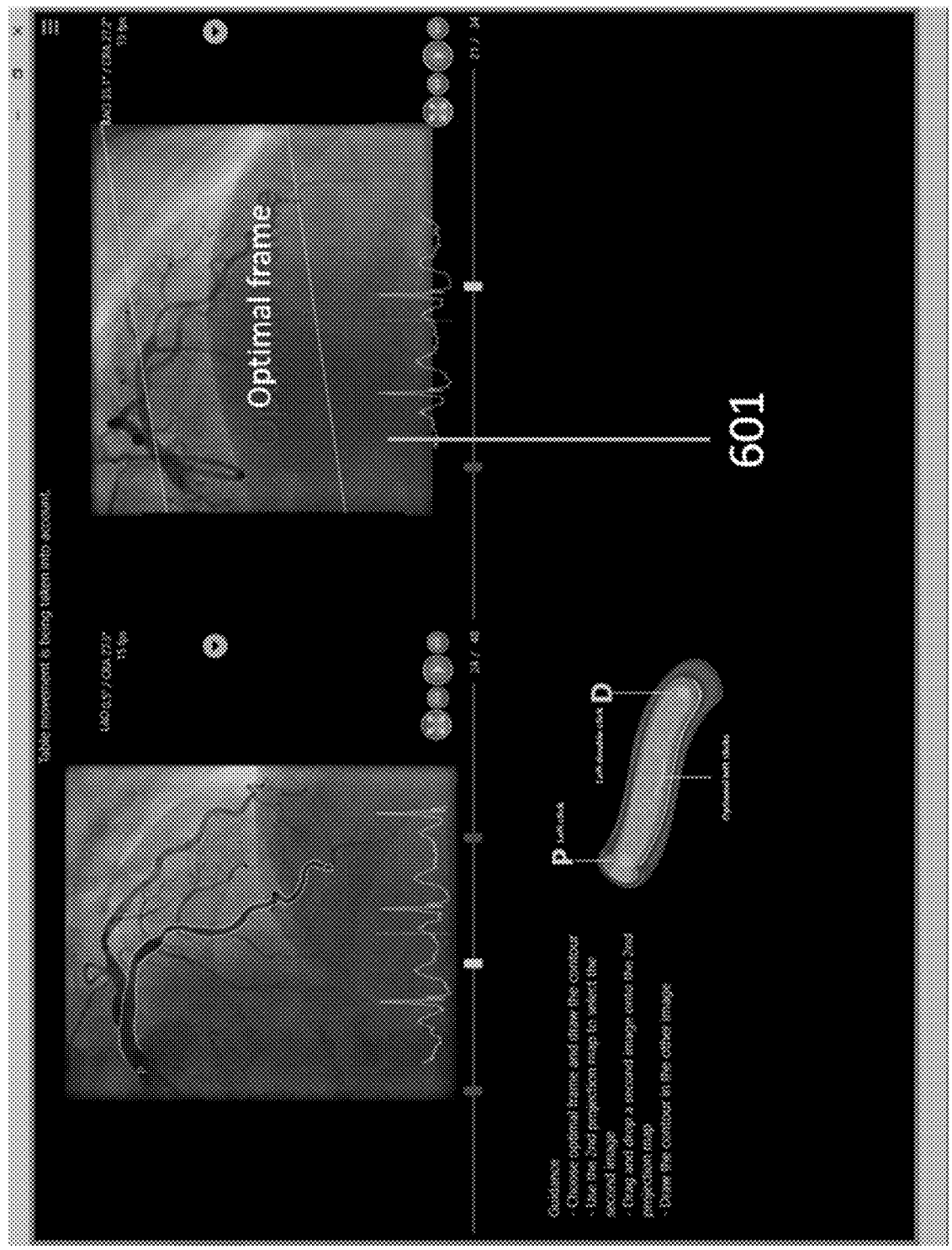
FIG. 6 shows an exemplary workflow screenshot with the obtained second image frame.

To obtain the image sequence corresponding to the optimal image projection as described in step 405 of FIG. 4, the clinician can manually rotate the arm of the imaging system into the position that corresponds to the chosen second projection, or to simplify the procedure even more for the clinician, the C-arm control module 1710 can automatically rotate the arm of the imaging system to the calculated optimal projection. The obtained second image sequence is then presented to the clinician as shown in step 601 of FIG. 6.

Just as the first image sequence, the obtained second image sequence comprises of multiple frames covering one or more phases of the cardiac cycle. When a clinician for instance uses a single plane imaging system, the obtained second image sequence can consist of different cardiac phases than the first image sequence. The 3D reconstruction becomes more accurate when frames of the two images sequences are used to generate the 3D reconstruction that were obtained at the same cardiac phase. The system therefore also provides for the second image sequence the select image frame for detecting the vessel of interest as described in step 406 of FIG. 4.

Another aspect that can occur during an intervention is table movement. It is not uncommon that in-between obtaining the first and second image sequence, the clinician has moved the patient table 1705 in order to for instance have a better overview during the procedure. However, table movement can also occur during image acquisition. When not taking table movement into account, inaccuracy can occur in the generation of the 3D reconstruction. Therefore X-ray system information, such as the distance between the X-ray tube and the X-ray detection panel, the distance between the X-ray tube and the C-arm isocenter, the position of the table rotation point relative to the C-arm isocenter, the 3D orientation of the C-arm and the adjustable table, both typically expressed in three angles, and finally the horizontal and vertical spacing of the pixels on the X-ray detector are taken into consideration during the 3D coronary reconstruction to compensate for table movement.

In the select frame of the second image sequence, the luminal boundaries are also detected (as shown in step 701 of FIG. 7 and described in step 407 of FIG. 4) using for instance the method as described for the first image frame.

Figure 7:
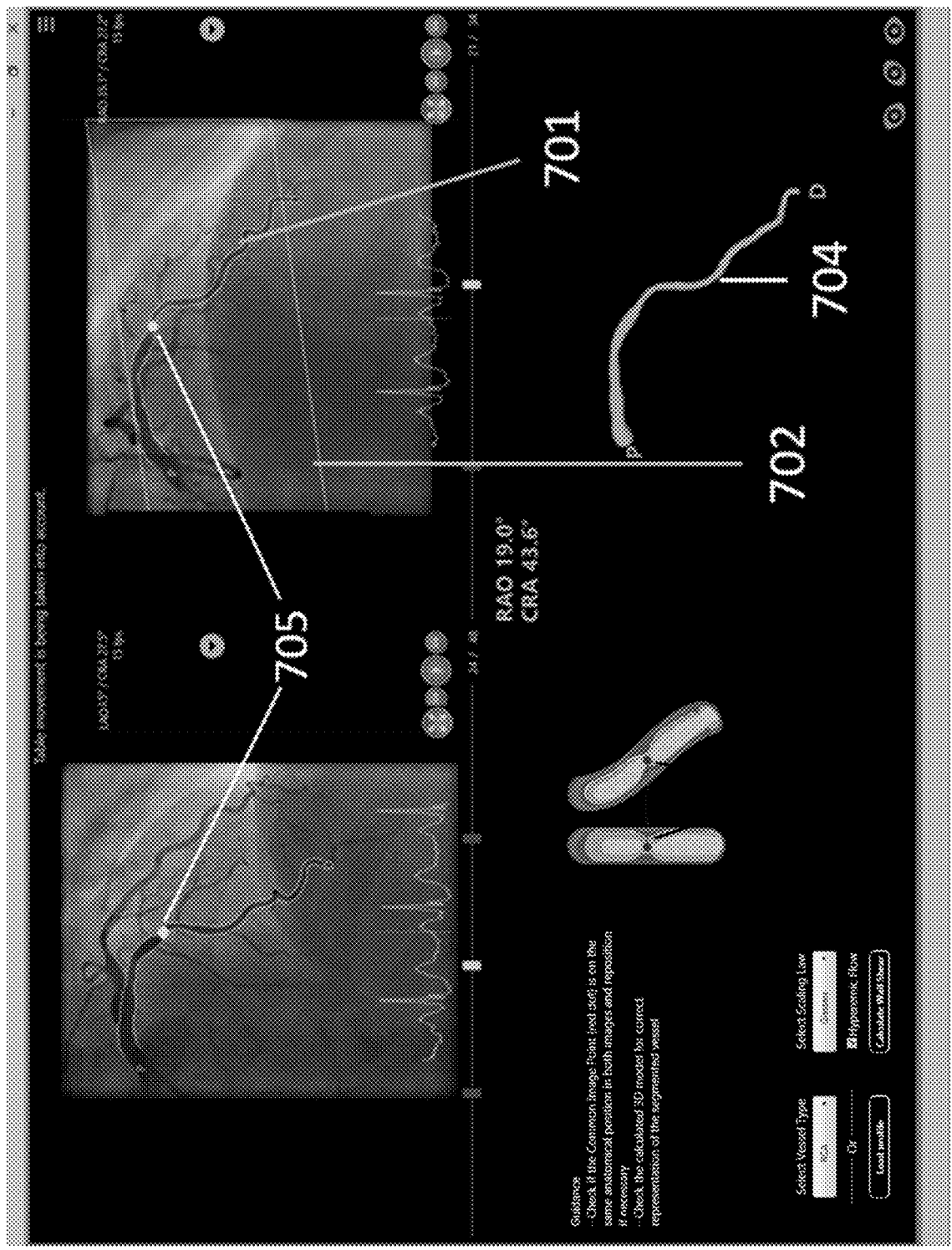
FIG. 7 shows an exemplary workflow screenshot with luminal boundaries and epi-polar lines.

To assist the clinician in indicating the vessel of interest in the second image frame so-called epi-polar lines as shown as reference 702 in FIG. 7 are shown on the second image frame. The epi-polar lines as shown in the second image frame represent the most proximal and distal position of the vessel as indicated in the first image frame following the viewing direction of the first image frame compared to the second image frame.

Additionally, a common image point (CIP) is automatically determined as can be seen in FIG. 7 as reference 705. The CIP represents a common landmark in both image frames, indicating the same anatomical location as illustrated in FIG. 7. This CIP is needed to correct for a possible offset of the isocenter of the image frame. An incorrect CIP results in an inaccurate 3D reconstruction. Optionally the clinician can reposition the CIP if necessary.

Additionally, multiple image sequences can be used with a different view (projection) of the vessel of interest by repeating step 405, 406 and 407 as input to create the 3D reconstruction of the vessel of interest.

After detection of the luminal boundaries in both image frames, as a result of the steps described by FIG. 4, the processor creates a 3D reconstruction of the vessel of interest represented by step 102 of FIG. 1. The metadata stored through the DICOM headers with the X-ray images should at least contain the following information: the distance between the X-ray tube and the X-ray detection panel, the distance between the X-ray tube and the C-arm isocenter, the position of the table rotation point relative to the C-arm isocenter, the 3D orientation of the C-arm and the adjustable table, both typically expressed in three angles, and finally the horizontal and vertical spacing of the pixels on the X-ray detector. Using this metadata, a complete geometric relation between the acquired images can be acquired that takes effects of repositioning the table into account.

While the derived geometric relations take the effects of table positioning into account, the actual position of the structure of interest may have changed due to other sources of motion. In the case of coronary arteries, these motion source included cardiac motion, respiratory motion, and patient motion relative to the table.

In order to compensate for the translation component of any remaining motion, a single point can be annotated (CIP as visible in FIG. 7 as reference 705), in all images that correspond the same physical point. Annotation of these points can either be done manually, or automatically. In the case where the structure of interest is a coronary artery, an example of an automatic annotation algorithm could be based on local diameter information extracted from the lumen boundary information. Using the annotated points to adjust the geometric relation between the images can be done as described in U.S. Pat. No. 7,155,046 entitled "Method of Determining Physical Parameters of Bodily Structures" issued to Aben et al.

Having a definition of the structure of interest within all images in addition to the geometric relation between all images, a 3D reconstruction of the structure of interest can then be reconstructed. A multitude of methods are described in existing art that are able to achieve this as for instance taught by Girasis et al., "*Advanced three-dimensional quantitative coronary angiographic assessment of bifurcation lesions: methodology and phantom validation*", EuroIntervention 2013; 8: 1451-1460 or as for instance as described by U.S. Pat. No. 8,155,422 entitled "Method, apparatus and computer program for quantitative bifurcation analysis in 3D using multiple 2D angiographic images". Most of these methods are based on the concepts of epipolar constraint and triangulation. If the relative position of two views are known together with the projection of a 3D point in one of the images, an epipolar line in the other image can be defined that must contain the projected position of the same point. This is called the epipolar constraint. Having found the projected position on the epipolar line in the other images, the three-dimensional position of the point can then be reconstructed through a process called triangulation, as known to those skilled in the art. If the structure of interest definitions consists of vessel centerlines, the resulting 3D reconstruction will be a 3D centerline. If lumen boundaries are included in the structure of interest definitions, information of the local vessel diameters can be incorporated into the 3D reconstructed model. In this case a surface model of the vessel lumen can be created.

Figure 8:
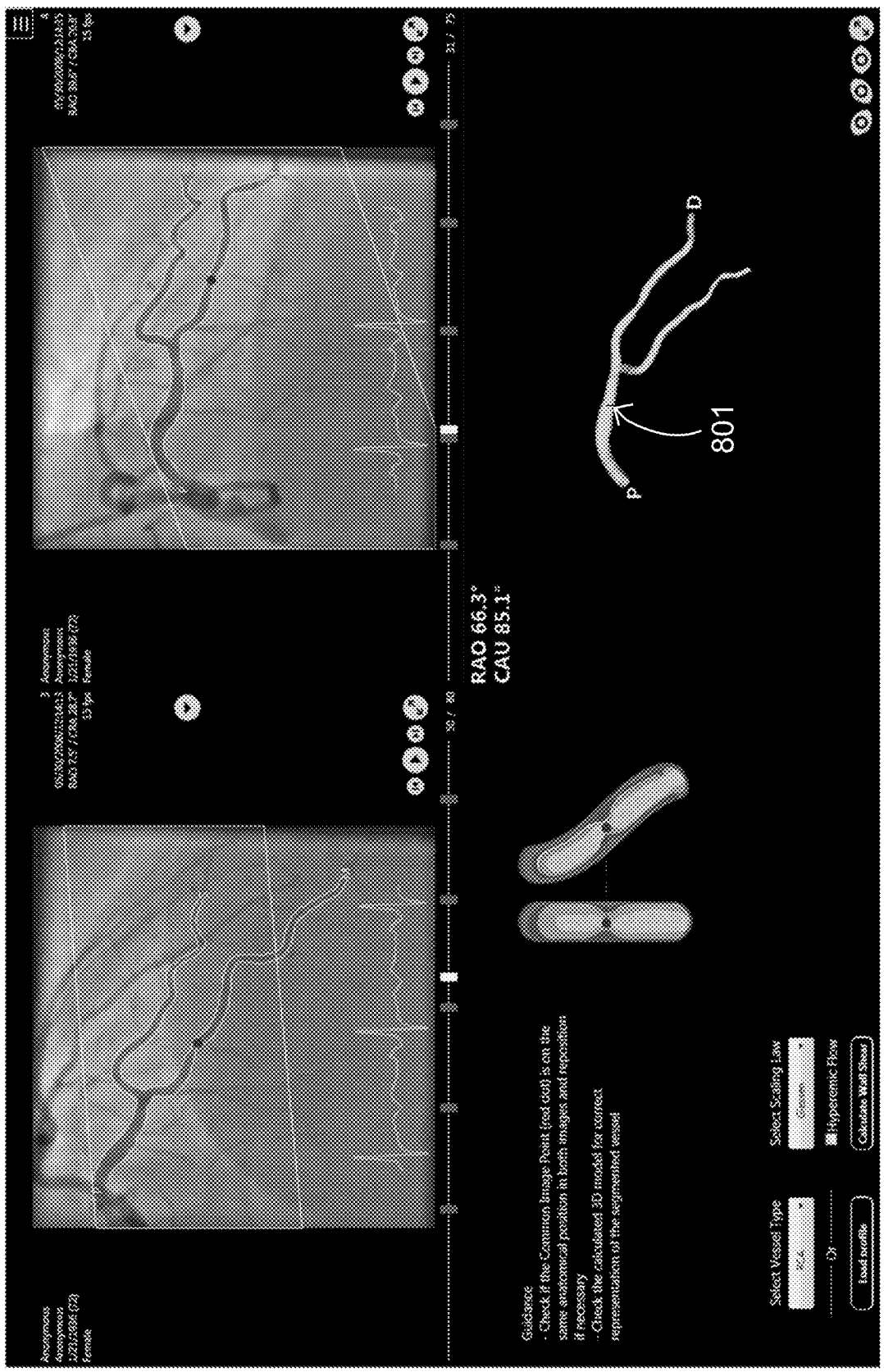
FIG. 8 shows an exemplary workflow screenshot for generating a 3D reconstruction for a coronary bifurcation.
Figure 30:
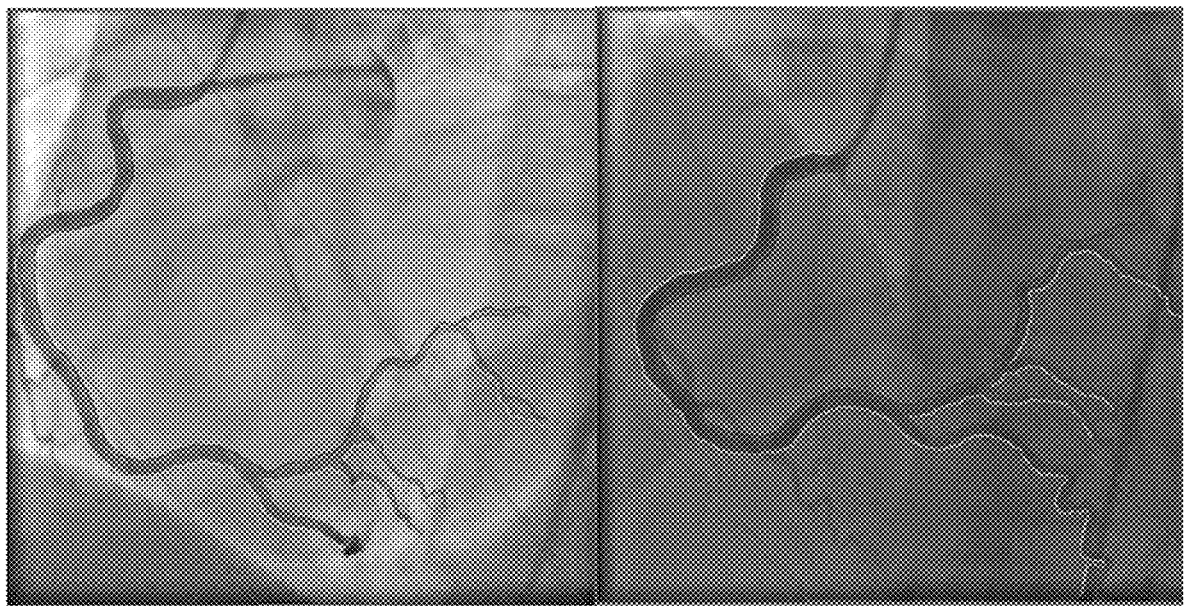
FIG. 30 provides some illustration of a 3D coronary tree reconstruction from multiple x-ray angiographic images.
Figure 30:
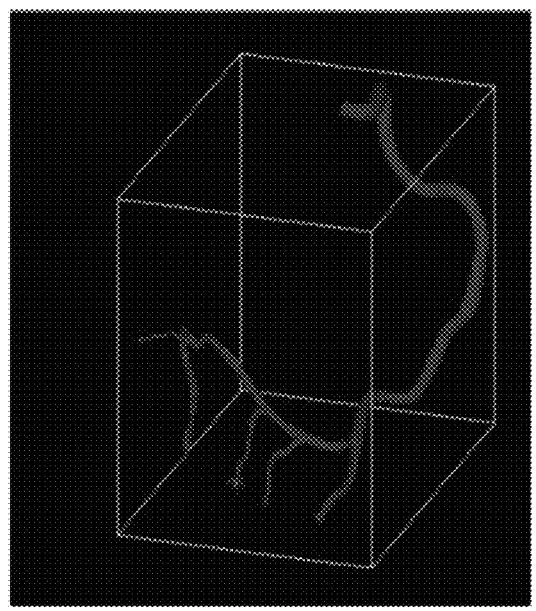

As described in step 102 of FIG. 1, the processor makes a patient specific 3D reconstruction of a subset of interest of the coronary tree using multiple two-dimensional images. An example of a 3D reconstruction is shown as reference 704 of FIG. 7 for a single vessel and 801 of FIG. 8 for a coronary bifurcation. The patient specific 3D reconstruction can also present a vessel tree as illustrated by FIG. 30.

Optionally, after generating the 3D reconstruction, the clinician can correct the 2D luminal boundaries if needed. If the luminal boundaries have been corrected, a new 3D reconstruction will be generated automatically.

Within an alternative embodiment, step 102 involves the creation of the 3D reconstruction along time (3D+t), and covering preferable at least one cardiac cycle. Current alternative embodiments describe two methods to create the 3D+t reconstructions. The first method creates the 3D+t reconstructions are created by processing the two X-ray angiographic image sequences that result from step 101. The 3D+t reconstruction for all frames within one cardiac cycle (after contrast injection) can for instance be created by the method as taught by Chen et al, "*Kinematic and Deformation Analysis of* 4-*D Coronary Arterial Trees Reconstructed From Cine Angiograms*", IEEE Transactions on medical imaging, Vol. 22, No. 6, June 2003 pp 710-721, or as taught by Zheng et al, "*Sequential reconstruction of vessel skeletons from X-ray coronary angiographic sequences*", Computerized Medical Imaging and Graphics 34 (2010) 333-345. In case the X-ray angiographic image sequences are acquired with a biplane system, the temporal resolution of the 3D+t roadmaps can be improved by using the delay between each acquired frame with respect to frontal and lateral imaging source.

The second method to create the 3D+t reconstructions uses an additional 3D model. This 3D model is obtained by using volumetric image data as generated from a 3D angiographic imaging modality, for instance computed tomography (CT), X-ray rotational angiography, 3D Ultrasound, or magnetic resonance imaging (MRI). The 3D model can be for example in the form of 3D centerlines, 3D surface contours representing the luminal surface of the vessels and/or the outer vessel surface, plaque, 3D masks, or a combination of these. The 3D centerlines can be created manually, for instance by indicating the vessel centerlines within the 3D volumetric image data, or automatically as taught for instance by Lesage et al, "*Bayesian Maximal Paths for Coronary Artery Segmentation from* 3*D CT Angiograms*", MICCAI 2009, Part 1, LNCS 5761, pp 222-229. The coronary lumen, arterial wall and detection of coronary plaque from CT angiographic image data can be for (semi) automatically detected as for instance taught by Kirişli et al. "*Standardized evaluation framework for evaluating coronary artery stenosis detection, stenosis quantification and lumen segmentation algorithms in computed tomography angiography*", Medical Image Analysis, vol. 17, no. 8, pp. 859-876, 2013, a methods are described to detect the coronary lumen, arterial wall and detection of coronary plaque from CT angiographic image data.

To create the 3D+t reconstructions by using an additional 3D as obtained from a 3D volumetric imaging modality, the 3D model is combined with the 3D reconstruction based on the x-ray angiographic data as a result of step 101. This can be achieved as for instance by the methodology described in U.S. Pat. No. 10,229,516 "*Method and Apparatus to Improve a* 3*D+Time Reconstruction*", which describes a method for making a three-dimensional surface reconstruction over time of an object from two or more bi-dimensional x-ray images of the object. Alternatively, the 3D+t reconstructions can be created as for instance taught by Dibildox et al., "*3D 3D registration of coronary CTA and biplane XA reconstructions for improved image guidance*", Med Phys. 2014 September; 41(9), or as taught by Baka et al., "*Oriented Gaussian mixture models for nonrigid 2D/3D coronary artery registration*", IEEE Trans Med Imaging. 2014 May; 33(5):1023-34.

Figure 9:
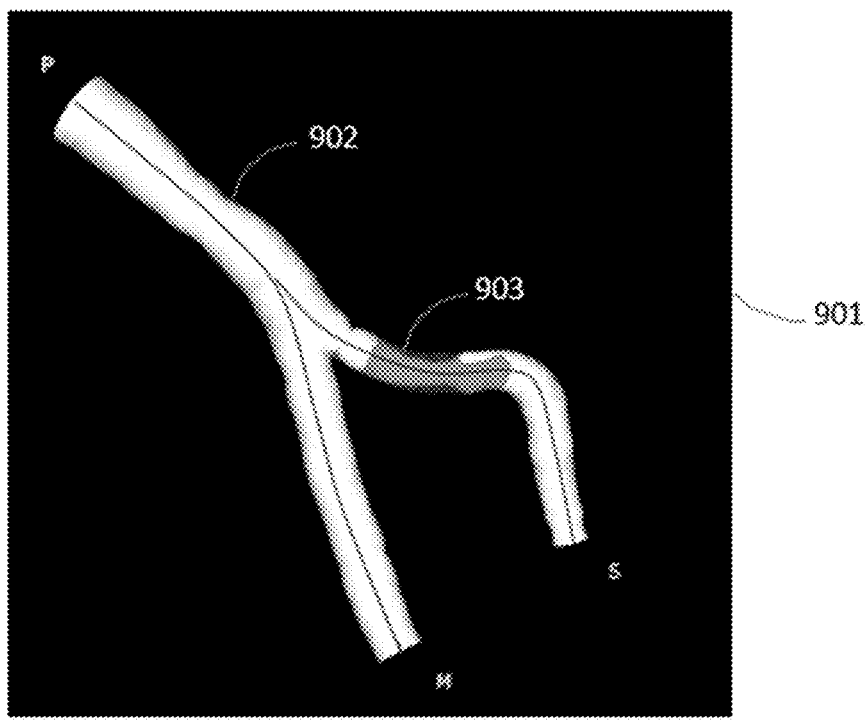
FIG. 9 shows an example of anatomical parameters extracted from a 3D reconstruction.
Figure 9:
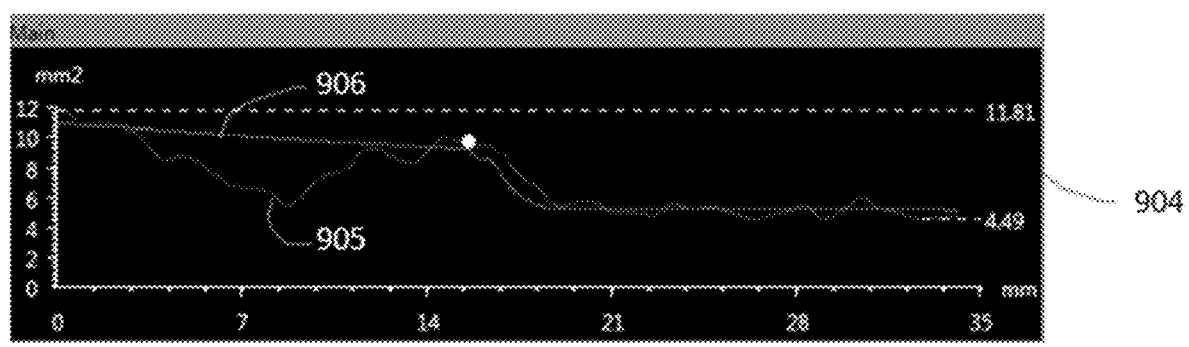
Figure 9:
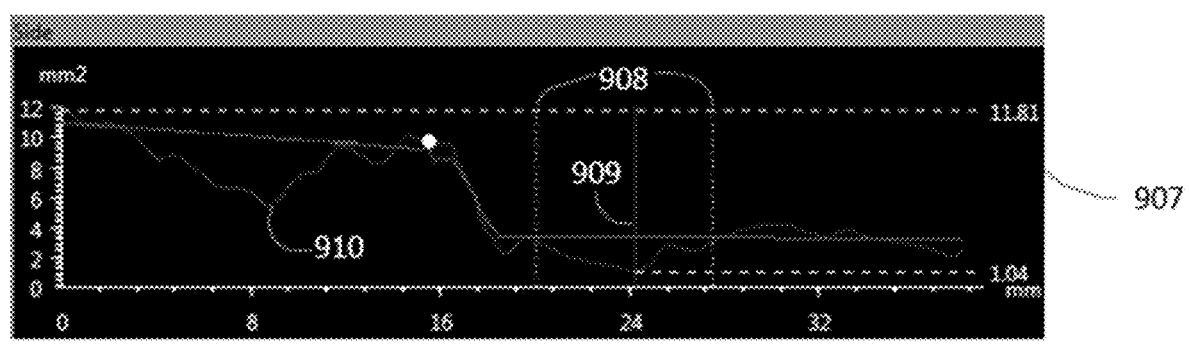

From the 3D reconstruction, anatomical parameters such as 3D geometric information can be extracted as described in step 103 of FIG. 1. This 3D geometric information can for example be the cross-sectional area and length of the vessel of interest along the centerline of the 3D reconstructed vessel of interest as shown by 902 of FIG. 9. Within FIG. 9, an example of a 3D coronary reconstruction, as a result of step 103, is provided by picture 901. Within FIG. 9 the example 3D coronary reconstruction contain is a coronary bifurcation. As described before, the 3D reconstruction can be generated from a single vessel, a bifurcation or a vessel tree. Since 902 shows a 3D reconstruction of a coronary bifurcation, two cross-sectional area curves are calculated, one from the proximal start (P) till the end of the main branch (M) represented by 905 within picture 904, and one from the proximal start (P) till the end of the branching vessel (S) represented by 910 within picture 907. From the cross-sectional area, the diameter can be determined for every point of the centerline. This diameter can for instance be derived from the cross-sectional area as the minimum, maximum of equivalent diameter as for instance taught by Onuma et at., "*A novel dedicated 3-dimensional quantitative coronary analysis methodology for bifurcation lesions*", EuroIntervention 2011 September; 7(5):629-35.

The obstruction region comprises the position of the local minimum (909) as well as corresponding obstruction borders proximal and distal (908) to the position of the minimum diameter. The distance between the proximal and distal obstruction borders (908) is defined as the lesion length. The local minimum position (909) can be based purely on the vessel geometry, for example the minimum area or diameter but it can also be defined by the physician. The obstruction boundaries define the length of the obstruction region. The obstruction boundaries (908) can be automatically determined as for instance taught by Gronenschild E, et al. in "*CAAS II: A Second Generation system for Off-Line and On-Line Quantitative Coronary Angiography*", Cardiovascular Diagnosis 1994; 33: 61-75 for single vessels, or as for instance taught by Girasis C, et al, "*Advanced three-dimensional quantitative coronary angiographic assessment of bifurcation lesions: methodology and phantom validation*", EuroIntervention 2013; 8: 1451-1460 for bifurcation or vessel trees.

To calculate the amount of vessel narrowing, the area ratio or diameter ratio of the vessel narrowing with respect to assumed healthy vessel diameter or area needs to be estimated along the vessel of interest. This healthy vessel diameter or area is also called reference diameter or reference area (906). A multitude of methods are described in existing art that are able to calculate the reference diameter or area graph as for instance taught by Gronenschild E, et al. in "*CAAS II: A Second Generation system for Off-Line and On-Line Quantitative Coronary Angiography*", Cardiovascular Diagnosis 1994; 33: 61-75 for single vessels, or as for instance taught by Girasis C, et al, "*Advanced three-dimensional quantitative coronary angiographic assessment of bifurcation lesions: methodology and phantom validation*", EuroIntervention 2013; 8: 1451-1460 for bifurcation or vessel trees. For instance, all the diameter or area data along the vessel centerline is used to automatically fit a straight line through all the diameter or area data points. Optionally, deviating vessel diameters or vessel areas values are discarded from the diameter or area data before fitting a straight line. The determination of these deviating diameter or area values can be achieved by for example creating a cumulative histogram of all the vessel diameter or vessel area data points and based on predefined or dynamic threshold value the smallest vessel diameter or area values are discarded.

Alternatively, manual reference positions are indicated by the physician according to the vessel diameter or area data. The reference positions are identification of healthy vessel parts. Next, a straight line is fitted through the diameter or area data values at the reference positions. This fitted line represents the healthy vessel diameter or area along the centerline of the vessel. Optionally, the physician is able to define a different lesion position in the vessel by manually selecting this position. The selection of the lesion position and obstruction region can be done in the generated area or diameter graph (FIG. 9, 905 or 910) or a 2D angiographic image or directly in the 3D reconstruction. Alternatively, more than one lesion position can be selected in the vessel of interest. The processor/system determines another region of interest that also shows a local narrowing of the vessel lumen. Alternatively, the physician can manually select another lesion position.

Once the obstruction region and the healthy vessel diameter and/or area along the vessel of interest is known, the anatomical lesion severity can be calculated. One of the parameters to assess the anatomical lesion severity is the percentage diameter stenosis (equation 2) or percentage area stenosis (equation 3) as can be calculated by:

$$\text{Diameter stenosis } (\%) = 1 - \frac{MLD}{\text{Reference diameter at } MLD \text{ position}} \quad \text{(equation 2)}$$

In which MLD is defined as the minimum luminal diameter, and corresponds to the diameter at the local minimum (FIG. 9, 909), and reference diameter at MLD position corresponds to the reference diameter at the location of the MLD.

$$\text{Area stenosis } (\%) = 1 - \frac{MLA}{\text{Reference area at } MLA \text{ position}} \quad \text{(equation 3)}$$

In which MLA is defined as the minimum luminal area, and corresponds to the area at the local minimum (FIG. 9, 909), and reference diameter at MLA position corresponds to the reference area at the location of the MLA.

Another anatomical parameter is the luminal plaque volume, which can be calculated using the 3D reconstruction (902) and the 3D healthy reconstruction (903). In general, the plaque volume can be calculated by subtraction of the volume of the 3D reconstruction from the volume of the 3D healthy reconstruction within a predefined region as illustrated by logical equation 4. The luminal plaque volume is typically calculated within the obstruction region.

Plaque volume = volume of     (equation 4)

(3D recontruction ∩ 3D healthy reconstruction)

Another anatomical parameter is the tortuosity. The tortuosity provides information about how tortuous (or curved) a vessel is and can be calculated for instance as taught by Grisan et al., "*A novel method for the automatic evaluation of retinal vessel tortuosity*", IEEE Transactions on Medical Imaging 2008 March; 27(3):310-9.

Figure 10:
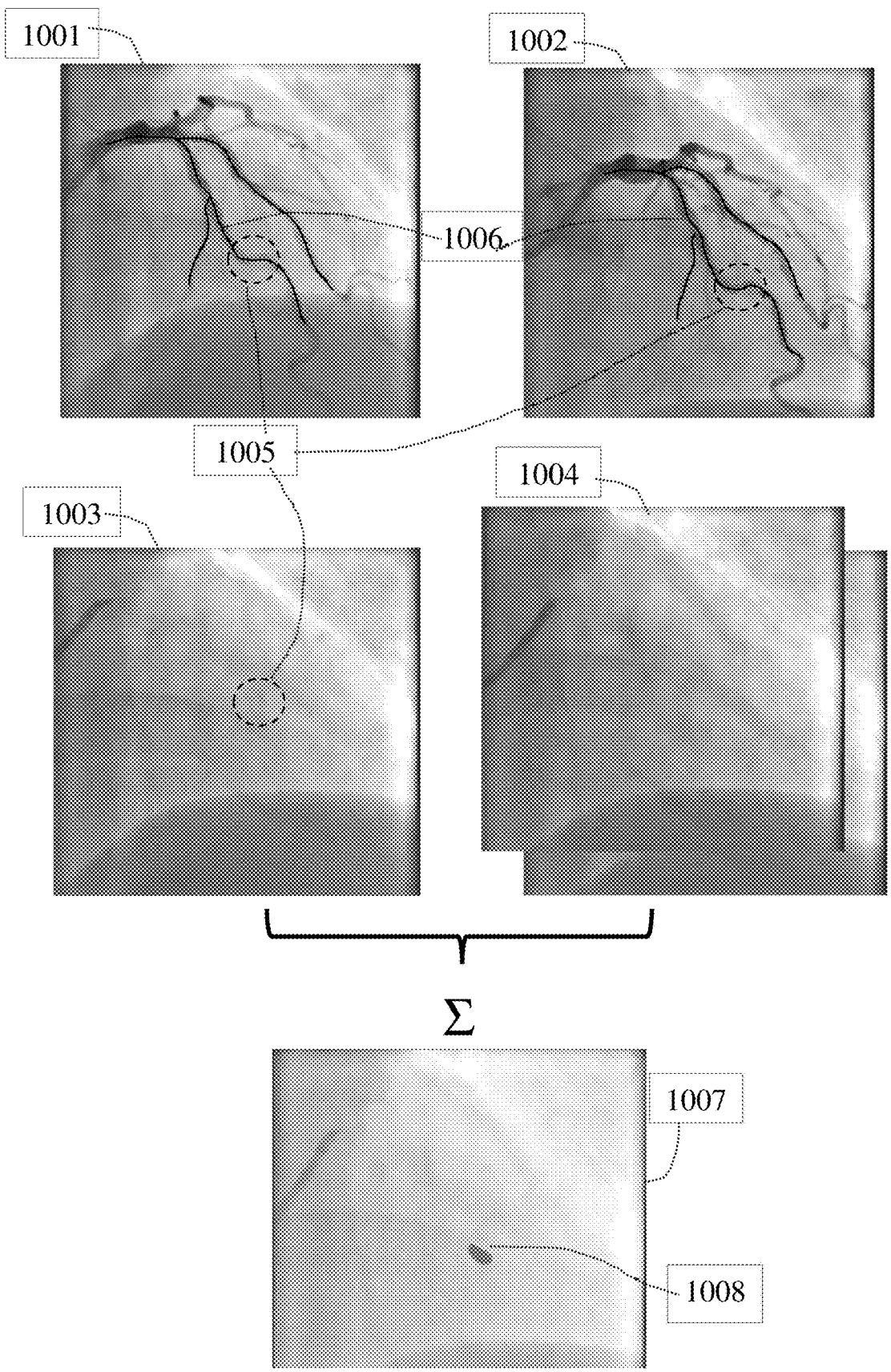
FIG. 10 shows the high-level method for determining the amount of calcified plaque.

Another anatomical parameter is the amount of calcified plaque. Although calcified plaque is radiopaque, its presents cannot be appreciated on a single X-ray image frame, and is hardly visible when assessing a sequence of X-ray images. U.S. patent application Ser. No. 16/739,718 entitled "Method and systems for dynamic coronary roadmapping" discloses a method to quantify calcified plaque by using an x-ray angiographic image sequence. The method assumes that the x-ray angiographic image sequence contains image data before and after the administration of a contrast agent and preferable at least one cardiac cycle before the administration of a contrast agent and at least one cardiac cycle after the administration of a contrast agent. Within FIG. 10 the high-level method as described by U.S. patent application Ser. No. 16/739,718 is illustrated. Within the dashed circle (1005) calcified plaque is present, however this is hardly assessable within the images (1001, 1002, 1003 and 1004). By adding the image information, after registering the images, into a single image (1007), the calcified plaque (1008) is enhanced and visible. During the registration, anatomical landmarks can be used as for instance the vessel skeleton (1006). Furthermore, quantitative analysis can be performed on the enhanced calcified plaque. The area of the calcified plaque (1008) can be calculated by manual and/or (semi) automatic detection of the calcified plaque (calcified plaque region) with the enhanced image (1009). Videodensitometric analysis can also be performed. The volume and/or mass of the calcified plaque can be derived by comparing the density of the calcified plaque region to another radiopaque region within the enhanced image or the x-ray angiographic image sequence as a result of step 101, as for instance the enhanced vessel (radiopaque vessel) due to the administration of a contrast agent. When knowing the properties of the radiopaque region, such as geometry and its (mass) attenuation coefficient, the volume and/or mass of the calcified plaque region can be computed by using the Beer-Lambert law. The radiopaque region can also be a region of the vessel as obtained from the X-ray angiographic image sequence. In this situation, the (mass) attenuation coefficient of the contrast agent needs to be known to be able to compute the volume and/or mass of the calcified plaque region by using the Beer-Lambert law. Alternatively, video densitometric analysis can be performed as for instance disclosed by U.S. Pat. No. 9,576,360.

In case the results of step 102 represents a 3D+t reconstructions, several additional anatomical parameters can be calculated. For instance, the amount of coronary motion or the change in vessels tortuosity can be taken into consideration as thought by Griffiths et al., "*4D Quantitative Coronary Artery Motion Analysis: A Novel Method for Culprit Lesion Prediction*", international Journal of Cardiovascular and Cerebrovascular Disease 6(1): 7-12, 201.

Figure 11:
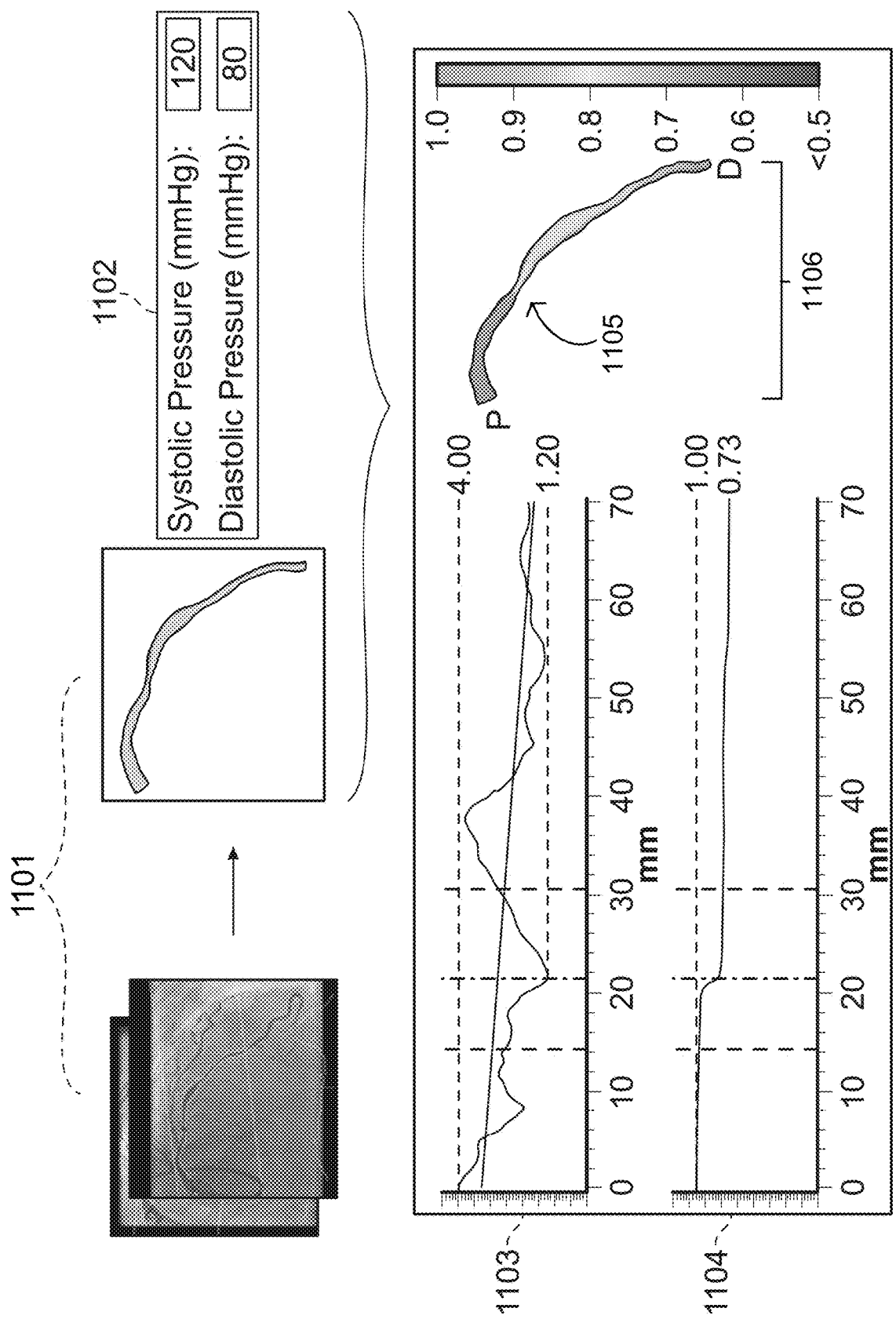
FIG. 11 shows the high-level method for determining the pressure drop along a 3D reconstruction.

Within step 104 of FIG. 1, the pressure parameters of the vessel of interest are calculated. In a preferred embodiment the pressure parameters are calculated as disclosed by U.S. patent application Ser. No. 16/438,955 entitled "Method and Apparatus for Quantitative Hemodynamic Flow Analysis" issued to Bouwman et al. In summary, the method disclosed by U.S. patent application Ser. No. 16/438,955 calculates the pressure drop along the vessel of interest instantaneously. Based on the 3D reconstruction, as a result of step 102, and the obstruction region as defined by step 103, the pressure drop is calculated by applying physical laws including viscous resistance and separation loss effects present in coronary flow behavior, as described by Gould et al. in "*Physiologic basis for assessing critical coronary stenosis. Instantaneous flow response and regional distribution during coronary hyperemia as measures of coronary flow reserve*", Am J Cardiol. 1974 January; 33(1):87-94 and Kirkeeide et al. in "*Assessment of coronary stenoses by myocardial perfusion imaging during pharmacologic coronary vasodilation. VII. Validation of coronary flow reserve as a single integrated functional measure of stenosis severity reflecting all its geometric dimensions*", J Am Coll Cardiol. 1986 January; 7(1):103-13. In order to obtain patient specific pressure parameters, the method as disclosed by U.S. patent application Ser. No. 16/438,955 incorporates the patient specific aortic pressure as measured during the catheterization procedure. FIG. 11 illustrated the method as disclosed by U.S. patent application Ser. No. 16/438,955, in which 1101 represent the step to obtain the 3D reconstruction of the vessel of interest as described by step 101 and 102 of FIG. 1. The patient specific aortic pressure is preferably obtained from the measured end-diastolic and end-systolic pressure using the guiding catheter as illustrated by 1102. The guiding catheter is placed in the coronary ostium and the aortic pressure is measured by connecting a transducer. From the measured aortic pressure trace, the end-diastolic and end-systolic pressure can be calculated as for instance a weighted average of both end-diastolic and end-systolic pressure. Alternatively, the patient specific aorta pressure can be measured at the brachial artery using a pressure cuff measurement. From the 3D reconstruction, the diameter or cross-section area graph is extracted as shown by 1103 and together with the obstruction region (1105), the pressure-drop or vFFR (vessel FFR) is calculated along the 3D reconstruction by the method as disclose by U.S. patent application Ser. No. 16/438,955 and explained before. The vFFR graph is calculated as the fraction of coronary pressure-drop at a location along the vessel length divided by the aortic pressure. The most distal vFFR value can be calculated by subtracting the total pressure drop ($\Delta P_{total}$) from the aortic pressure by the equation:

$$vFFR_{distal} = \frac{P_d}{P_a} = \frac{P_a - \Delta P_{total}}{P_a} \qquad \text{(equation 5)}$$

Furthermore, the vFFR or the pressure-drop can be visualized as a color map on the surface of the 3D reconstruction using a corresponding color or grey value as can be seen by 1106. In the color map the green color represents a low pressure-drop or high vFFR as red represents a high pressure-drop or low vFFR. Within step 105 of FIG. 1, the wall shear stress (WSS) based parameters (descriptors) of the vessel of interest are calculated and is further described by the flowchart of FIG. 12. When blood flows through an artery, it exerts forces on the vessel wall as illustrated by 1301 within FIG. 13 which visualizes a schematic representation of the forces the vessel wall is exposed to. The perpendicular component of that force vector is associated with blood pressure, leading to deformation of the cells in the vessel wall. Wall shear stress is the tangential force of the flowing blood on the endothelial surface of the blood vessel (1302). The wall shear stress vector can be decomposed in an axial and a circumferential component, called the axial wall shear stress (1303) and the circumferential wall shear stress (1304). The axial component is the component parallel with the axis of the vessel. The circumferential (or tangential) component is the component directed along the tangent at that point encircling the axis of the vessel. The radial wall shear stress is directed towards or away from the central axis of the vessel (1305). Since wall shear stress cannot be measured directly in vessels, we need to compute through solving the equations that describe the motion of fluids: the Navier-Stokes equations. The most widely used method to solve these complex equations is called computational fluid dynamics (CFD) which computes the velocity distribution within a volumetric geometry, which is in our case a vessel, given the appropriate input data (boundary conditions). Based on this velocity information, the local wall shear stress distribution in vessel along its surface can be derived and is further described by the flowchart of FIG. 12.

Figure 12:
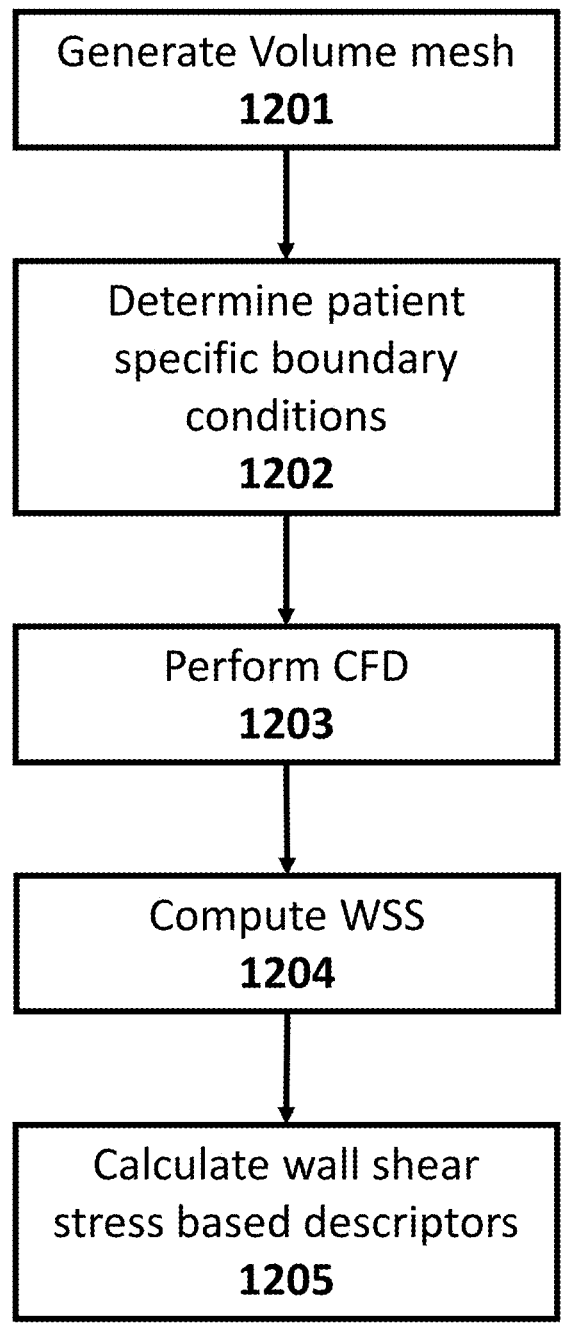
FIG. 12 shows a flow chart of a method for calculating the WSS descriptors.
Figure 13:
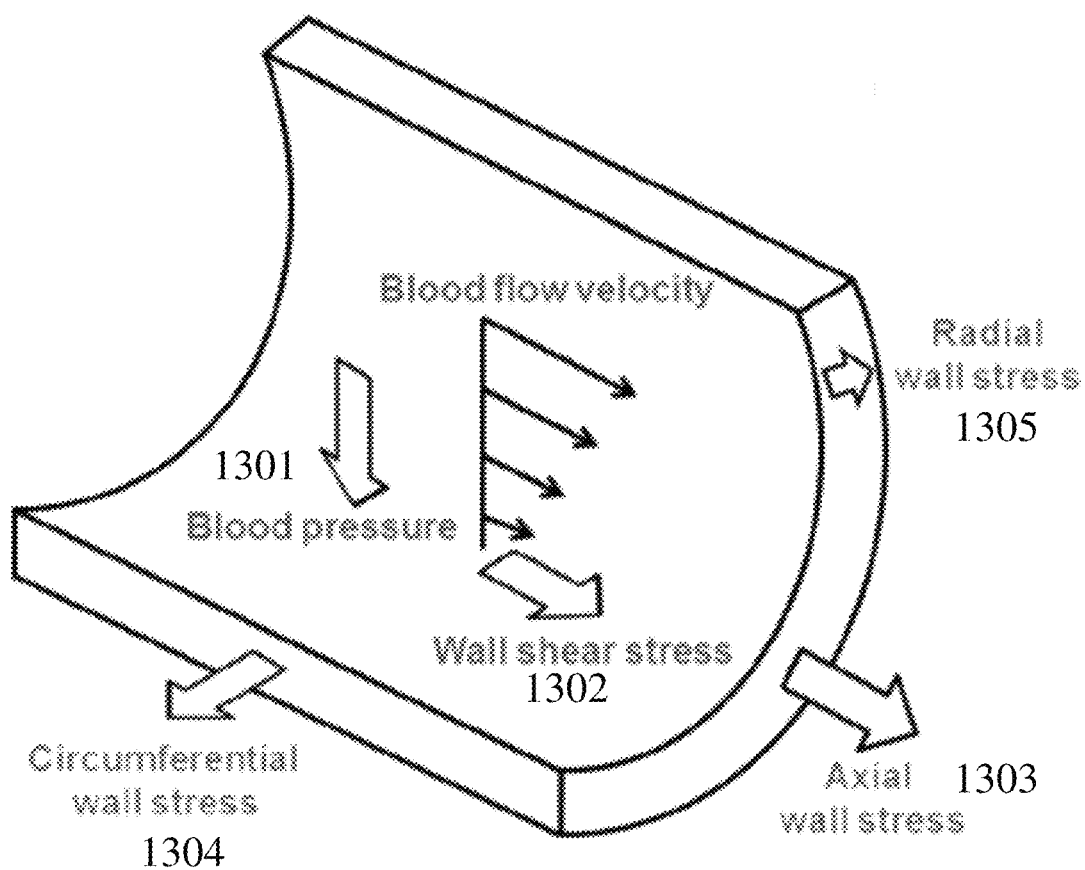
FIG. 13 illustrates the forces on the vessel wall.
Figure 14:
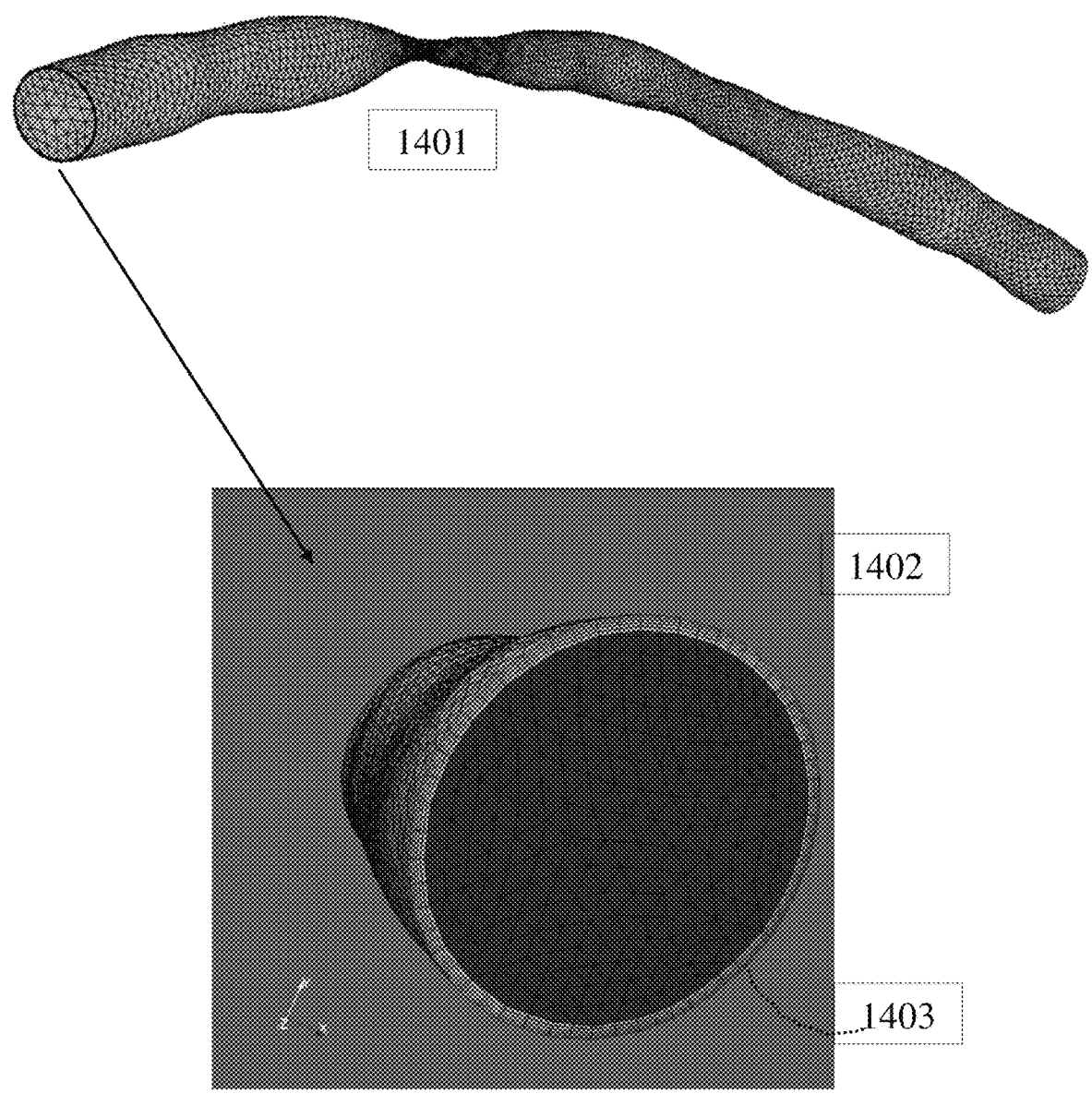
FIG. 14 illustrates the 3D volume mesh and the boundary layer.

The first step of FIG. 12, at 1201, one or more processors create a 3D volume mesh as illustrated by step 1201. For example, the 3D reconstruction can be converted into a 3D volume mesh by filling of the 3D reconstruction, as a result of step 102, with grid points which represent the volume of the blood within the 3D reconstruction. These grid points form the basis for the volumetric mesh elements, which are required to compute velocity from the governing equations for blood flow as further described by step 1203. In this meshing procedure, the individual grid spacing, or mesh size, is determined by the complexity of the vessel of interest. Generally, a finer grid spacing is required in the regions where large changes in the velocity profiles are anticipated such as at the luminal vessel wall. This implies that smaller volumetric elements are often used at the vessel wall (also called boundary mesh layer), while larger volumetric elements are admissible in the central part of the vessel, where the smaller changes in the velocity profiles are present. At high curvature or at narrow vessel segments, changes in the velocity profiles are also anticipated resulting that these regions will also benefit from smaller volumetric elements. In case the 3D reconstruction represents a bifurcation or a vessel tree, the region in which the vessel splits up smaller elements are preferred especially at the ostial side of the bifurcation. To increase the computational speed of the CFD calculations, as performed by step 1203, the element size and shape of the volume mesh can thus be varied throughout the vessel of interest. A multitude of methods are described in existing art that are able to achieve this as for instance taught by Schoeberl in "*NETGEN: an advancing front 2D 3D-mesh generator based on abstract rules*", Computing and Visualization in Science 1:41-52, 1997 or for instance, by Marchandise et al, "Quality open source mesh generation for cardiovascular flow simulations", Modeling of Physiological Flows, MS&A—Modeling, Simulation and Applications, Volume 5, 2012, pp 395-414. These adjustments can depend on location in the vessel (e.g., smaller elements near vessel boundaries) and geometric properties/features like local curvature and diameter/area changes. For example, in regions of the vessel with high curvature, high resolution volumetric elements are used, as for regions with low curvature, low resolution elements are used. This is done to minimize the amount of elements in the 3D volume mesh. FIG. 14 provides an example of the output of step 1201, in which 1401 illustrates the 3D volume mesh, with finer elements near the obstruction, and 1402 shows the inlet of the vessel in which the boundary layers are visible (1403). Optionally, the proximal part of the 3D volume mesh and/or the distal ends of the 3D volume mesh can be extended with a certain length as for instance three time the local diameter (3D mesh extension). This will ensure a smooth transition with respect to the boundary conditions as described by step 1202 and that the imposed flow is fully developed when the velocity enters the vessel of interest which will benefit the CFD computation as further described by step 1203.

Additionally, the process of step 1201, generate a 3D volume mesh, can be repeated for numerous 3D reconstructions of the vessel of interest (3D+t reconstructions, as described within step 102), where every 3D reconstruction represents a different time point within the cardiac cycle as available in the image data sequence. Instead of a single 3D volume mesh, a 3D volume mesh per time point within the cardiac cycle can be generated (further reference to as dynamic 3D volume mesh). Generation of a 3D volume mesh per time point in the cardiac cycle incorporates the dynamic behavior of the vessel during the cardiac cycle. The numerous 3D volume meshes are used further in step 1203.

Alternatively, the dynamic 3D volume mesh, created from the 3D+t reconstructions of the vessel of interest, is generated by a different approach in which the amount of volumetric elements within the dynamic 3D volume mesh is constant. This is performed, by first creating an initial 3D volume mesh at a certain time point in the cardiac cycle, for example the end diastolic phase. Next, the 3D+t reconstructions of the vessel of interest for the remaining time points in the cardiac cycle are used to obtain the geometrical deviations between the additional 3D reconstruction per time point and the initial 3D reconstruction used for generating the initial 3D volume mesh. Geometrical deviations between the 3D reconstructions can include for example, expansion, shrinkage, extension or shortening. The geometrical deviations obtained per time point are applied to the initial generated 3D volume mesh. Thus, the initial generated 3D volume mesh is adapted according the deviations obtained between the 3D reconstructions. For every time point in the cardiac cycle, a 3D volume mesh is generated with the same amount of mesh nodes and volumetric elements as the initial 3D volume mesh, only the size of each individual volumetric element is adapted/deformed. Thus, the volumetric elements can be larger or smaller as the corresponding volumetric elements in the initial generated 3D volume mesh. This mesh deformation, describing the geometrical deviations from the 3D+t reconstructions, can performed by a variety of mesh deformation methods, and the radial basis function interpolation method is one of the most robust among these. Niu et al, described in "*Radial Basis Function Mesh Deformation Based on Dynamic Control Points*", Aerospace Science and Technology Volume 64, May 2017, Pages 122-132 a mesh deformation approach based on control points which describe de geometrical variation. These control points can be extracted from the 3D+t reconstructions, an easy anatomical example of such a control point would be the location of ostial side of the bifurcation. Adaption of the initial 3D volume mesh for every time point in the cardiac cycle incorporates the dynamic behavior of the vessel during the cardiac cycle and result in a dynamic 3D volume mesh which are used further in step 1203.

Figure 15:
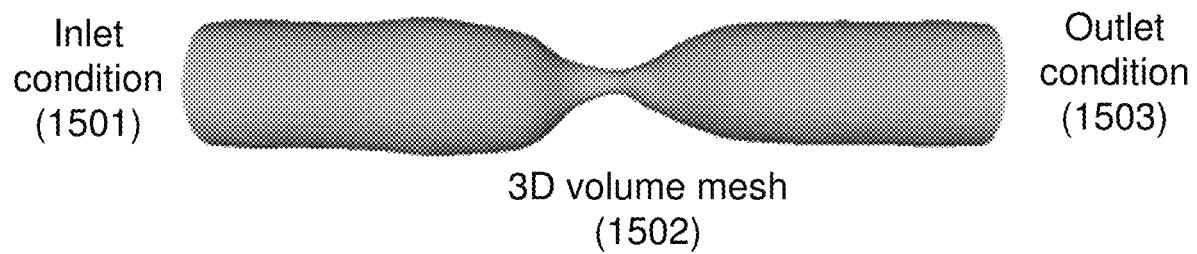
FIG. 15 shows illustrates on high level the method to solve the equations that describe the motion of fluids.

At 1202, the one or more processors determine patient specific boundary conditions. FIG. 15 illustrates on high level example of how to solve the equations that describe the motion of fluids: the Navier-Stokes equations by means of CFD; the geometry of the objects is required as a 3D volume mesh (1502), as for instance the result of the step described by 1201, and boundary condition are required at the inlet of the geometry (1501) and at the outlet of the geometry (1503). As described before, the 3D reconstruction can represent a single vessel, a bifurcation or a vessel tree. At the inlet boundary of either a single vessel, a bifurcation or a vessel tree, a blood velocity profile is applied by one of the methods as described below. The outlet conditions different between the type of vessel (single, bifurcation or vessel tree). For a single vessel, the a stress-free outlet is defined by means of a constant pressure which is typically zero Pascal as for instance taught by Krams et al., "*Evaluation of Endothelial Shear Stress and 3D Geometry as Factors Determining the Development of Atherosclerosis and Remodeling in Human Coronary Arteries in Vivo Combining 3D Reconstruction from Angiography and IVUS (ANGUS) with Computational Fluid Dynamics*" Arteriosclerosis, Thrombosis, and Vascular Biology, Vol 17, No 10, October 1997, pp 2061-2065". The outlet conditions for a bifurcation or vessel tree will be described further below.

Figure 16:
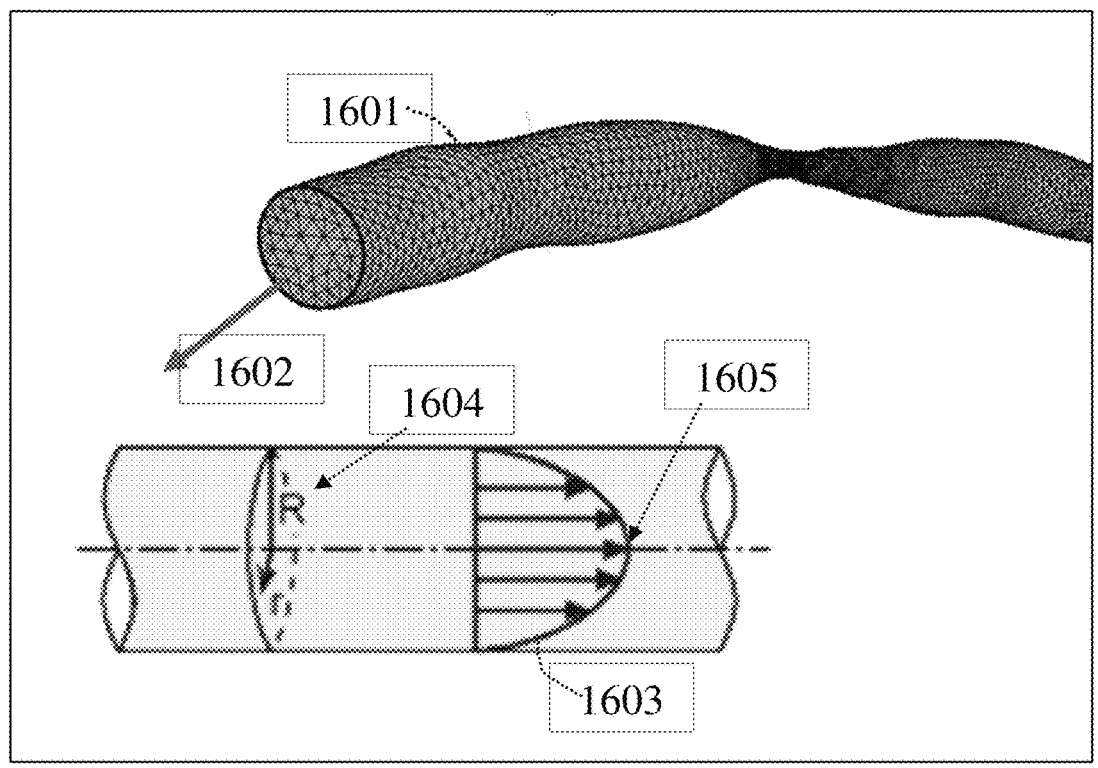
FIG. 16 shows some examples of blood velocity profiles applied at the inlet.
Figure 16:
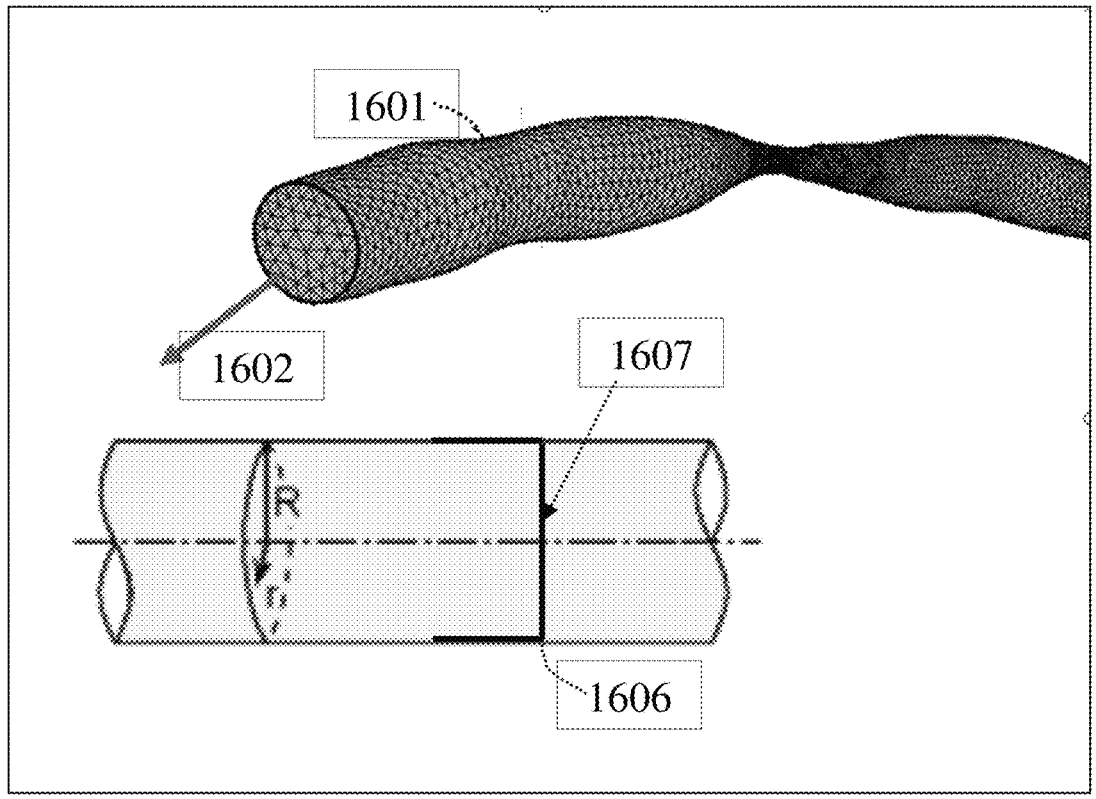

The blood velocity profile applied at the inlet can have a parabolic shape or a flat shape, as further illustrated by FIG. 16. These general blood velocity profiles can be adapted to patient specific profiles by for example scaling the blood velocity value based on the geometrical dimensions of the vessel of interest. For example, a first velocity profile may be obtained from a set of velocity provides. Each individual velocity profile represents a velocity profile across a cross section of the vessel at a proximal side of the 3D reconstruction at a corresponding momentum in the cardiac cycle. In case the velocity profile represents a flat shape, it is preferable that the 3D volume mesh is extended with a 3D mesh extension as described by step 1201. Within FIG. 16, 1601 represents the 3D volume mesh. At the inlet of the 3D volume mesh (1602), an example of a parabolic velocity profile is illustrated by 1603. The parabolic profile is based on the patient specific geometry, and is calculated for instance by:

$$v(r) = v_{max}\left(1 - \left(\frac{r}{R}\right)^2\right) \quad \text{(equation 6)}$$

Where $v_{max}$ is the maximum velocity (1605) and R is the local radius (1604).

An illustration of a flat velocity profile is provided by 1606, in which the amplitude (1607) of this flat velocity profile is equal at each volumetric element along the cross section of the vessel at a corresponding moment in the cardiac cycle.

In case the amount of blood flow is known at the inlet, the blood velocity profile can be calculated from the blood flow by using the equation:

$$\text{Flow} = \text{velocity} * \text{Area} \quad \text{(equation 7)}$$

For instance, when the blood flow is 120 ml/min, and the area at the inlet is 12 mm², the flat velocity profile can be calculated by dividing the blood flow by the cross-section area resulting in a velocity of 16.7 cm/sec. The same approach can be used for a parabolic profile, in this case the maximum velocity $v_{max}$ (from equation 6) will be two time the velocity as derived by equation 7, since equation 7 will provide the mean velocity.

The described blood velocity profile (or blood flow profile) described above does not include time variation and is also called a stationary profile. In general, a stationary profile will represent the time-average value over a cardiac cycle, and time variation of the velocity is thereby neglected.

Figure 18:
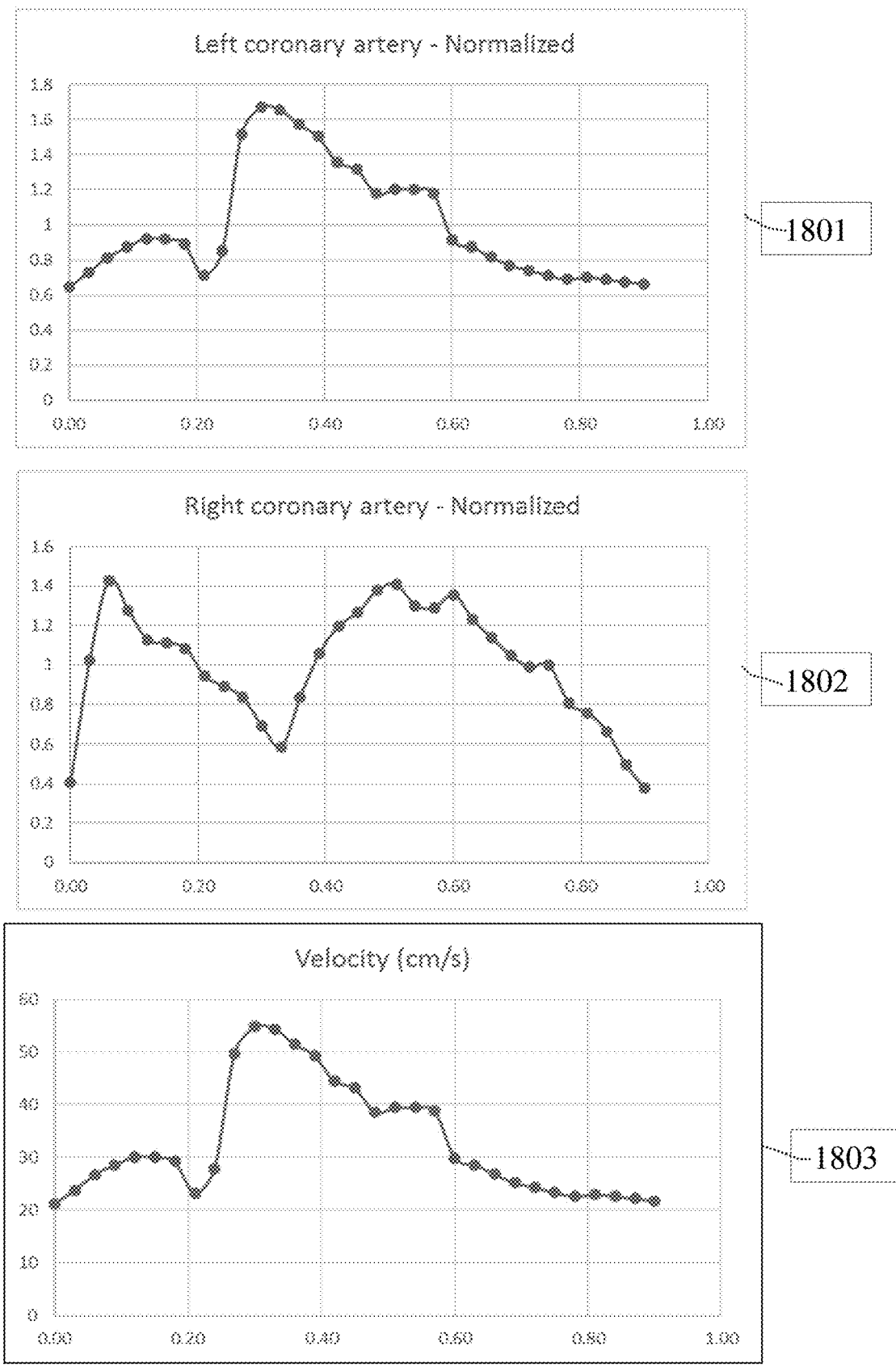
FIG. 18 shows an example of a dynamic profile.

This time variation of the velocity through a vessel, which reflects the dynamics of the blood circulation within a cardiac cycle, can be taken into consideration by defining a dynamic profile. Such a dynamic profile can be both in for a parabolic blood velocity profile and for a flat blood velocity profile. FIG. 18 shows an example of a dynamic profile, in which each dot in the graph represent a blood velocity profile at a moment in the cardiac cycle as describe above. A dynamic profile is also referred to in this patent application as blood velocity profiles or blood flow profiles or set of velocity profiles. The temporal resolution of such dynamic profile can be fixed, for instance 0.03 sec, or can be depended on the patient's heart rate.

The inlet blood velocity profiles or blood flow profiles can also be determined by direct velocity or flow measurements. Examples of such measurements are ultrasound Doppler measurements, invasive ultrasound Doppler measurements, 2D or 4D MR phase contrast measurements, thermodilution and all other measurements that capture the blood velocity or blood flow.

Figure 19:
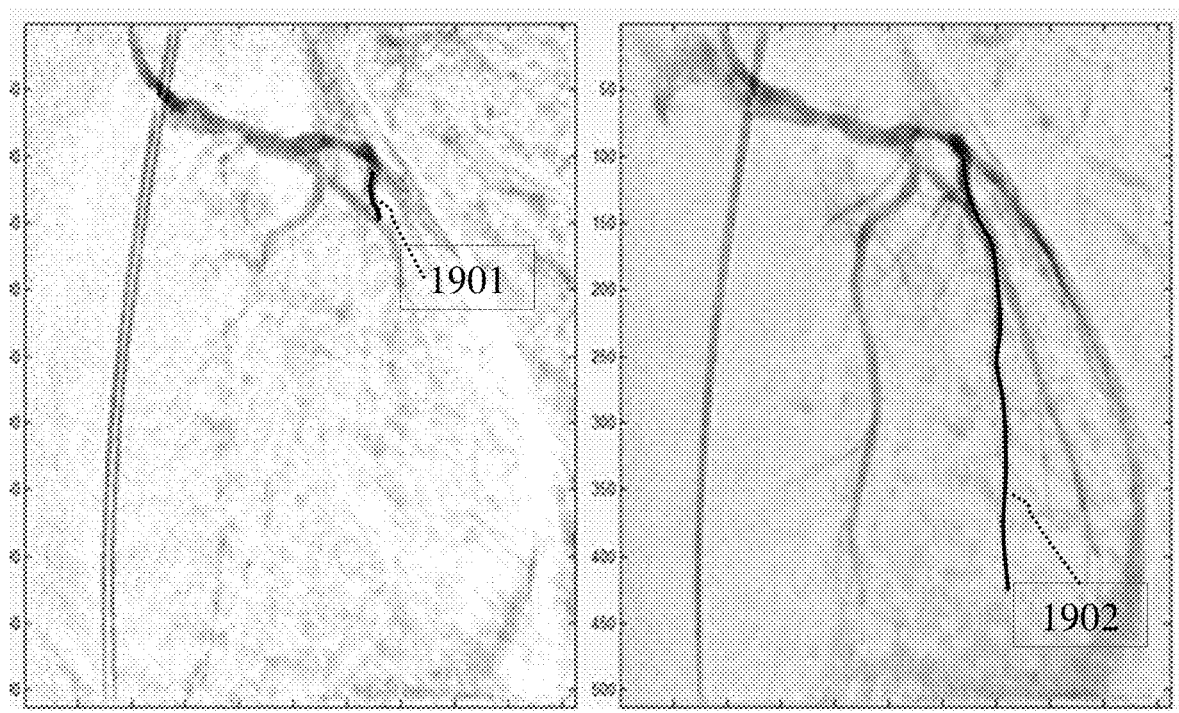
FIG. 19 shows an example of contrast bolus front detection in two frames based on X-ray Angiographic images.

Besides these direct blood velocity or blood flow measurements, the blood velocity or blood flow can be obtained from image data. For example, extracting the blood velocity based on the contrast propagation in X-ray angiography images. This method is described in U.S. patent application Ser. No. 15/971,275. In summary, the method described by U.S. patent application Ser. No. 15/971,275 measures the distance travelled by the contrast bolus front within two frames (FIG. 19; 1901, 1902). Knowing the time between the frames, the velocity or flow within the vessel of interest can is calculated. A similar approach is disclosed by Zhang et al. in "*Automatic coronary blood flow computation: validation in quantitative flow ratio from coronary angiography*", The International Journal of Cardiovascular Imaging volume 35, pages 587-595 (2019). Zhang et al, traced the centerline representing the contrast bolus along the frames from proximal to distal and the change in the length of the centerline was used to compute the coronary velocity.

The measured blood velocity profiles or blood flow profiles can be directly applied on the inlet of the model. Besides directly applying the measured blood velocities or blood flows at the inlet, those measurements can be used to create a generic blood velocity profile or blood flow profile. There can be a generic blood velocity or blood flow profile(s) created, that is applicable for all vessel types. It is also possible to create generic blood velocity profiles or blood flow profiles applicable to specific vessels, for example the right coronary artery, left coronary artery, left anterior descending artery or left circumflex.

The generic blood velocity profile(s) or blood flow profile(s) is defined assuming a specific geometry (e.g., inlet diameter or area). To be independent on the geometries used to create the generic profiles, the profiles used to create the generic profile are first normalized; dividing each value by its mean value within a cardiac cycle. FIG. 18 show an example of a generic profile for the left coronary artery (1801) and for the right coronary artery (1802). Multiple generic profiles can be created describing the flow/velocity profile along a cardiac cycle for specific coronary arteries. In case generic profiles are used, these generic profiles can be scaled to apply a patient specific blood velocity profile or blood flow profile at the inlet (FIG. 18, 1803 provides an example of a patient specific blood velocity profile after scaling). Scaling can be based on the local geometry of the vessel model at the inlet. Alternatively, the blood velocity profile or blood flow profile can be scaled based on general geometric information on specific vessels, for example the coronary vessel dimensions as reported by Dodge et al. "*Lumen Diameter of Normal Human Coronary Arteries Influence of Age, Sex, Anatomic Variation, and Left Ventricular Hypertrophy or Dilation*" Circulation, Vol 86, No 1, July 1992 pp 232-246. Scaling can be performed by for example multiplying the blood velocity profile or blood flow profile with the ratio of the inlet vessel diameter and the generic vessel diameter or using flow diameter relation as described by van der Giessen et al., "*The influence of boundary conditions on wall shear stress distribution in patients specific coronary trees*", J Biomech 2011; 44(6): 1089-95.

The inlet blood velocity profile(s) or blood flow profile(s) can represent the blood flow in rest condition state or in hyperemic condition state. The available blood velocity profile or blood flow profile can be in one of both states (rest or hyperemic, respectively) and the other state can be derived from the available profile in the other state. The conversion from one state to the other state can be applied in several ways. A linear scaling factor can be applied to convert from one state to the other state, for example a factor 5 is applied to convert a profile in rest state to a hyperemic blood velocity profile or a hyperemic blood flow profile.

The maximum hyperemic blood velocity or hyperemic blood flow can be determined based on geometrical dimensions of the 3D reconstruction as disclosed by U.S. patent application Ser. No. 16/438,955 entitled "Method and Apparatus for Quantitative Hemodynamic Flow Analysis" issued to Bouwman et al. In summary, the method disclosed by U.S. patent application Ser. No. 16/438,955 utilized the relationship between coronary velocity and coronary pressure. Based on this relationship, the aortic pressure at rest (1102) and parameters derived from the 3D reconstruction (geometry of the vessel), Ser. No. 16/438,955 described a method to calculate the patient specific hyperemic velocity. The aortic pressure at rest can also be a predefined constant value based, for instance based on empirical data, eliminating the use of the patient specific aortic pressure at rest.

Figure 20:
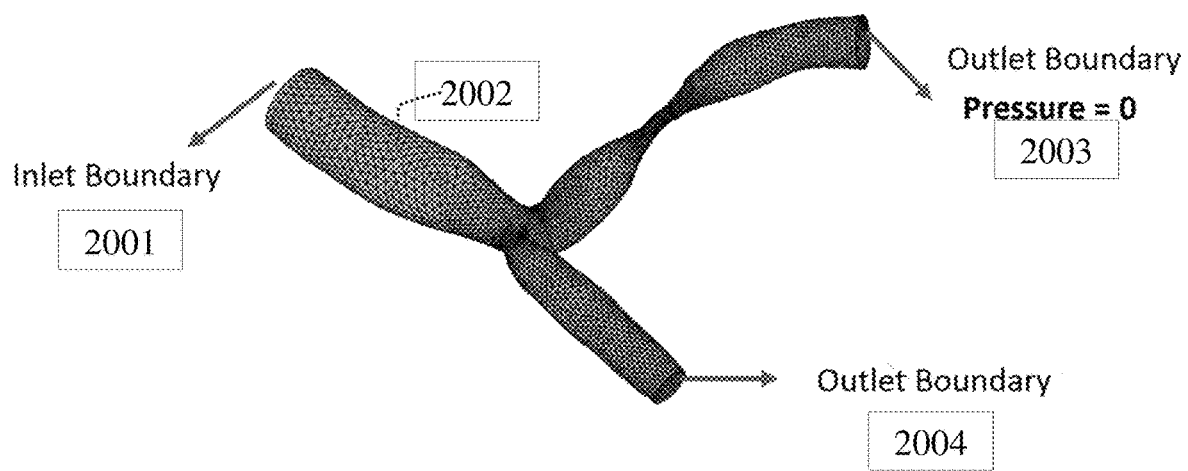
FIG. 20 shows an illustration of the outlet boundary condition in a bifurcated vessel.

As described before, the outlet boundary condition is assumed stress free, which is realized by applying zero pressure (e.g., 0 Pascal) to the outlet. In case more than one outlet boundary is present in the 3D volume mesh, one vessel outlet is set to zero pressure, as illustrated by 2003 within FIG. 20, and on the other outlet boundarie(s) (2004) an outlet blood velocity profile or blood flow profile is set. This outlet blood velocity profile or blood flow profile can be obtained by the methods as described before.

The boundary conditions on the other outlet(s) (2004) of the 3D volume mesh (2002) can be calculated based on the boundary condition applied at the inlet (2001) by using various scaling laws. The most famous scaling law, Murrays law, dates from the early $20^{th}$ century and is based on physical principles describing minimization of the energy required to transport fluids through networks (Murray et al., "*The Physiological Principle of Minimum Work: I. The Vascular System and the Cost of Blood Volume*", Proceedings of the National Academy of Sciences of the United States of America 1926; 12(3):207-14). This law prescribes a cubed relationship between the diameter and the average velocity. Various more recently developed scaling laws based on empirical data are available as well, and for coronary artery flow the exponent relating diameter to average velocity ranges between 2 and 3 as for instance describe by Kassab et al., "*Scaling laws of vascular trees: of form and function*", Am J Physiol Heart Circ Physiol 2006; 290(2):H894-903 or by Kim et al., "*Patient-specific modeling of blood flow and pressure in human coronary arteries*", Ann Biomed Eng 2010; 38(10):3195-209. Setting flow split through branches of the coronary tree, based on such a scaling law, as the outlet boundary condition is also a common and effective approach as for instance describe by van der Giessen et al., "*The influence of boundary conditions on wall shear stress distribution in patients specific coronary trees*", J Biomech 2011; 44(6):1089-95.

Alternatively, generic profiles can be used. These generic profiles can be scaled to apply a patient specific blood velocity profile or blood flow profile at the outlet. Scaling can be applied based on the local geometry of the vessel model at the outlet. Alternatively, the blood velocity profile or blood flow profile can be scaled based on general geometric information on specific vessels, for example the coronary vessel dimensions as reported by Dodge et al., "*Lumen Diameter of Normal Human Coronary Arteries Influence of Age, Sex, Anatomic Variation, and Left Ventricular Hypertrophy or Dilation*" Circulation, Vol 86, No 1, July 1992 pp 232-246.

Returning to FIG. 12, at 1203, the one or more processors compute the velocity distribution throughout the 3D volume mesh as a result from step 1201. For example, the one or more processors utilize computational fluid dynamics (CFD), to obtain velocities at volumetric elements throughout the 3D volume mesh, based on boundary conditions for the at least the portion of the cardiac cycle. The velocity distribution is computed by solving the Navier-Stokes equations by means of CFD with the use of the boundary conditions as a result of step 1202. This technique is for example described by Dadvand et al., "*An Object-oriented Environment for Developing Finite Element Codes for Multi-disciplinary Applications*", Arch Computat Methods Eng 17, 2010, pp 253-297 and for instance by Krijger et al., "*Computation of steady three dimensional flow in a model of the basilar artery*", J Biomechanics. 1992; 25:1451-1465.

Blood is a Non-Newtonian fluid, for simplification the blood is treated as a Newtonian fluid. In case of a Newtonian approach, the viscosity of blood is assumed to be constant and for example a viscosity of 1035 Pa/s and density of 1050 $kg/m^3$ can be used. A Non-Newtonian approximation of blood can be realized by utilizing the calculated shear rate at the vessel wall surface and apply a Non-Newtonian model to calculate the local blood viscosity. Non-Newtonian blood models are described in literature and a number of those models are described in Sochi "*Non-Newtonian Rheology in Blood Circulation*", 2013. Further the vessel wall is rigid and no-slip condition is assumed.

Additionally or alternatively, instead of using a single 3D volume mesh of the vessel, a 3D volume mesh over time can be used in the CFD calculation. The latter represents the dynamic behavior of the vessel during a cardiac cycle and includes the distensibility of the vessel during a cardiac cycle.

Alternatively, vessel wall mechanical properties can be applied to the CFD calculation and the pulsatile character of for example the coronary artery or any other artery can be mimicked including the distensibility of the vessel wall during a cardiac cycle.

Solving the Navier-Stokes equation can be done in several ways, for example a monolithic approach. The Navier-Stokes equation can be discretized and stabilized, which results in a set of equations. The monolithic approach solves this system of equations. (velocity and pressure are solved at the same time, no splitting). The monolithic approach allows larger computational time steps for reaching a steady state solution, which reduces the computational time. The monolithic approach works fine for low Reynolds numbers. However, when turbulent phenomena occur (high Reynolds numbers), the monolithic approach fails to reach a steady solution.

To overcome the solving problem of turbulent phenomena, RANS (Reynolds Averaged Navier Stokes), can add an additional parameter, the turbulent viscosity, to the monolithic problem. This parameter tries to capture turbulence effect into equations by modifying the viscosity of the fluid in every time step.

The CFD calculation is executed in computational time steps, for every computational time step the inlet boundary conditions are applied and for a vessel tree the outlet boundary conditions according to the corresponding computation time step. The CFD result (such as the velocity and pressure per mesh node) of the previous computational time step is used in the next computational time step.

As described before, the 3D reconstruction can represent a single vessel (FIG. 14. 1401), a bifurcation (FIG. 20), one or more branching vessels or a vessel tree (FIG. 30). The main advantage of having a 3D reconstruction of a bifurcation or a vessel tree is that the flow distribution in a bifurcating coronary artery, meaning the split of flow of the proximal vessel part (FIG. 20, 2001) into both branching vessels (FIGS. 20, 2003 and 2003) is taking into consideration during the CFD calculation. This is achieved by implying the outlet boundary conditions as described before with reference to FIG. 20. On the other hand, creating a 3D reconstruction of a bifurcation and especially of the coronary tree may be time consuming for the physician and hampering online use.

Figure 31:
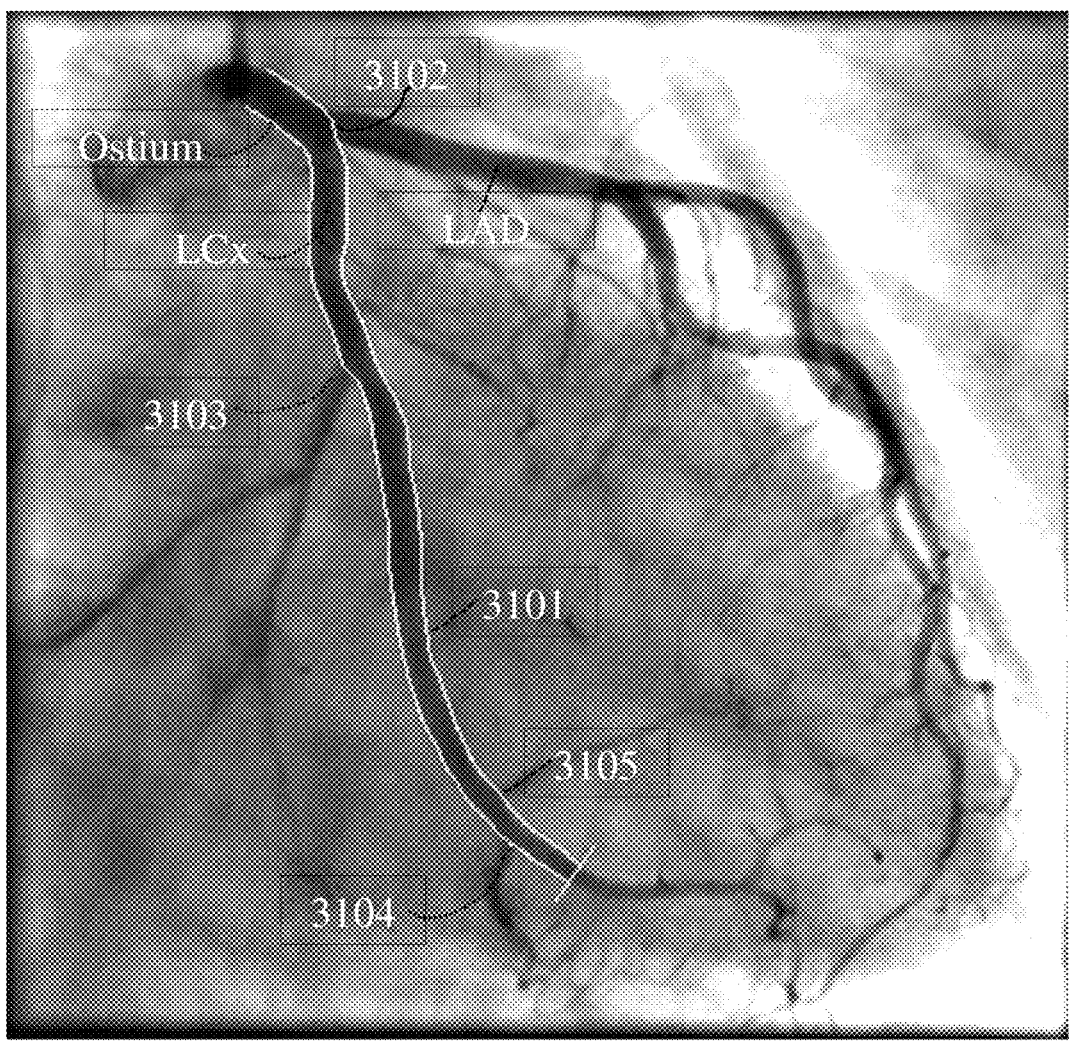
FIG. 31 provides some illustration of branching vessels of a segmented vessel within an x-ray angiographic image.

Therefore, in accordance with new and unique aspects herein, methods and systems are described that use a 3D reconstruction of a single vessel in combination with analysis of patient specific image data that is not in the 3D reconstruction (e.g., a 2D image, X-ray, etc.) in order to automatically integrate the flow reduction in the vessel of interest (in the 3D reconstruction) due to the bifurcating coronary branching vessels (that are not in the 3D reconstruction and are separate from the vessel of interest), as illustrated by FIG. 31. This is only in case the inlet boundary represent flow. Within FIG. 31, the vessel of interest (3101) is defined from the left coronary ostium up to a distal location in the left coronary circumflex. For illustration purpose within FIG. 31 only one single x-ray projection is visualized. For example, the single X-ray projection may represent the patient specific image data, whereas the 3D reconstruction is only for the vessel of interest 3101. The big bifurcation (also referred to as a side branch or branching vessel) in which the left main coronary artery splits into the left anterior descending artery and the left circumflex artery is identified by 3102. This bifurcation (3102) will split the flow from the left ostium ($Q_{ostium}$) into an amount of flow to the left anterior descending ($Q_{lad}$) and an amount of flow to the left circumflex ($Q_{lcx}$), and the conservation of mass must apply: $Q_{ostium} = Q_{lad} + Q_{lcx}$. Within FIG. 31, smaller bifurcating arteries are identified by 3103, 3104 and 3105 which results in smaller reduction of flow from the main vessel to the side branch(es). As described hereafter, methods and systems herein, take into consideration flow reduction along the vessel of interest (3101), where the flow reduction is due the loss of flow towards the branching vessels (e.g., bifurcations depicted by 3102, 3103, 3104, 3105 in FIG. 31). The flow reduction is included within the CFD calculation. In order to incorporate flow reduction along the vessel of interest during the CFD calculation (step 1203), the location of the branching vessels needs to be identified even through the branching vessels are not in the 3D reconstruction of the vessel of interest. It is not required that all branching vessels are identified along the vessel of interest, but instead at least the branching vessels that contribute to a significant reduction of the flow should be considered, for instance 3102 and 3103 as depicted in FIG. 31.

In accordance with new and unique aspects herein, methods and systems perform the following operations in connection with calculating the WSS descriptor(s) for a coronary tree that includes a branching vessel that is not included in the 3D reconstruction. The methods and systems identify a branching vessel from the patient specific image data (e.g., from the 2D x-ray). The methods and systems projects the branching vessel onto the 3D reconstruction of the vessel of interest. The methods and systems calculate a first flow within the vessel of interest proximal to the branching vessel, and calculate a second flow within the vessel of interest distal to the branching vessel. The methods and systems assign a difference between the first and second flow to the branching vessel and assign a boundary condition to the surface of the vessel of interest based on the difference. The boundary condition is located at surface elements corresponding to the location of the branching vessel. The boundary condition is then used in the calculation of the WSS descriptor(s). More specifically, the boundary condition is used utilized in the CFD when obtaining velocities at volumetric elements throughout the 3D volume mesh, and the WSS vectors are calculated at the corresponding volumetric elements along the surface of the 3D volume mesh.

Figure 32:
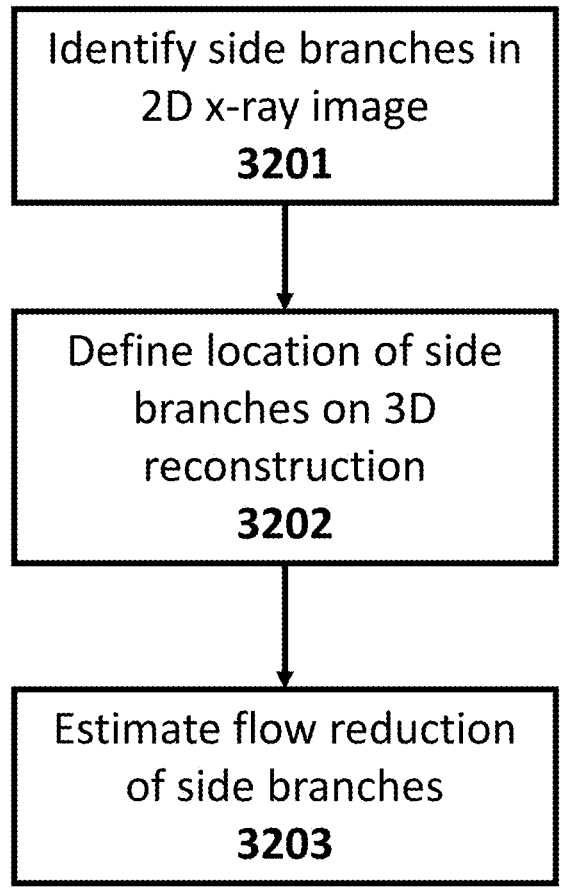
FIG. 32 shows a flow chart of a method for identification of branching vessels within the 3D reconstruction and to estimate the flow reduction of the branching vessels.
Figure 33:
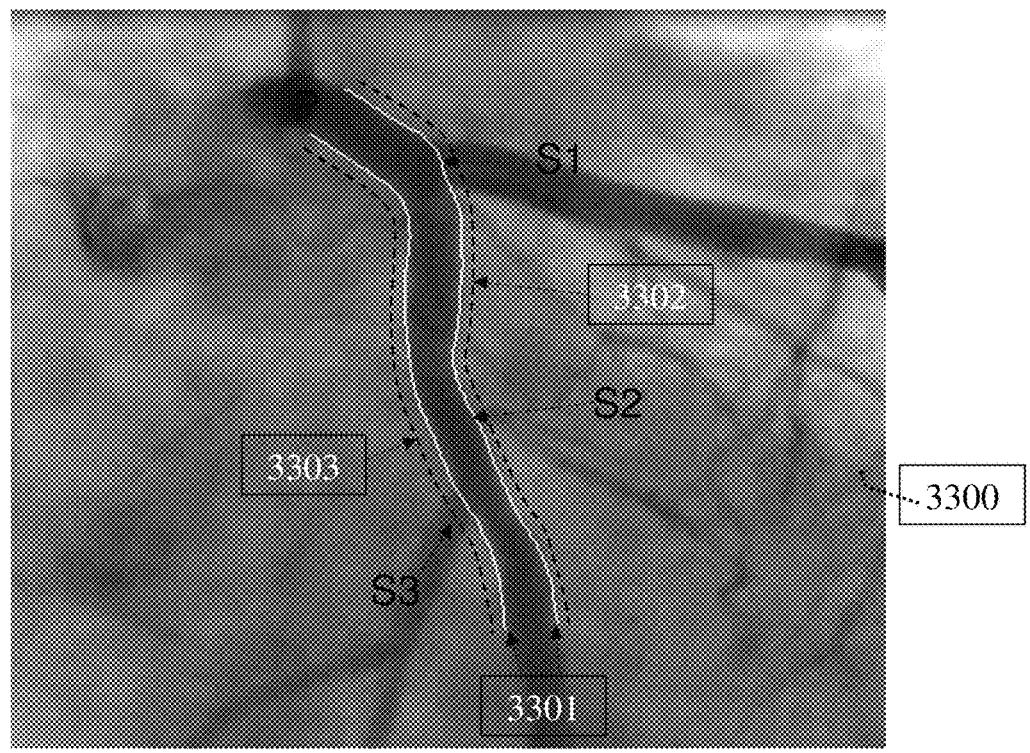
FIG. 33 shows an illustration of a method to define the branching vessels present within the segmented vessel within an x-ray angiographic image.
Figure 33:
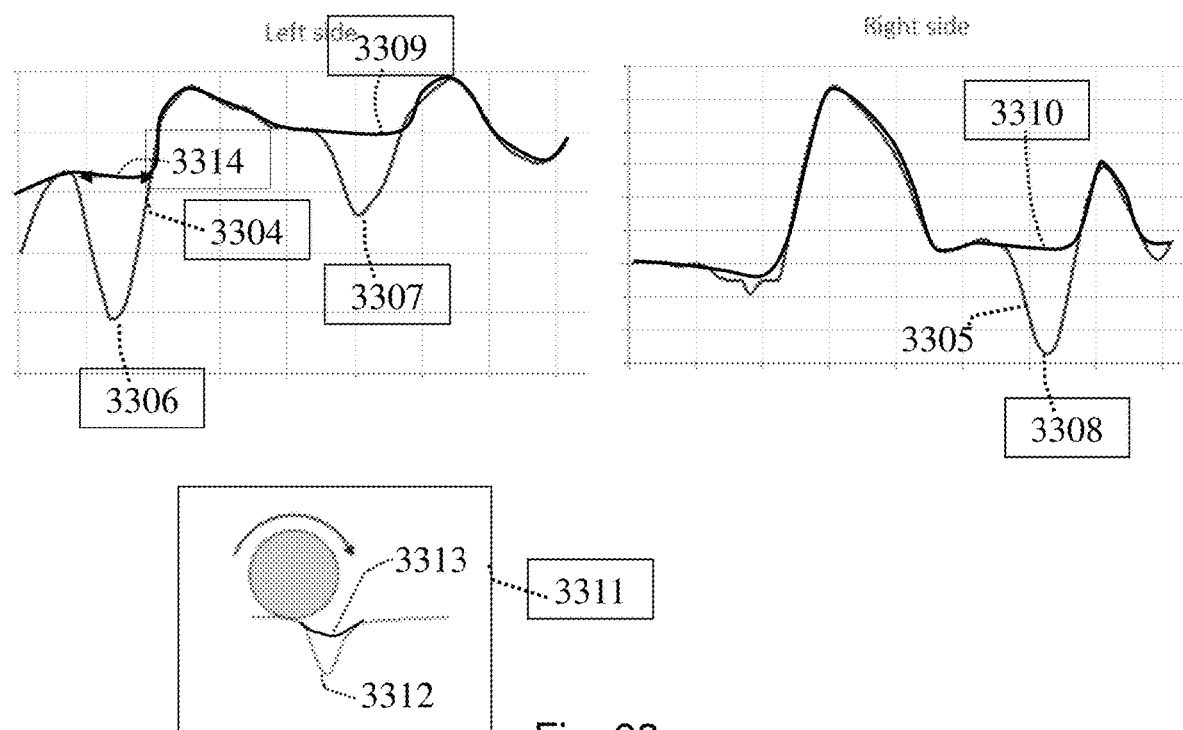

The identification of the branching vessels (also referred to as side branches) within the 3D reconstruction is further described by the flowchart of FIG. 32. At step 3201, the branching vessels in at least one x-ray angiographic image frame (from the patient specific image data), as used within the steps described by the flowchart of FIG. 4 to create the 3D reconstruction of the vessel of interest, are identified. An example to identify the branching vessels within one x-ray angiographic image frame is further described by reference to FIG. 33. The detected luminal borders, as a result of the flowchart represented by FIG. 4, are illustrated by 3301. Sampling the image intensity in two strips just outside the detected luminal borders, results in two background graphs; one for the left side and one for the right side. Left and right is defined by the start of the luminal borders, when the luminal borders start at the proximal position of the vessel as indicated by P in picture 3300, left background graph (3304) is resampled along the strip identified by 3302, and the right background graph (3305) is resampled along the strip identified by 3303. In case a branching vessel is present, the local intensity along the background graph would show a local drop of intensity due to the present of a branching artery. For instance, the branching vessel identified by S1 in picture 3300 is visible in the left background graph 3304 by the local drop in intensity indicated by 3306. The same is true for branching vessel S2 and S3, indicated by 3307 and 3308 respectively. These local drop of intensity in background graphs can be automatically detected and thereby automatically identifying the branching vessels. For instance, the background graphs can be corrected (3309, 3310) by some criteria, in which automatically identifying local minima's can be archived. Such a method could be based for instance on a rolling-ball algorithm, which rolls a ball with a predefined radius along a curve, as illustrated by picture 3311. The graph before passing the rolling ball is presented by 3312, and after applying a rolling-ball algorithm, the graph is presented by 3313. The radius of the ball will define the width of the graph which can be corrected, and this width is related to the size of the branching vessel in question. Other methods can be applied for identifying local minimum (defining branching vessels) in the background graphs. In other embodiments, one or more machine learning systems or other forms of computer-based artificial intelligence can be trained or otherwise configured to detect one or more branching vessels of interest (e.g., along the luminal boundaries detected) directly from the image sequence. The machine learning system(s) can be embodied by one or more artificial neural networks, decision trees, support vector machines, and/or Bayesian networks. The machine learning system(s) can be trained by supervised learning involving of a set of training data, unsupervised learning, or semi-supervised learning.

Figure 34:
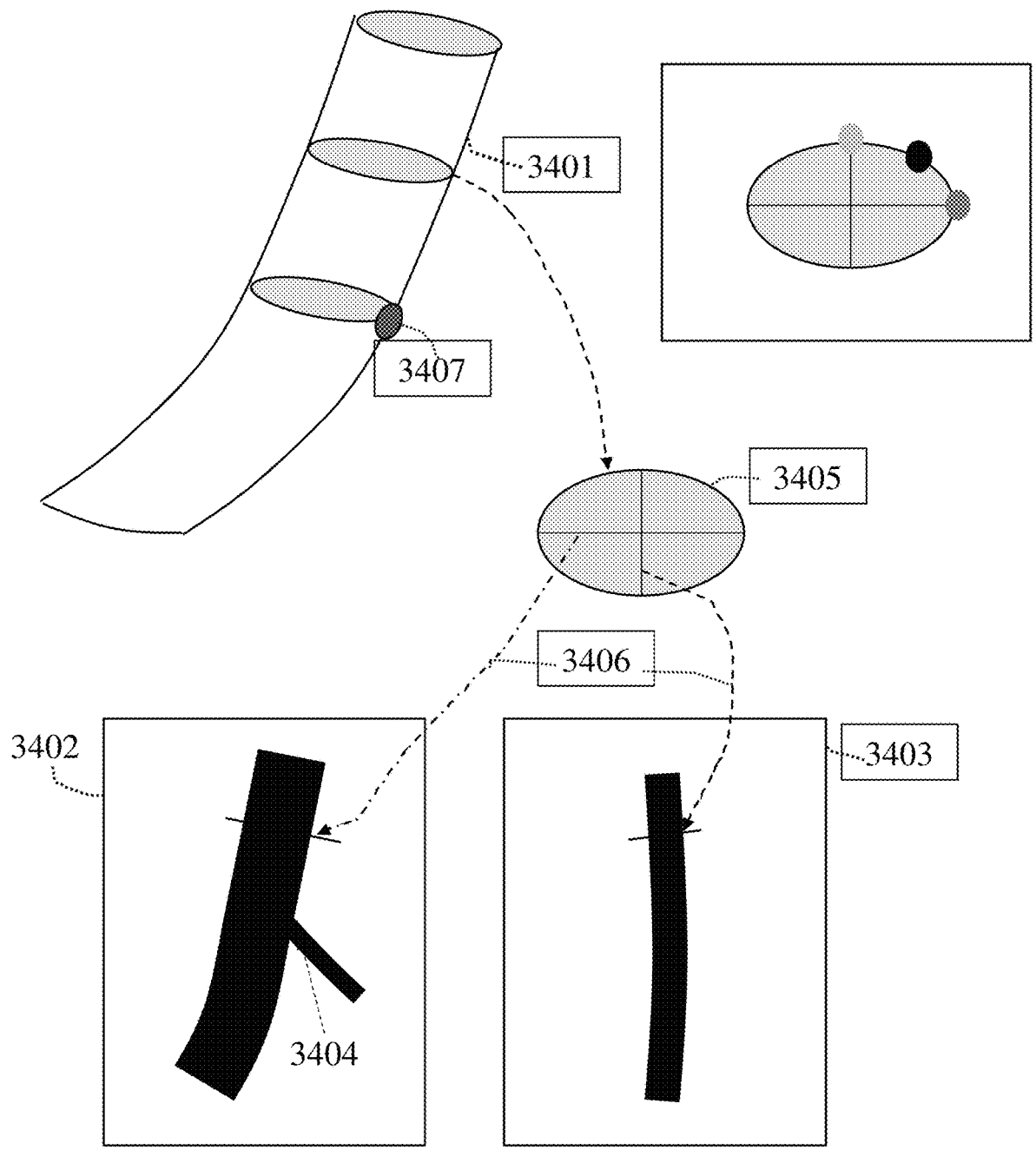
FIG. 34 illustrates an example to define the location of branching vessels identified on an x-ray image sequence at the 3D reconstruction.
Figure 35:
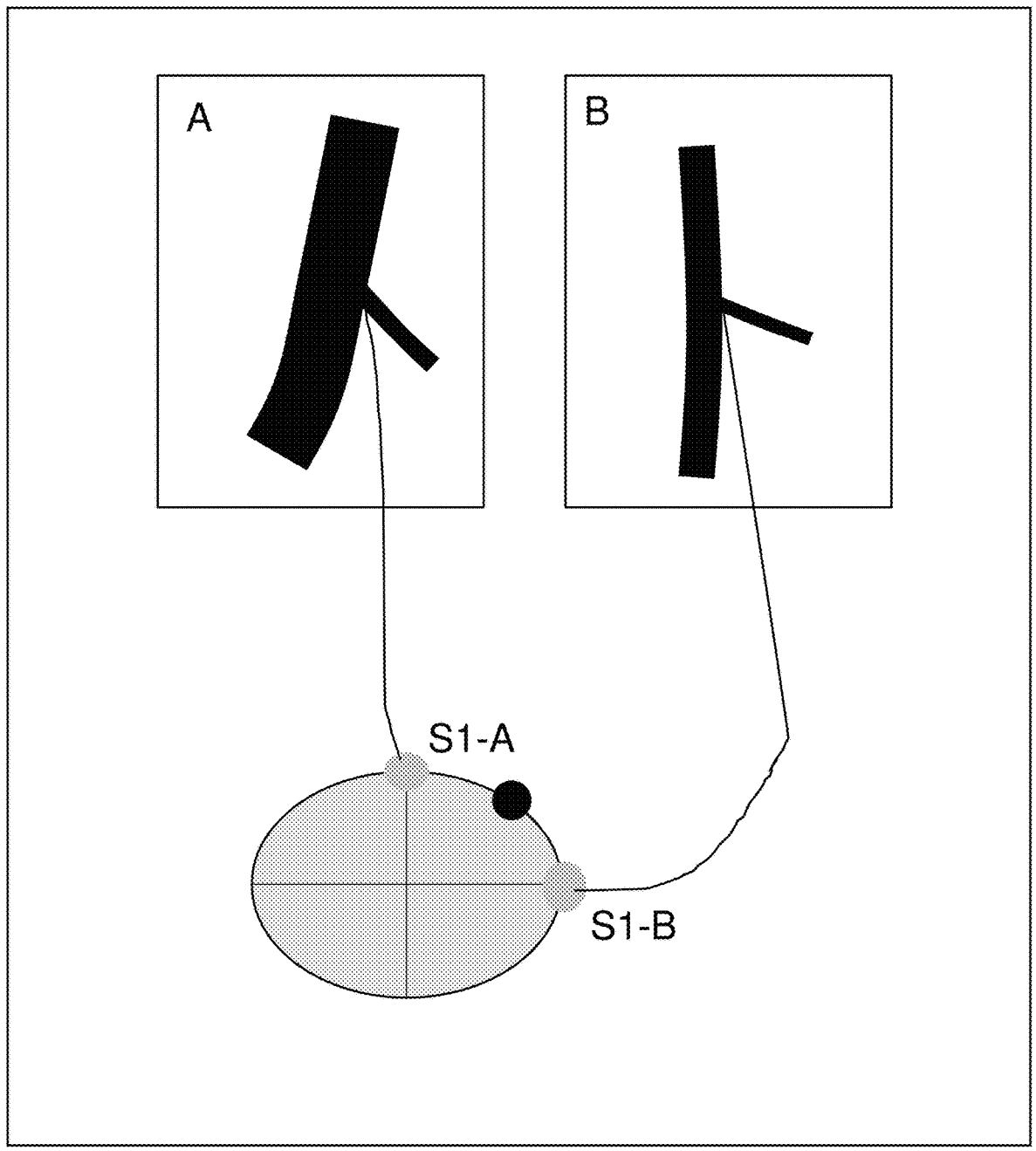
FIG. 35 illustrates an example on how to position the branching vessel at the surface of the 3D reconstruction.

At step 3202, the branching vessel(s) is projected onto the 3D reconstruction. For example, the identified branching vessels in one or more x-ray angiographic image frames (as a result of step 3201) are transferred to the correct spatial locations on the surface of the 3D reconstruction of the vessel of interest. A method to project the branching vessels onto the 3D reconstruction, namely to define the location of the detected branching vessels on the 3D reconstruction, is illustrated with reference to FIG. 34. A schematic example is presented of a 3D reconstruction 3401 by using two 2D images, 3402 and 3403. Within the 2D image 3402, a branching vessel is present represented by 3404 which can be identified by the methods as explain by step 3201 of FIG. 32. As the 3D reconstruction (3401) is based on the luminal borders detected from the 2D images (3402 and 3403), the relationship between the 2D images and the 3D model is known. Meaning that a cross section of the 3D model (3405), the position and diameter of the luminal borders from the 2D images with respect to its cross-section area and location is known. To illustrate, the cross section 3405 from a location of the 3D reconstruction (3401), is based on the location and diameter as indicated by 3406. This means when a branching vessel is detected within a 2D image (3404), the process can identify its location on the 3D model (3407). In case the branching vessel is also detected in the other 2D image, the process can estimate the position along the surface of the 3D reconstruction by incorporating the difference in projection between the 2D images used to create the 3D reconstruction. For instance, in case the projection difference between the images is 90 degrees, and the branching vessel is visible in both 2D images (image A and image B within FIG. 35), the true 3D location of that branching vessel is estimated in the middle of the circumference of the quadrant spanning between S1-A and S1-B as illustrated by FIG. 35.

Returning to FIG. 32, at step 3203, the flow reduction of each branching vessel is estimated for each branching vessel on the 3D reconstruction as a result of step 3202. For example, the process calculates a first flow within the vessel of interest proximal to the branching vessel and calculates a second flow within the vessel of interest distal to the branching vessel. The process then assigns a flow difference between the first and second flows to the branching vessel.

Figure 36:
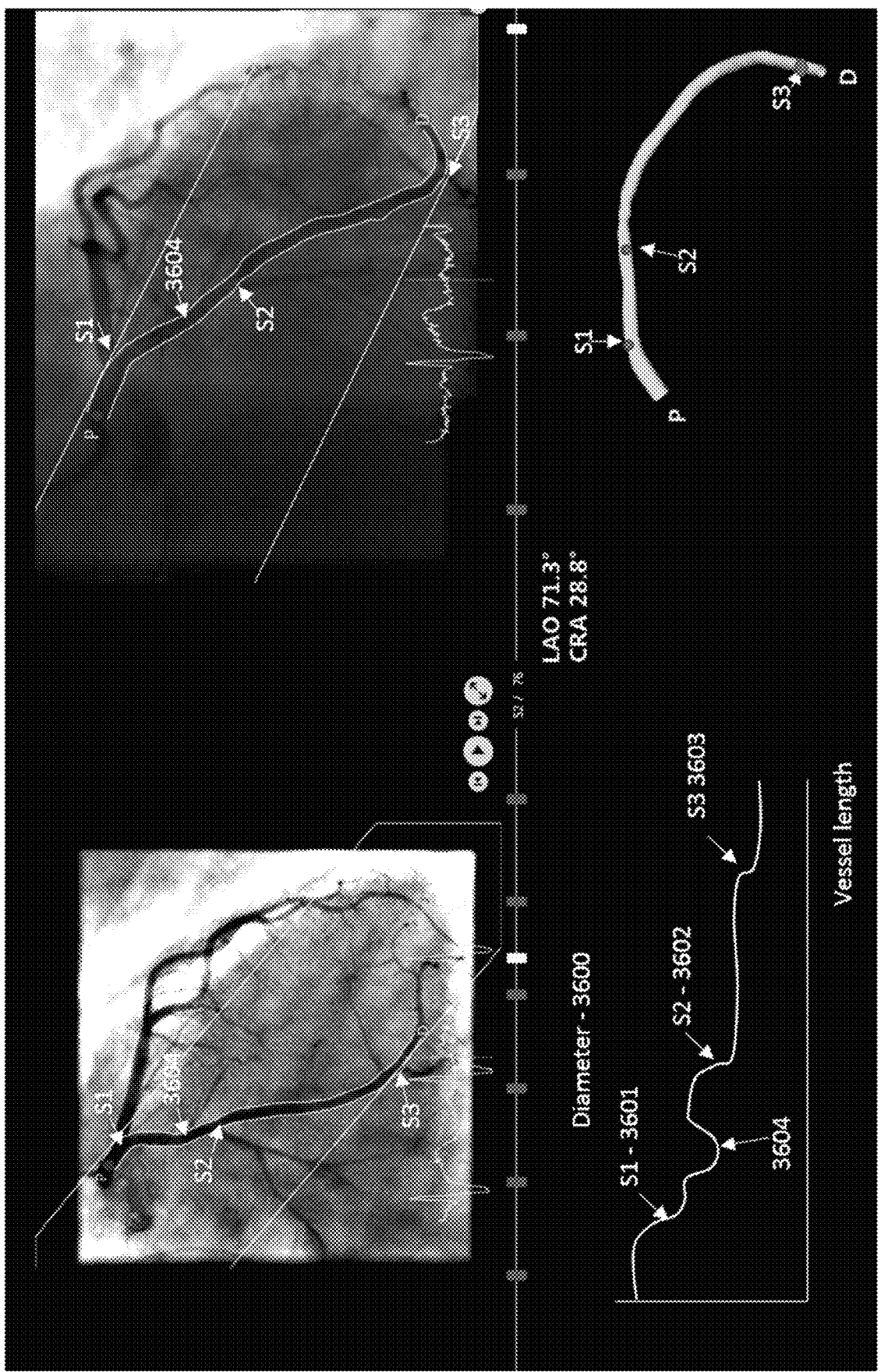
FIG. 36 shows an illustration of a method for estimating the flow reduction of each side branch.
Figure 37:
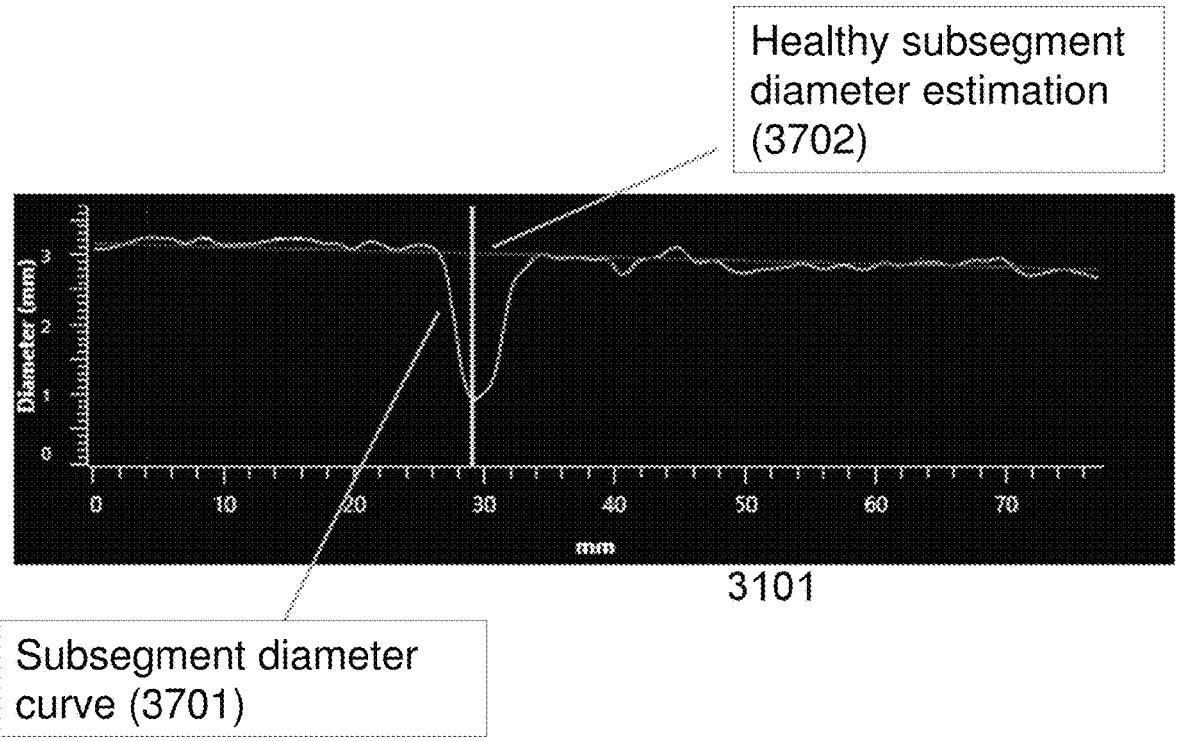
FIG. 37 illustrates an example of defining the healthy vessel estimation by fitting a straight line through the extracted geometrical information.
Figure 38A:
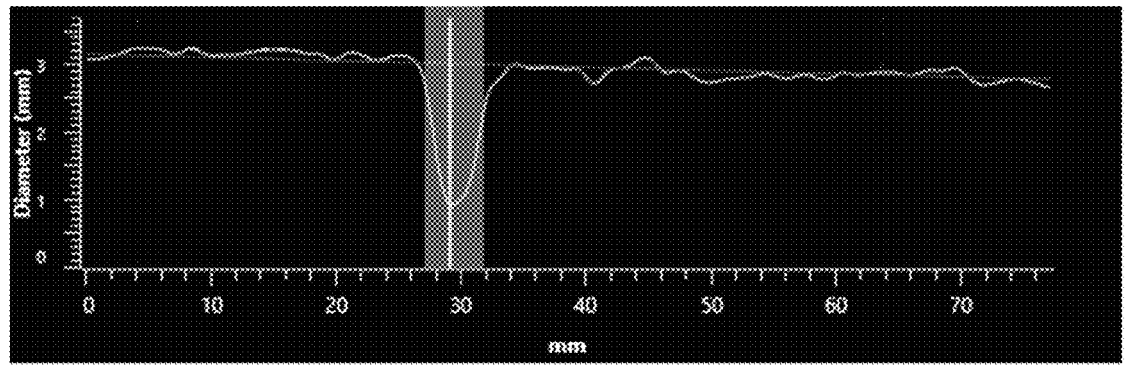
FIG. 38A and FIG. 38B illustrate an example of defining the healthy vessel estimation by fitting a straight line through the designated geometrical information.
Figure 38B:
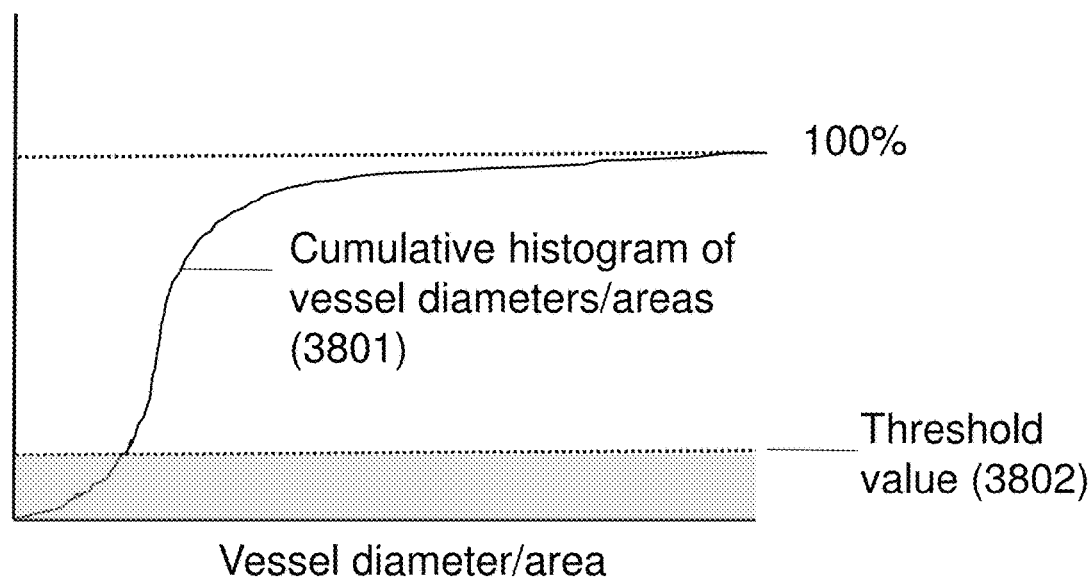
Figure 39:
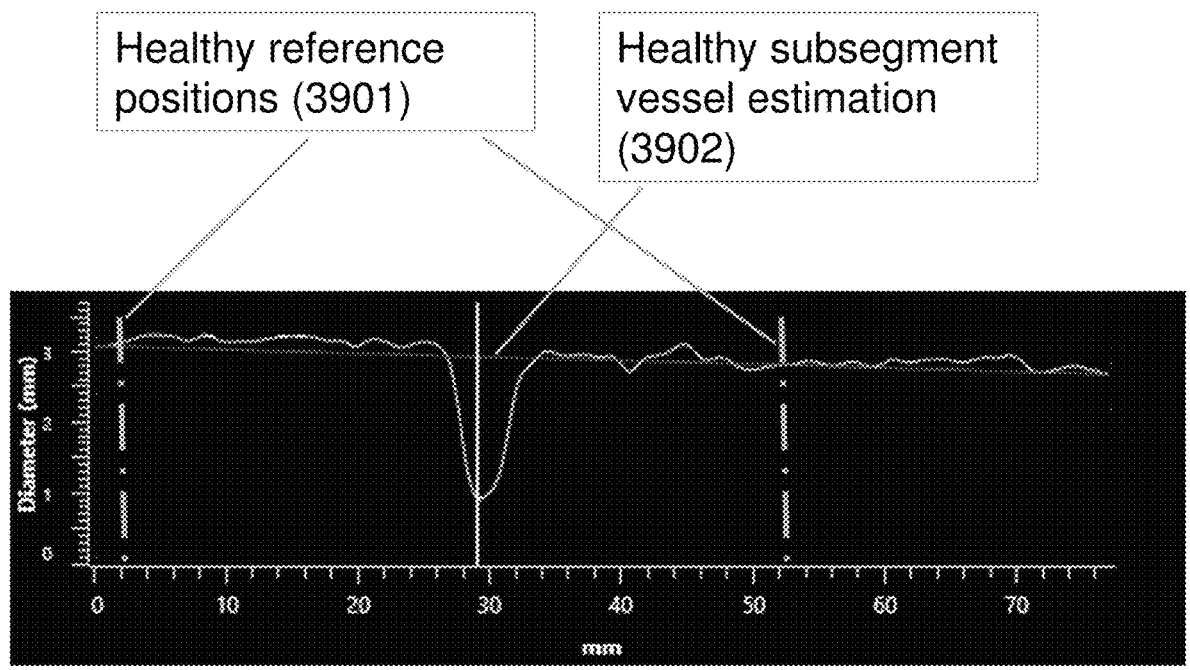
FIG. 39 illustrates an example of defining the healthy vessel estimation by fitting a straight line through reference positions.

By way of example, one approach for estimating the flow reduction is based on the scaling laws as described before at step 1202 of the flowchart from FIG. 12. This approach assumes the diameter of the branching vessel is known. This branching vessel diameter can be estimated from the width of the local minimum (3314) of the background curve corrected by the correction method as described by step 3201 of the flowchart from FIG. 32. Since the location of the branching vessel is known in the 3D model, the diameter/area of the 3D model just proximal to the branching vessel is known. With this information, the diameter just proximal to the branching vessel of the 3D model and the diameter of the side branch, the flow reduction of that branching vessel can be computed by the scaling laws as described before. Another method for estimating the flow reduction of each branching vessel is based on the teaching and methods as disclosed by U.S. patent application Ser. No. 16/438,955 entitled "Method and Apparatus for Quantitative Hemodynamic Flow Analysis" in which the inventors indicated that the coronary tree exhibits a constant velocity throughout the healthy coronary tree considering a single patient. A method for estimating the flow reduction of each branching vessel which incorporates these teachings is further explained with reference to FIG. 36. Within FIG. 36, a 3D reconstruction is presented based on the luminal border segmentation in two x-ray angiographic sequences as described before with reference to step 101 and 102 of FIG. 1. Within FIG. 36, three branching vessels are detected and located on the 3D reconstruction as a result of step 3201 and 3202. From step 103, anatomical parameters are calculated such as the diameter along the 3D reconstruction (along the 3D centerline) as illustrated by 3600. Since the 3D reconstruction is a single vessel, its diameter along the 3D reconstruction shows step-down due to the reduction of diameter after each branching vessel as illustrated by 3601, 3602 and 3603 for the branching vessels S1, S2 and S3. In order to incorporate a constant velocity throughout the healthy coronary tree, an estimate of the healthy diameter along the 3D reconstruction is required. Since the 3D reconstruction can include at least one disease location (e.g., 3604), the diameter graph of the 3D reconstruction is divided into n+1 segments, in which n represents the number of branching vessels identified on the 3D reconstruction. From each segment, a healthy diameter (reference diameter) is estimated. One method to calculate the healthy diameter within a subsegment of the diameter along the 3D reconstruction is to include all the diameter or area data along the vessel centerline of the subsegment (3701 of FIG. 37) and automatically a straight line is fitted through all the diameter or area data points as illustrated by 3702 of FIG. 37. This fitted line represents the healthy vessel diameter or area along the centerline within the subsegment. Using this approach, the resulting healthy diameter or area line is based on all diameter or area values along the vessel subsegment and therefore includes also the diameters or areas within the diseased vessel part, this might cause a slight underestimation of the computed healthy diameter or area line. One approach to improve the reference diameter area computation would be by performing an optionally step in which deviating vessel diameters or vessel areas values are discarded from the diameter or area data. The determination of these deviating diameter or area values can be achieved by for example creating a cumulative histogram of all the vessel diameter or vessel area data points (3801 of FIG. 38B). Based on predefined or dynamic threshold value (3802 of FIG. 38B), the smallest vessel diameter or area values are discarded (3803 of FIG. 38A). Next, a straight line is fitted through the remaining diameter or area data points. This fitted line represents the healthy vessel diameter or area along the centerline of the subsegment. Alternatively, manual reference positions are indicated by the physician according to the vessel diameter or area data (3901 of FIG. 39) or automatically detected as for instance taught by Gronenschild E, et al. in "*CAAS II: A Second Generation system for Off-Line and On-Line Quantitative Coronary Angiography*", Cardiovascular Diagnosis 1994; 33: 61-75. The reference positions are identification of healthy subsegment vessel parts. Next, a straight line (3902 of FIG. 37) is fitted through the diameter or area data values at the reference positions as for instance taught by Gronenschild E, et al. in "*CAAS II: A Second Generation system for Off-Line and On-Line Quantitative Coronary Angiography*", Cardiovascular Diagnosis 1994; 33: 61-75. This fitted line represents the healthy vessel diameter or area along the centerline of the vessel. Knowing the healthy diameter of the each subsegment, we can calculate the flow reduction. From the flow inlet condition (step 1202), we can calculate the velocity based on either the reference diameter from the first subsegment or from the inlet geometry (1501). Using this velocity and the healthy reference diameter for each subsegment, the flow reduction can be calculated by $Q_{previous\ segment} - Q_{current\ segment}$, which represents a flow difference between the first and second flows (also referred to as proximal and distal flows relative to the corresponding branching vessel).

Figure 40:
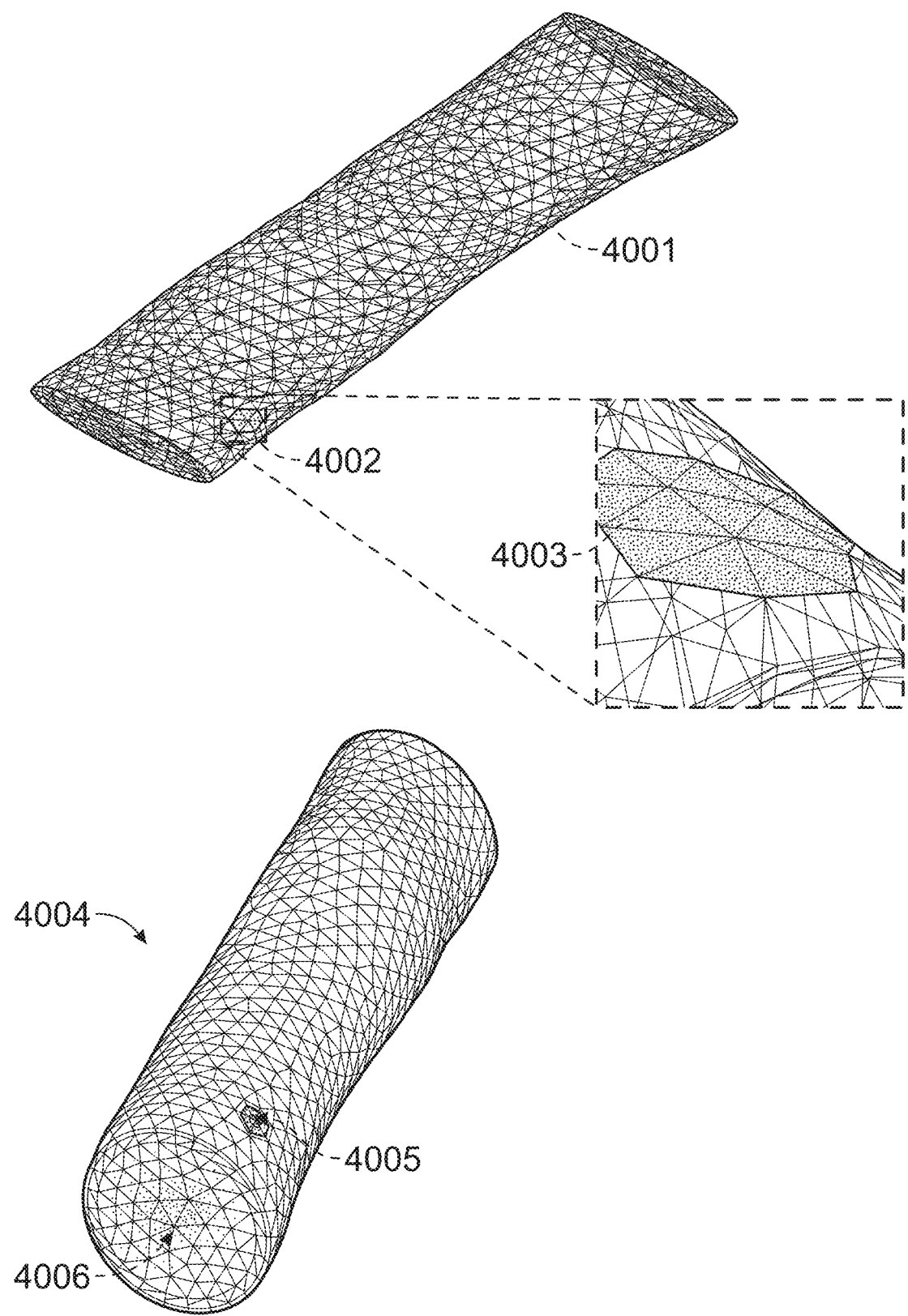
FIG. 40 shows an illustration of a method to incorporate the branching vessel into the volumetric mesh and shows the results of the CFD calculation.

The process assigns a boundary condition to the surface of the vessel of interest based on the difference. The boundary condition is used to calculate flow reduction due to each branching vessel in the CFD calculation. More specifically, on the generated volume mesh as a result of step 1201, volumetric elements are identified as additional outlet (boundary condition) corresponding to the location of the branching vessels as identified on the 3D reconstruction. FIG. 40 shows an example of a single side branch, 4001 represents the volume mesh of a 3D reconstruction, and 4002 shows the additional outlet of the side branch. For each branching vessel a small number of volumetric elements are identified (4003) as an additional outlet, the number of volumetric elements may depend on the flow reduction due to the branching vessel in question and to the size of the volumetric elements. Within FIG. 40, the result of a CFD calculation is presented by 4004, in which the velocity is shown as a color scale in picture 4004. At the outlet of the volume mesh, representing the distal part of the 3D reconstruction, the velocity is visualized by (4006) and 4005 shows the velocity at the additional outlet representing the side branch. Optionally, at the location of the side branch, the 3D volume mesh can be extended with a tube representing branching vessel diameter with a certain length as for instance three time the local branch diameter.

Alternatively, the calculation of the pressure parameters as described by step 104 from the flowchart of FIG. 1 can also be calculated from the result of step 1203, since pressure gradient of each volumetric element is part of solving the Navier-Stokes equations.

Figure 21:
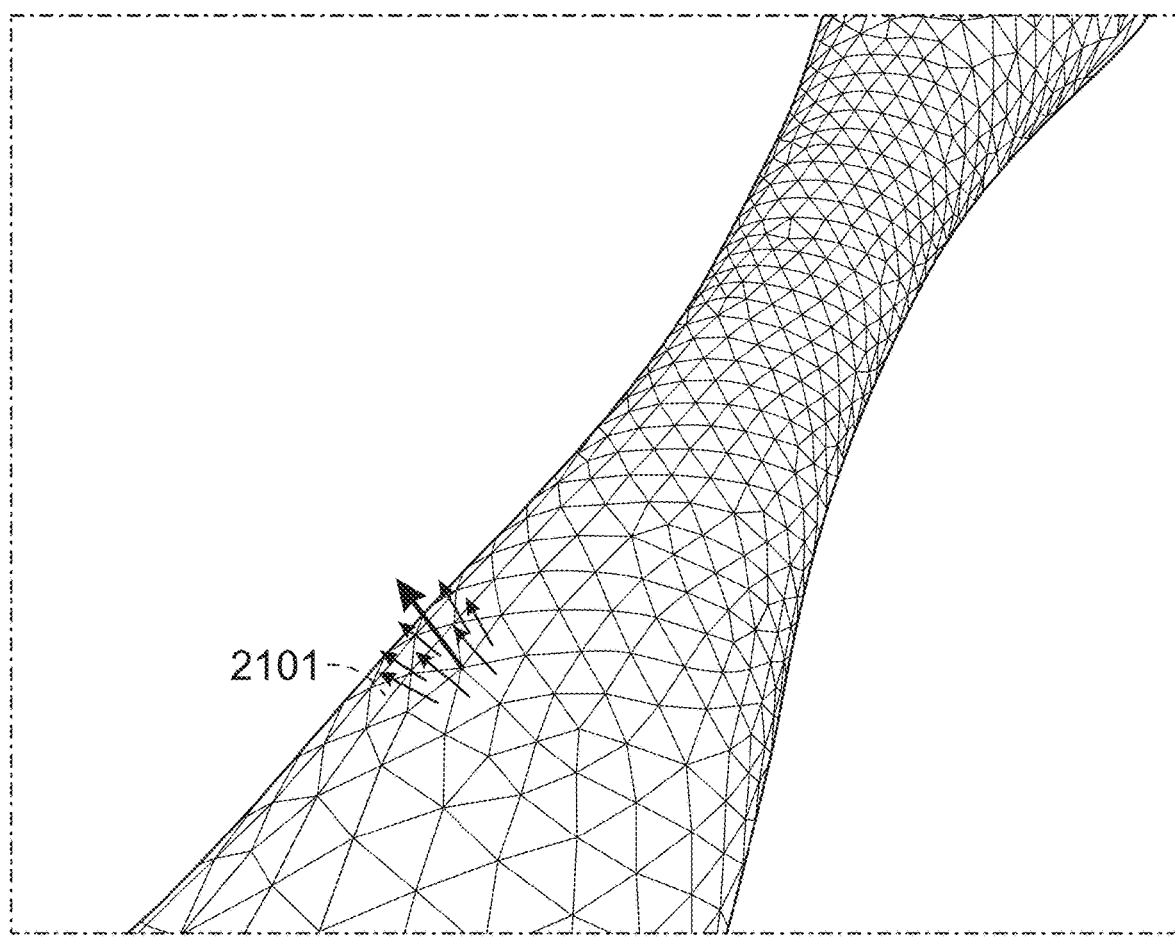
FIG. 21 shows an example of WSS vectors on the surface of the 3D volume mesh.
Figure 22:
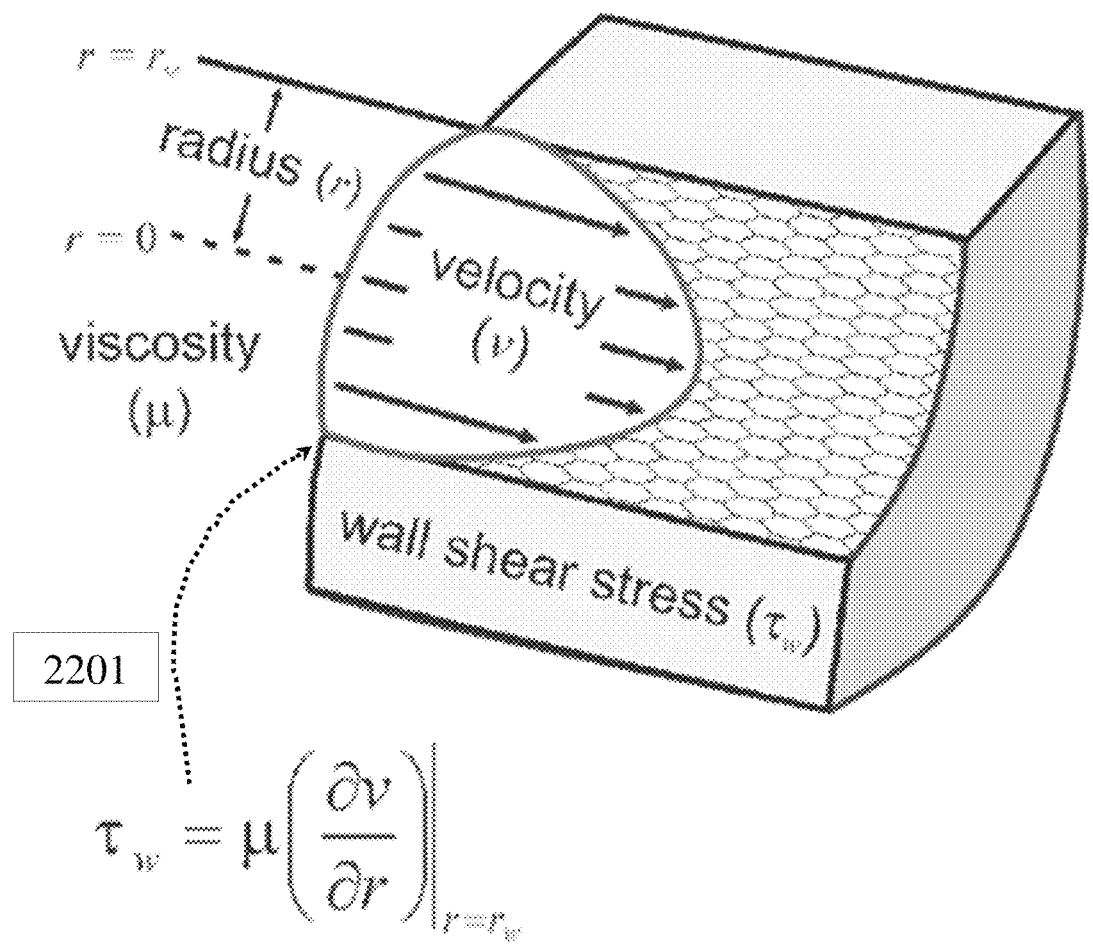
FIG. 22 shows an illustration of the method to calculate the WSS vector.

The WSS descriptor is calculated in part based on the boundary condition. For example, at 1204, the one or more processors compute the WSS from the velocity distribution throughout the 3D volume mesh as a result of step 1203. For example, the one or more processors calculate WSS vectors at the corresponding volumetric elements along the surface of the 3-D volume mesh. For each volumetric element on the surface of the 3D volume mesh the WSS is determined by the velocity distribution close to the vessel wall as illustrated by FIG. 21. Within FIG. 21, the green arrows (2101) represents the WSS vector of that particular volumetric element on the surface. To obtain these WSS vectors, the velocity gradient perpendicular to the vessel wall needs to be determined as illustrated at 2201 by FIG. 22. The velocity gradient close to the wall is called the wall shear rate, $\vec{\dot{\gamma}}$. To do so, the velocity gradient in all three orthogonal directions is determined, this results in the velocity gradient vector. The WSS vector is calculated by:

$$\vec{\tau}_w = -\mu \cdot \vec{\dot{\gamma}} \qquad \text{(equation 8)}$$

where μ is the viscosity of blood.

From the WSS vector, $\vec{\tau}_w$, the magnitude of the WSS is calculated by the length of the WSS vector, $|\vec{\tau}_q|$. Next to the WSS magnitude, more directional WSS can be derived based on the WSS vector. For example, the axial WSS can be derived, where the axial WSS ($WSS_{ax}$) represents the WSS in the axial direction of the vessel (1303, FIG. 13). The axial direction of the vessel is determined by the direction of the tangent to the vessel centerline. The circumferential or secondary WSS ($WSS_{sc}$) (1304), is the WSS in the direction perpendicular to the tangent of the vessel centerline. The radial wall shear stress ($WSS_{rad}$) is directed towards or away from the central axis of the vessel (1305).

At 1205, the one or more processors calculate a wall shear stress (WSS) descriptor, based on the 3D reconstruction, for a segment of a surface of the vessel that includes the lesion. The WSS descriptor includes information regarding an amount of variation in contraction or expansion applied at surface elements within the segment during at least a portion of a cardiac cycle. For example, the one or more processors may calculate the WSS descriptors based on the WSS vectors. For example, the WSS based parameters (WSS descriptors) are calculated by using the result of step 1204. When using a dynamic inlet blood velocity profile or inlet blood flow profile as illustrated by FIG. 18, the velocity or flow changes over time. The WSS can be calculated for every time point describe by the dynamic profile, each dot in the graph of FIG. 18, and generally covers the duration of one cardiac cycle. The WSS descriptors can be based on WSS information derived from multiple time moments or based on a single moment in time. WSS based descriptors obtained from one moment in time are for instance the peak WSS, the end systolic WSS or the end diastolic WSS.

WSS descriptors which incorporates WSS information from multiple time points, for instance a cardiac cycle, contain dynamic blood flow information and therefore contain more information on the dynamics due to the blood circulation.

Additionally or alternatively, the one or more processors are further configured to calculate the WSS vectors at corresponding surface elements within the segment; and to calculate the WSS descriptors based on the WSS vectors. Additionally or alternatively, the WSS descriptor includes a topological shear variation index (TSVI), the TSVI representing the amount of variation in contraction or expansion applied at the surface elements, where the one or more processors are further configured to calculate the TSVI based a divergence of the WSS vector. The TSVI may be based on instantaneous divergence at corresponding moments in the cardiac cycle and an average divergence over the cardiac cycle. Negative and positive values for the divergence are indicative of contraction and expansion, respectively, at the corresponding surface elements.

Additionally or alternatively, the one or more processors may be configured to calculate, as a WSS descriptor, for each of the surface elements, a time-averaged WSS (TAWSS) by averaging a magnitude of the WSS vector over the cardiac cycle. The TAWSS defines the average WSS along a cardiac cycle and is calculated by:

$$TAWSS = \frac{1}{T}\int_0^T |\vec{\tau}_w| dt \quad \text{(equation 9)}$$

where, T represents the duration of the cardiac cycle.

Additionally or alternatively, the one or more processors may be configured to calculate, as a WSS descriptor, the wall shear stress gradient, which is defined as the magnitude of the shear stress differential across the endothelial surface. This gradient can be calculated from the WSS or when considering a dynamic flow profile, from the TAWSS. Alternatively, this gradient can be computed in axial direction (1303), circumferential direction (1304) and radial direction (1305).

The Topological Shear Variation Index (TSVI) is another example of WSS based descriptor which includes temporal information. The TSVI as a measure of the variability of the local action of contraction/expansion exerted by the WSS along the cardiac cycle as described by Morbiducci et al., "*Wall shear stress topological skeleton independently predicts long-term restenosis after carotid bifurcation endarterectomy*", Annals of Biomedical Engineering 2020; 1-14 and by De Nisco et al., "*Deciphering ascending thoracic aortic aneurysm hemodynamics in relation to biomechanical properties*", Med Eng Phys. 2020; 82:119-29. Technically, the TSVI is defined as the root mean square deviation of the instantaneous divergence of the unit WSS vector field with respect to its average over the cardiac cycle. The TSVI is calculated in three steps. De first step determines the divergence of the normalized WSS vector field using the formula:

$$DIV_w = \nabla * (\tau_u) = \nabla * \left(\frac{\tau}{|\tau|}\right) \quad \text{(equation 10)}$$

with $\tau$ the WSS vector, $|\tau|$ the magnitude of the WSS vector, and $\tau_u$ the normalized WSS vector. Subsequently, the normalized WSS vector divergence, averaged over time, is calculated by the formula:

$$\overline{DIV_w} = \overline{\nabla * (\tau_u)} \quad \text{(equation 11)}$$

with the overbar denoting the quantity cycle-averaged. Finally, the TSVI is calculated by summing over the number of timesteps T using the formula:

$$TSVI = \left\{\frac{1}{T}\int_0^T [DIV_w - \overline{DIV_w}]^2 dt\right\}^{1/2} \quad \text{(equation 12)}$$

The amount of variation in the WSS contraction/expansion is characterized by a TSVI value for each surface point.

Additional WSS parameters can be calculated using the WSS values over a cardiac cycle. For example, the Oscillatory Shear Index (OSI), Cross Flow Index (CFI), Relative Residence Time (RRT), and the Transverse WSS (transWSS) can be calculated. The OSI represents the change of direction of the WSS vector from a predominant blood flow and therefore quantifies the alignment of the WSS vector with the TAWSS vector throughout the cardiac cycle and is calculated by:

$$OSI = \frac{1}{2}\left(1 - \frac{\left|\int_0^T \vec{\tau}_w dt\right|}{\int_0^T |\vec{\tau}_w| dt}\right) \quad \text{(equation 13)}$$

The CFI represents the directionally of WSS with no account taken of magnitude. Its is the sine of the angle between the temporal mean WSS vector and the instantaneous. The CFI is the time average of these instantaneous components and defined as:

$$CFI = \frac{1}{T}\int_0^T \left|\frac{WSS}{|WSS|} \cdot \left(n \times \frac{\int_0^T WSSdt}{|\int_0^T WSSdt|}\right)\right| dt \quad \text{(equation 14)}$$

The RRT is a marker of disturbed blood flow, marked by low magnitude and high oscillatory wall shear stress (WSS) and is calculated by:

$$RRT = \frac{1}{TAWSS \cdot (1 - 2 \cdot OSI)} = \frac{1}{\frac{1}{T}|\int_0^T WSSdt|} \quad \text{(equation 15)}$$

The transWSS is the average WSS components perpendicular to the temporal mean WSS vector over the cardiac cycle, with which endothelial cells are assumed to align. This provides the biological hypothesis that endothelial cells may be adversely affected by cross-flow. High transWSS may arise from large fluctuations of a small shear vector, small fluctuations of a large shear vector, or small fluctuations of a modest shear vector over a larger portion of the cardiac cycle. The transWSS is calculated by the formula:

$$transWSS = \frac{1}{T}\int_0^T \left|WSS \cdot \left(n \times \frac{\int_0^T WSSdt}{|\int_0^T WSSdt|}\right)\right| dt \quad \text{(equation 16)}$$

The presence of a lesion might result in a disturbance of the blood flow, the blood flow might become turbulent. Assessment of the hemodynamic changes due a lesion in the vessel can contribute in the determination of the lesion severity. The variations or fluctuations in the blood velocity distribution in the vessel can be assessed by the turbulent kinetic energy. The turbulent kinetic energy represents the velocity variation or fluctuations over time. To determine the turbulent kinetic energy, multiple cardiac cycles (e.g., 12 cycles) needs to be computed in CFD step 1203 and a turbulence model (e.g., RANS) should be present, to solve the turbulence of the blood flow correctly. Next, the velocity vector is decomposed by applying the Reynolds decomposition technique. The velocity component, u, is decomposed in the steady component, $\bar{u}$, and the fluctuating component, u'.

$$u' = \frac{1}{T}\int_0^T (u(t) - \bar{u})dt \qquad \text{(equation 17)}$$

And the turbulent kinetic energy is calculated by:

$$TKE = \frac{1}{2}\rho(u'^2 + v'^2 + w'^2) \qquad \text{(equation 18)}$$

Where u', v' and w' are the fluctuating velocity components of the velocity vector (x,y,z) per mesh node.

At 106, the one or more processors define a risk prediction. For example, the one or more processors calculate a myocardial infarction (MI) index (also referred to as a myocardial risk index) based on the WSS descriptor and the at least one of the pressure or anatomical parameters, the MI index representing a likelihood that the lesion will result in an MI. Additionally or alternatively, the one or more processors may be further configured to calculate the MI index by calculating a weighted sum of the WSS descriptor, the anatomical parameter and the pressure parameter. In accordance with embodiments herein, the MI index represents the likelihood that the lesion will rupture. The myocardium risk index of a coronary lesion is computed by a weighting of the anatomical parameters (step 103), pressure parameters (step 104) and the WSS based descriptors (step 105) within one or multiple segments.

The MI index may be presented/output in various manners. For example, the MI index may be presented as graphical and/or alphanumeric indicia indicative of a likelihood that a lesion will result in rupture or an MI. As one example, the MI index may present a percentage likelihood alone. As another example, the MI index may be presented as one or more colors along a color scale ranging from a first color indicative of a very low likelihood that a lesion will rupture and raging to a second color indicative of a very high likelihood that the lesion will rupture. As explained herein, the color indicia may be overlaid upon a graphical representation of a lesion with the different colors overlaid upon the lesion segment, upstream segment and downstream segment.

Figure 23:
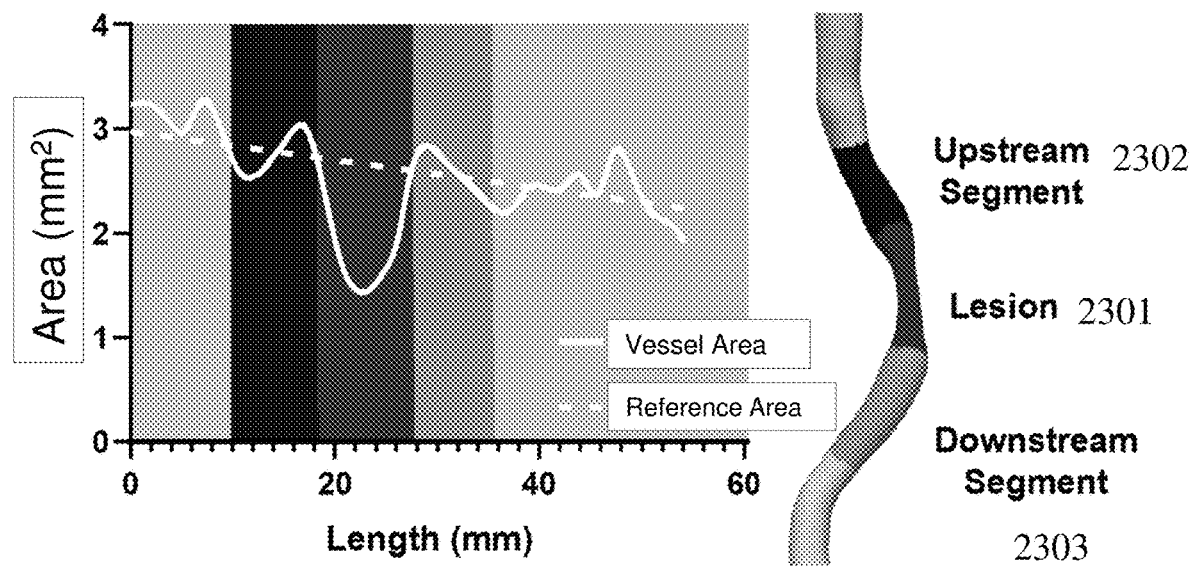
FIG. 23 shows an example of the segment definition from the vessel of interest.

The segments, in which the WSS based descriptors are extracted, are related to the lesion within the vessel of interest as illustrated by FIG. 23 shows an example of the segment definition from the vessel of interest, in which the lesion segment (2301) included the minimal lumen area (MLA) as defined by step 103, and is limited by the proximal and a distal boundary of the obstruction region as calculated within step 103. The one or more processors are further configured to: divide the vessel into a legion segment, an upstream segment (2302) and a downstream segment (2303). The lesion segment includes a region of the vessel having a minimum lumen area (MLA) and is delimited by proximal and distal boundaries. The upstream segment extends proximally from the proximal boundary by a proximal length that has a predetermined relation to a diameter of the vessel at the proximal boundary. The downstream segment extends distally from the distal boundary by a distal length that has a predetermined relation to a diameter of the vessel at the distal boundary. The upstream and downstream segments extended for instance three times the respective diameter at the obstruction boundary. The proximal boundary for the upstream segment and the distal boundary for the downstream segment.

The one or more processors calculate the average WSS based descriptor for each of the lesion segment, upstream segment and downstream segment. For instance, the TAWSS descriptor of the lesion segment is calculated by the mean of all TAWSS values within the lesion segment. Multiple WSS based segmental descriptors can be taken into consideration, of instance the maximum value of the specific WSS based descriptor within a segment, or the standard deviation of the WSS based descriptor values within a segment, the median value of the specific WSS based descriptor within a segment, or other statistical approaches.

Figure 24:
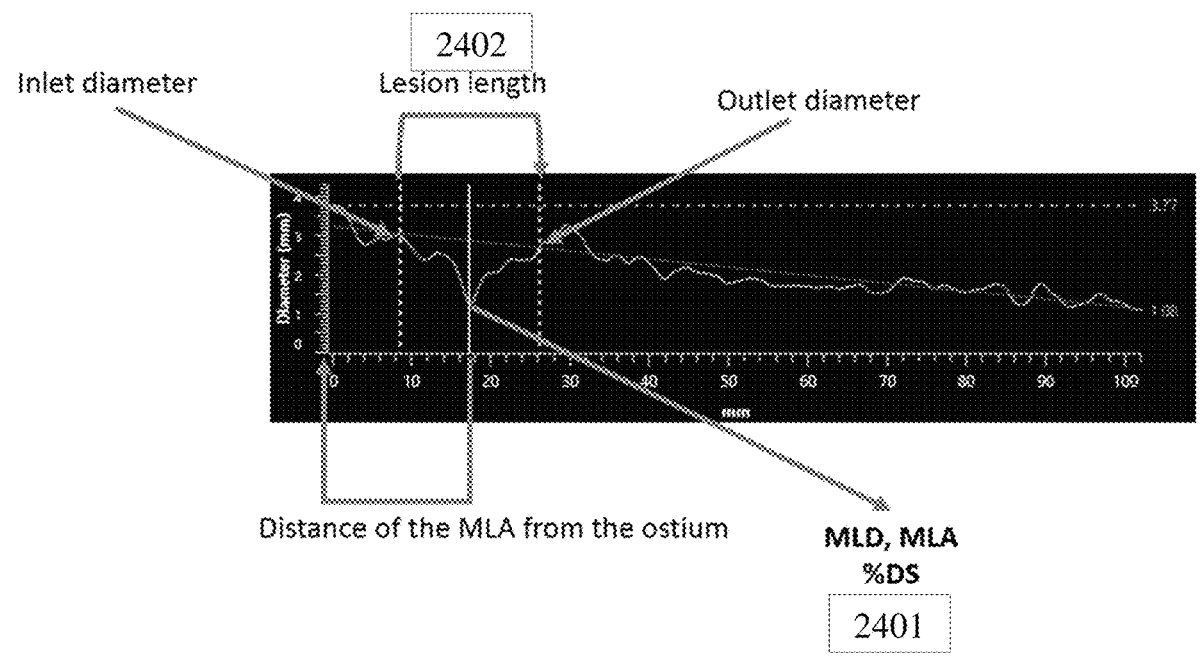
FIG. 24 shows an example of anatomical parameters.

FIG. 24 shows an example of anatomical parameters (result from step 103) which can be used during the calculation of the myocardium risk index. Similar to the segment definition for the WSS based descriptors, the lesion segment is an important parameter as identified by 2401 (MLA) and 2402 (obstruction region or lesion length). Besides these anatomical parameter, the % lesion severity, inlet and out diameter or area and distance from of MLA location can be used as anatomical parameters as illustrated by FIG. 24.

Figure 25:
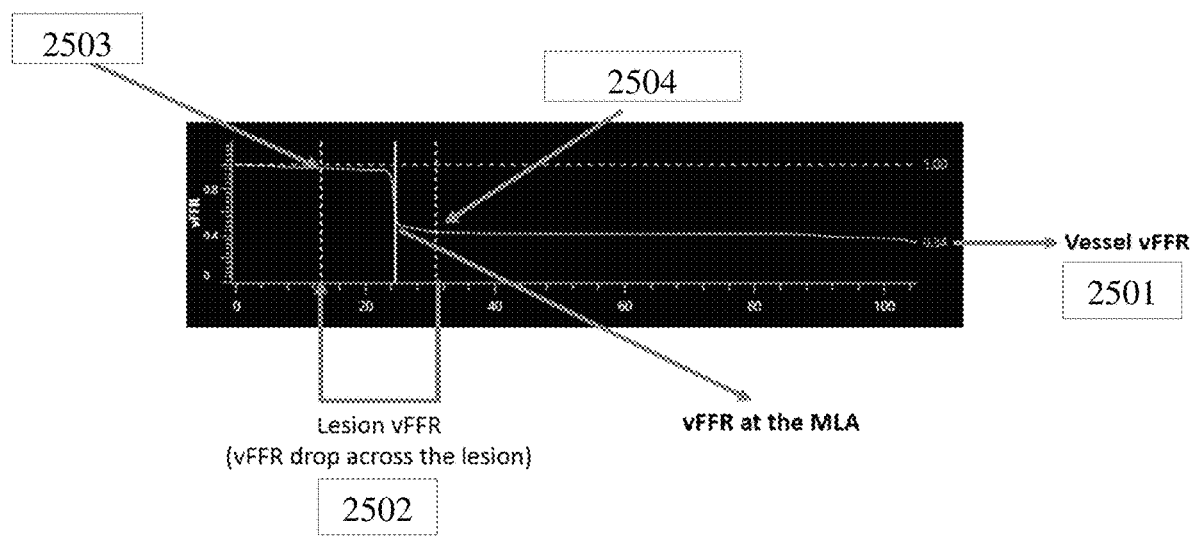
FIG. 25 shows an example of pressure parameters.

FIG. 25 shows an example of pressure parameters (result from step 104) which can be used during the calculation of the myocardium risk index. The vessel vFFR (2501) is an important pressure parameter and represent the vFFR value at the most distal location of the 3D reconstruction. Again, the obstruction region is used to extract additional pressure parameters as for instance the lesion vFFR (2502) also called 'translesional vFFR difference', which represents the vFFR difference between distal border (2504) and proximal border (2503) of the obstruction region. Beside vFFR values, also the pressure expressed in mmHg can be used for pressure parameters. Another example of a pressure parameter is the likelihood of focal or diffuse lesion based on the shape of the virtual pullback. This likelihood can for instance be based on the teachings as describe by Collet at al. in "*Measurement of Hyperemic Pullback Pressure Gradients to Characterize Patterns of Coronary Atherosclerosis*", J Am Coll Cardiology 2019 Oct. 8; 74 (14): 1772-1784. Furthermore, the pullback vFFR or pullback pressure curve along the vessel of interest (1104 within FIG. 11) can be used as an additional parameter.

Figure 26:
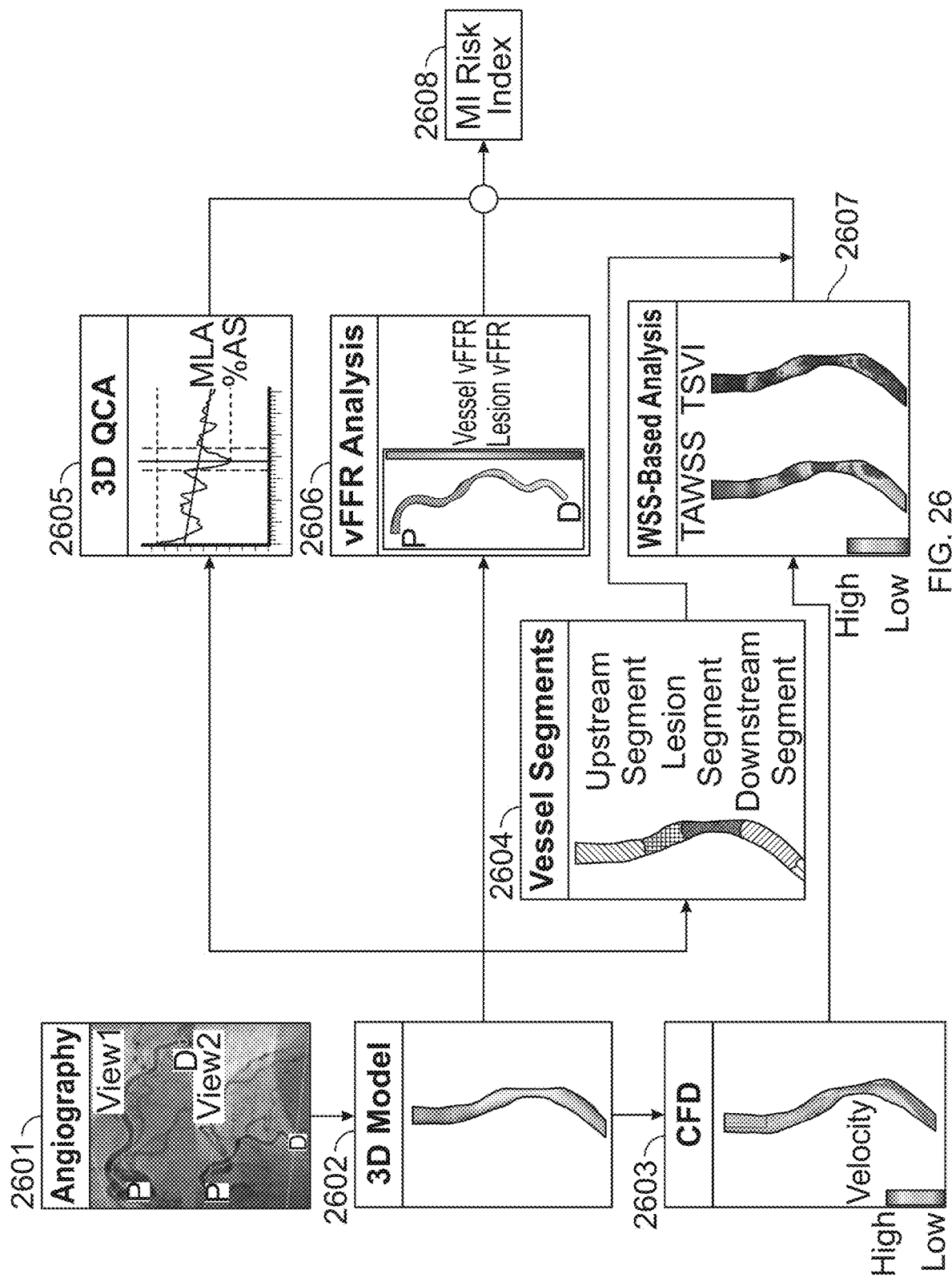
FIG. 26 shows a summary of the steps to calculate the myocardium risk index.

FIG. 26 shows a summary of the steps to calculate the myocardium risk index (MI risk index, 2608). First a 3D reconstruction of the vessel of interest is created (step 102) and illustrated by 2602 based on X-ray angiographic image data (step 101) as illustrated by 2601. Based on the 3D reconstruction the velocity is calculated (step 1203) by means of state of the art methods that solve the equations that describe the motion of fluids (Navier-Stokes equations), for instance by means of CFD, which is illustrated by 2603. The anatomical parameters extracted from the 3D reconstruction are presented by 2605, and the extracted pressure parameters from the 3D reconstruction are presented by 2606. The WSS based descriptors as illustrated by 2607 are computed within segments (2604). Finally, the MI risk index (2608) is a computed by a weighting the value of 2605, 2606 and 2607. The weighting can be performed equally for all the parameters or a more sophisticated methods can be applied to define the weighting parameters of the different parameters used to compute the MI risk index. For instance, by means of sensitively analysis as for instance taught by Saltelli, "*Making best use of model evaluations to compute sensitivity indices*", Comput. Phys. Commun., vol. 145, no.

2, pp. 280-297, 2002 or by Saltelli et al., "*Sensitivity analysis in practice. A guide to assessing scientific models*", 2004, ISBN 0-470-87093-1.

Sensitive analysis will provide extract a mathematical model that describes the complex relation between all the parameters involved as described before (input) in relationship with outcome, which will in our case MI or MACE. In this way, the model can be viewed as a black box, i.e. the output is an "opaque" function of its inputs. Quite often, some or all of the model inputs are subject to sources of uncertainty, including errors of measurement, absence of information and poor or partial understanding of the driving forces and mechanisms. This uncertainty imposes a limit on our confidence in the response or output of the model. Further, models may have to cope with the natural intrinsic variability of the system (aleatory), such as the occurrence of stochastic events. Good modeling practice requires that the modeler provide an evaluation of the confidence in the model. This requires, first, a quantification of the uncertainty in any model results (uncertainty analysis); and second, an evaluation of how much each input is contributing to the output uncertainty. Sensitivity analysis addresses how much each input is contributing to the output uncertainty, performing the role of ordering by importance the strength and relevance of the inputs in determining the variation in the output. This will optimize the weighing for each of the parameters to provide the MI risk index.

Figure 27:
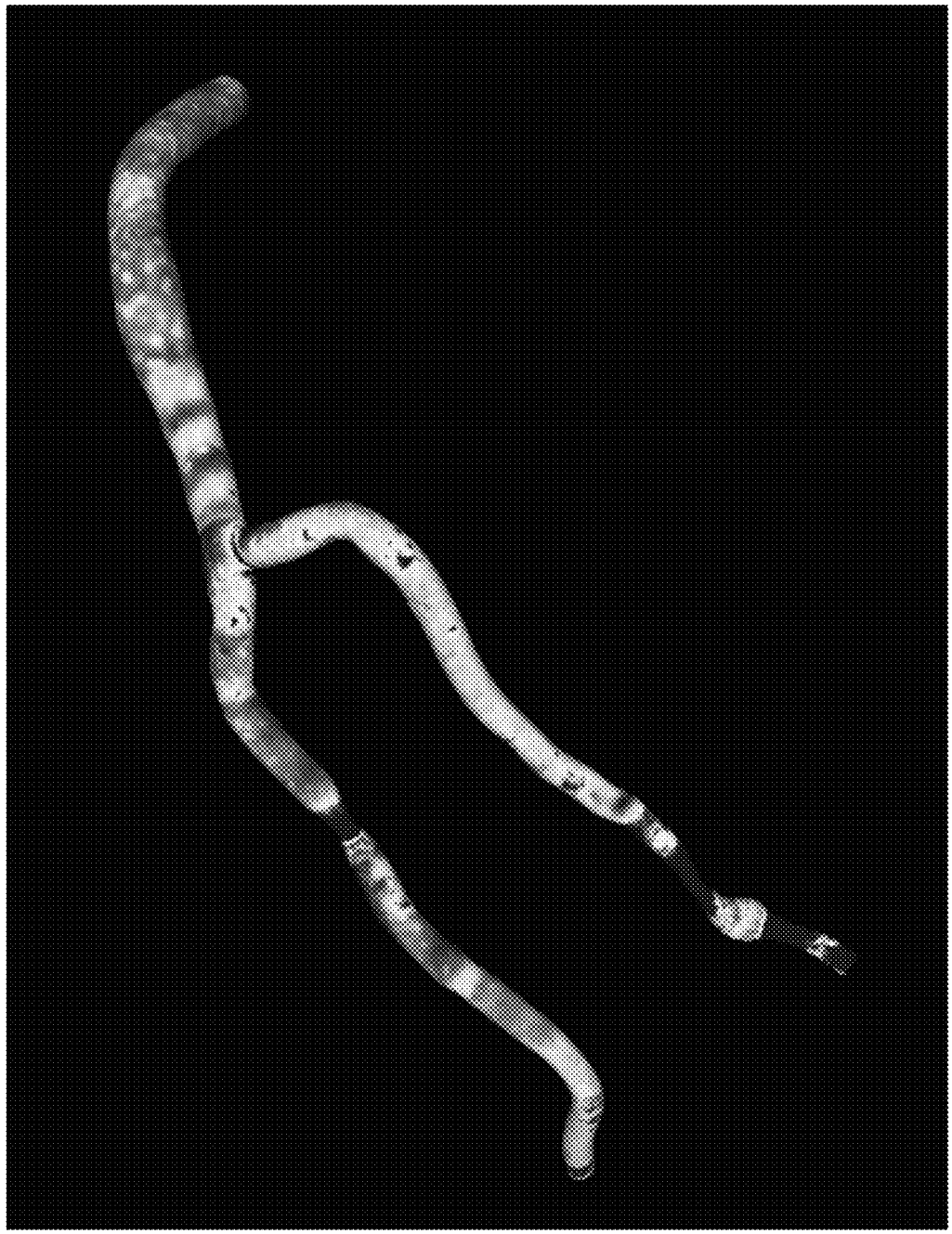
FIG. 27 shows an example of a coronary vessel in which the MI risk index is superimposed on the luminal surface as a color overlay.

The MI risk index can be reported in several ways. First, the MI risk index is presented as a single value within each segment; lesion segment, upstream segment and downstream segment as illustrated by FIG. 23. Second, the MI risk index is presented as a single value within a subdivision of the 3D reconstruction of an amount of segment with a predefined length. Third, the MI risk index is calculated for each surface element of the 3D volume mesh and presented as a color map superimposed on the 3D reconstruction as for instance illustrated by FIG. 27.

Figure 28:
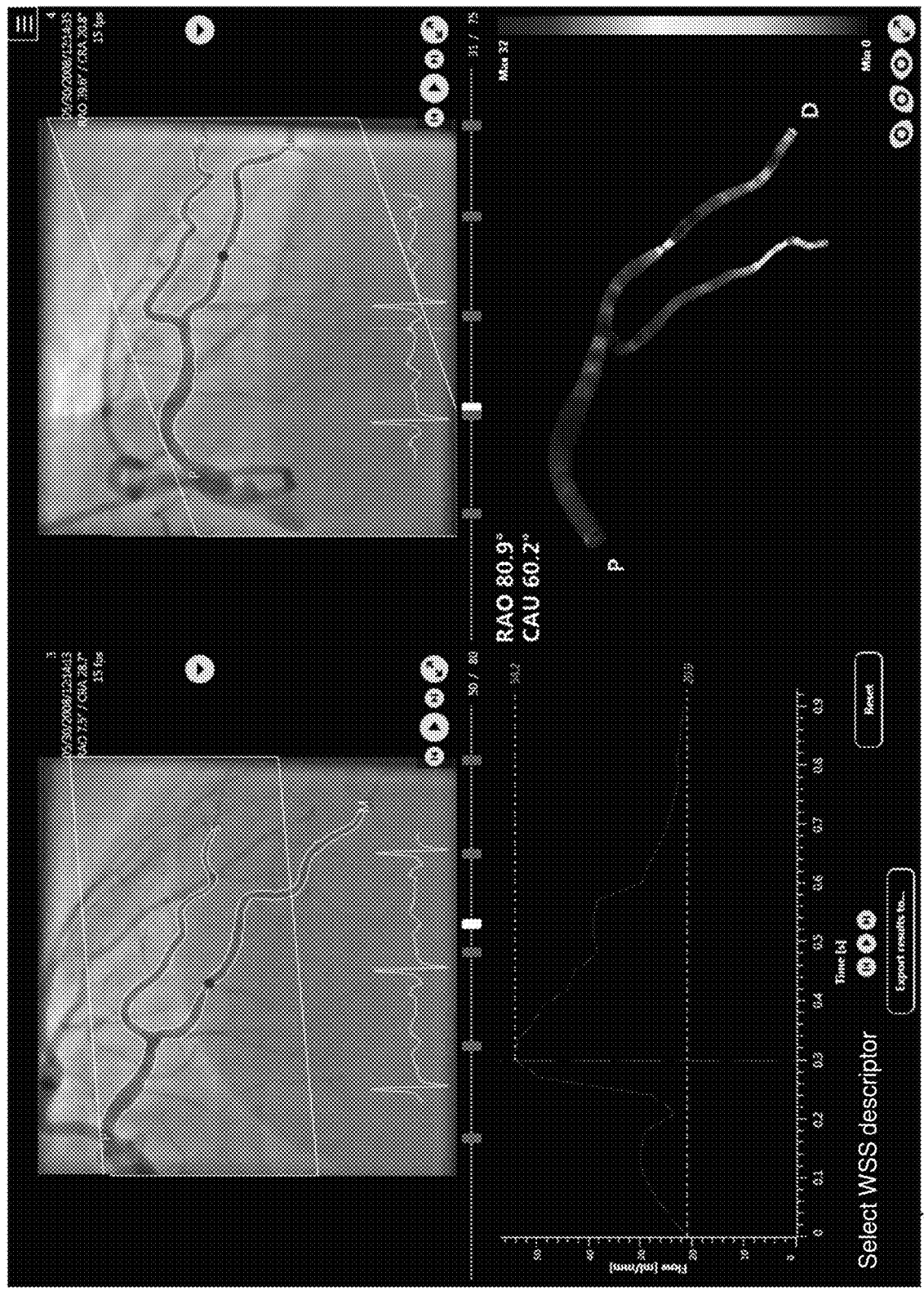
FIG. 28 shows an exemplary workflow screenshot that shows the WSS results as obtained from an analysis.
Figure 29:
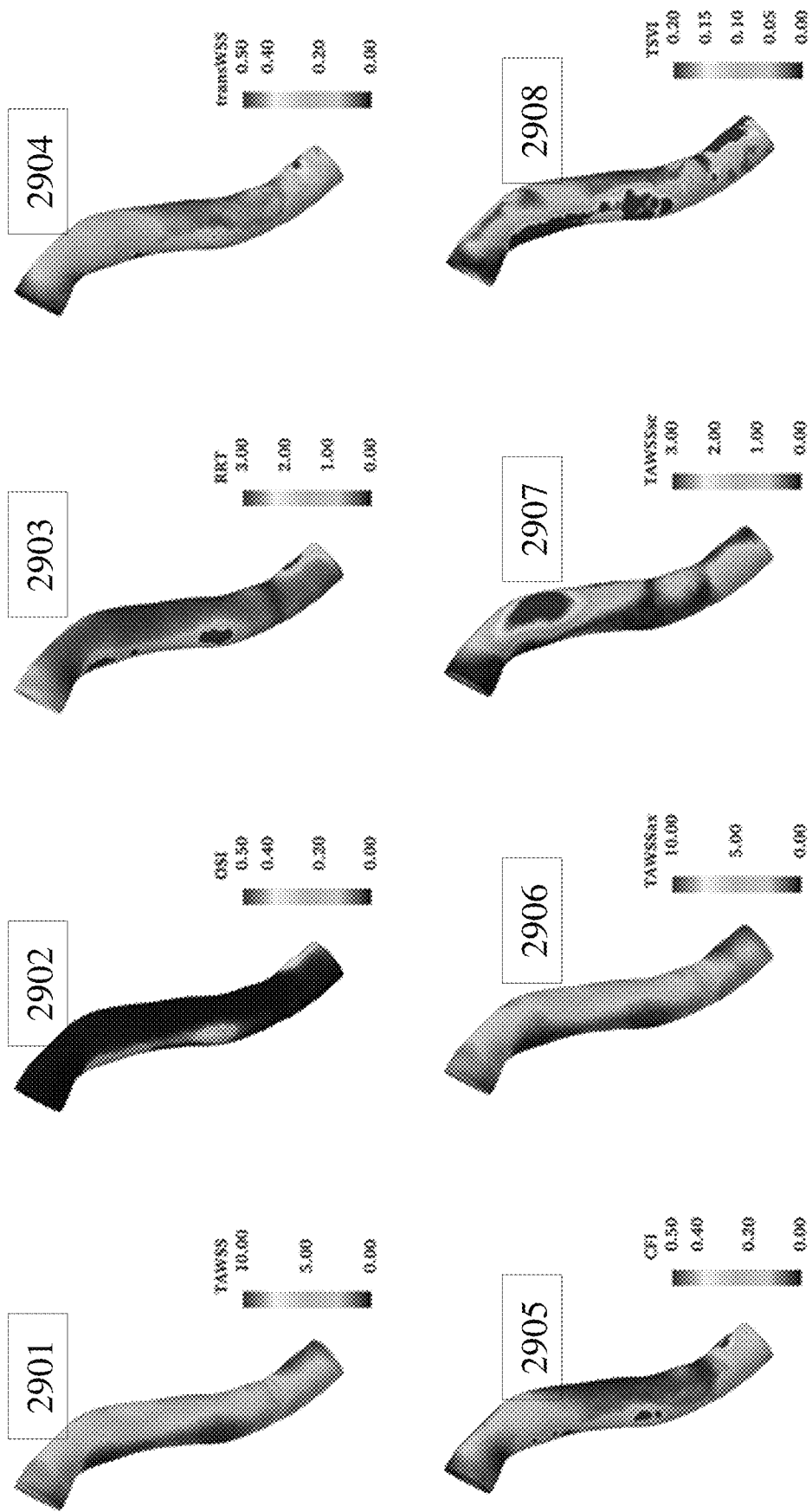
FIG. 29 provides some illustration of WSS descriptors superimposed on the 3D reconstruction as a color map.

Furthermore, the underlying WSS descriptors can be presented. FIG. 28 provides an example of a workflow screenshot that shows the WSS results as obtained from an analysis. In this example, the WSS is visualized as a color map superimposed on the 3D reconstruction corresponding to a single moment within the set of velocity profiles representing a cardiac cycle. Each WSS descriptor as described before can be visualized as a color map superimposed on the 3D reconstructions by for instance selecting one of described WSS descriptors through drop-box. FIG. 29 provides some illustration of WSS descriptors superimposed on the 3D reconstruction as a color map. FIG. 29 illustrates the differences in WSS descriptors as obtained from one analysis, meaning that the WSS vectors are identical for all the illustrated examples; TAWSS (2901), OSI (2902), RRT (2903), transWSS (2904), CFI (2905), TAWSSax (2906), TAWSSsc (2907), TSVI (2908).

Operations can be performed by processor unit on a standalone system, or a semi-standalone system which is connected to the X-ray system (FIG. 2*b*), or included directly in, for instance, an x-ray fluorographic system or any other image system to acquire two dimensional angiographic image sequences (FIG. 2*a*).

Figure 17:
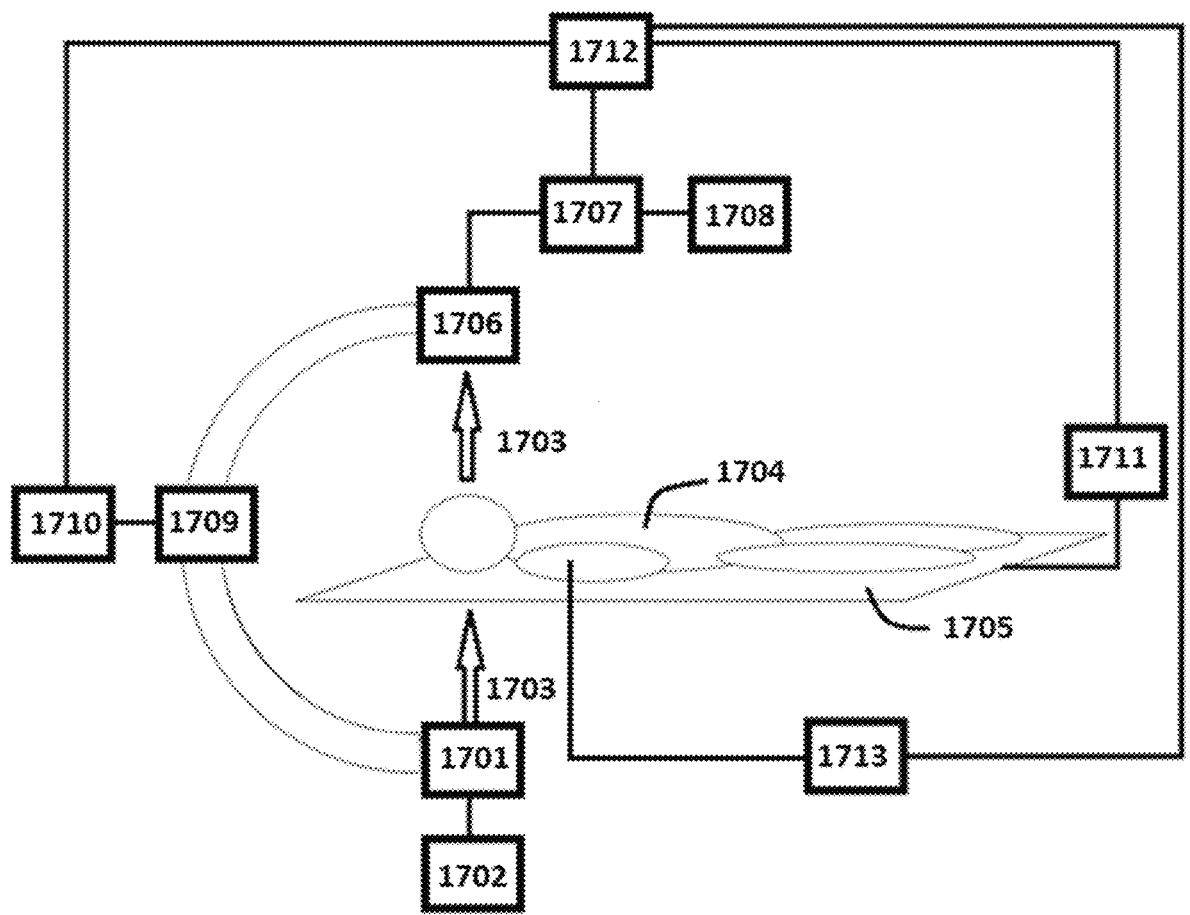
FIG. 17 shows an example of an x-ray cinefluorographic unit block diagram in accordance with an embodiment herein.

FIG. 17 illustrates an example of a high-level block diagram of an x-ray cinefluorograpic system. In this block diagram an example is shown on how embodiments could integrate in such a system.

The invention has been mainly disclosed with reference to coronary arteries. The skilled person would appreciate that this teaching can be equally extended to other vascular structures e.g., peripheral vessel or veins. Furthermore, the invention has been mainly disclosed with reference to X-ray angiographic image datasets. The skilled person would appreciate that this teaching can be equally extended to other imaging modalities, for instance rotational angiography, MRI, computed tomography (CT), SPECT, PET, Ultrasound, or the like.

Portions of the system (as defined by various functional blocks) may be implemented with dedicated hardware, analog and/or digital circuitry, and/or one or more processors operating program instructions stored in memory.

The X-ray system of FIG. 17 includes an X-ray tubes 1701 with a high voltage generator 1702 that generates an X-ray beam 1703. The high voltage generator 1702 controls and delivers power to the X-ray tube 1701. The high voltage generator 1702 applies a high voltage across the vacuum gap between the cathode and the rotating anode of the X-ray tube 1701. Due to the voltage applied to the X-ray tube 1701, electron transfer occurs from the cathode to the anode of the X-ray tube 1701 resulting in X-ray photon-generating effect also called Bremsstrahlung. The generated photons form an X-ray beam 1703 directed to the image detector 1706.

An X-ray beam 1703 comprises of photons with a spectrum of energies that range up to a maximum determined by among others the voltage and current submitted to the X-ray tube 1701. The X-ray beam 1703 then passes through the patient 1704 that lies on an adjustable table 1705. The X-ray photons of the X-ray beam 1703 penetrate the tissue of the patient to a varying degree. Different structures in the patient 1704 absorb different fractions of the radiation, modulating the beam intensity. The modulated X-ray beam 1703' that exits from the patient 1704 is detected by the image detector 1706 that is located opposite of the X-ray tube. This image detector 1706 can either be an indirect or a direct detection system.

In case of an indirect detection system, the image detector 1706 comprises of a vacuum tube (the X-ray image intensifier) that converts the X-ray exit beam 1703' into an amplified visible light image. This amplified visible light image is then transmitted to a visible light image receptor such as a digital video camera for image display and recording. This results in a digital image signal.

In case of a direct detection system, the image detector 1706 comprises of a flat panel detector. The flat panel detector directly converts the X-ray exit beam 1703' into a digital image signal. The digital image signal resulting from the image detector 1706 is passed through a digital image processing unit 1707. The digital image processing unit 1707 converts the digital image signal from 1706 into a corrected X-ray image (for instance inverted and/or contrast enhanced) in a standard image file format for instance DICOM. The corrected X-ray image can then be stored on a hard drive 1708.

Furthermore, the X-ray system of FIG. 17 comprises of a C-arm 1709. The C-arm holds the X-ray tube 1701 and the image detector 1706 in such a manner that the patient 1704 and the adjustable table 1705 lie between the X-ray tube 1701 and the image detector 1706. The C-arm can be moved (rotated and angulated) to a desired position to acquire a certain projection in a controlled manner using the C-arm control 1710. The C-arm control allows for manual or automatic input for adjustment of the C-arm in the desired position for the X-ray recording at a certain projection.

The X-ray system of FIG. 17 can either be a single plane or a bi-plane imaging system. In case of a bi-plane imaging system, multiple C-arms 1709 are present each consisting of an X-ray tube 1701, an image detector 1706 and a C-arm control 1710.

Additionally, the adjustable table 1705 can be moved using the table control 1711. The adjustable table 1705 can be moved along the x, y and z axis as well as tilted around a certain point.

Furthermore, a measuring unit 1713 is present in the X-ray system. This measuring unit contains information regarding the patient, for instance information regarding ECG, aortic pressure, biomarkers, and/or height, length etc.

A general unit 1712 is also present in the X-ray system. This general unit 1712 can be used to interact with the C-arm control 1710, the table control 1711, the digital image processing unit 1707, and the measuring unit 1713.

An embodiment is implemented by the X-ray system of FIG. 17 as follows. A clinician or other user acquires at least two X-ray angiographic image sequences of a patient 1704 by using the C-arm control 1710 to move the C-arm 1709 to a desired position relative to the patient 1704. The patient 1704 lies on the adjustable table 1705 that has been moved by the user to a certain position using the table control 1711. The X-ray image sequences are then generated using the high voltage generator 1702, the X-ray tube 1701, the image detector 1706 and the digital image processing unit 1707 as described above. These images are then stored on the hard drive 1708. Using these X-ray image sequences, the general processing unit 1712 performs the methods as described by present application, as for instance as described by FIG. 1 using the information of the measuring unit 1713, the digital image processing unit 1707, C-arm control unit 1710 and the table control unit 1711.

There have been described and illustrated herein several embodiments of a method and apparatus for restoring missing information regarding the order and the flow direction of the velocity components. While particular embodiments of the invention have been described, it is not intended that the invention be limited thereto, as it is intended that the invention be as broad in scope as the art will allow and that the specification be read likewise. For example, the data processing operations can be performed offline on images stored in digital storage, such as a PACS commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

In the event that an appendix is attached hereto, the content of the appendix shall be treated as a portion of the present specification, and is incorporated herein by reference in its entirety.

All references, including publications, patent applications and patents, cited herein are hereby incorporated by reference to the same extent as if each reference were individually and specifically indicated to be incorporated by reference and were set forth in its entirety herein.

What is claimed is:

1. A computer-implemented method, comprising:
utilizing one or more computers configured to execute specific program instructions for,
retrieving patient specific image data;
creating a 3D reconstruction of a vessel of interest from the patient specific image data, wherein the vessel of interest represents a subset of a coronary tree that includes a lesion;
determining boundary conditions that include inlet conditions that represent a set of velocity profiles, at a proximal side of the 3D reconstruction, over the multiple moments in time along at least the portion of the cardiac cycle;
calculating at least one of pressure parameters or anatomical parameters based at least in part on a portion of the 3D reconstruction that includes the lesion and the set of velocity profiles;
calculating a wall shear stress (WSS) vectors, based on the 3D reconstruction, at corresponding surface elements for a segment of a surface of the vessel that includes the lesion;
calculating a WSS descriptor based on a divergence of the WSS vectors, the WSS descriptor including a topological shear variation index (TSVI) representing an amount of variation in contraction or expansion applied at surface elements within the segment during at least a portion of a cardiac cycle; and
calculating a myocardial infarction (MI) index based on the WSS descriptor and the at least one of the pressure or anatomical parameters, the MI index representing a likelihood that the lesion will result in an MI.

2. The method of claim 1, wherein a first velocity profile, from the set of velocity provides, represents a velocity profile across a cross section of the vessel at a proximal side of the 3D reconstruction at a corresponding momentum in time along the cardiac cycle.

3. The method of claim 1, wherein the TSVI is based on instantaneous divergence at corresponding moments in the cardiac cycle and an average divergence over the cardiac cycle.

4. The method of claim 3, wherein negative and positive values for the divergence are indicative of contraction and expansion, respectively, at the corresponding surface elements.

5. The method of claim 1, further comprising, for each of the surface elements, calculating a time-averaged WSS (TAWSS) by averaging a magnitude of the WSS vector over the corresponding moments in time along the cardiac cycle.

6. The method of claim 1, wherein the calculating the MI index includes calculating a weighted sum of the WSS descriptor, the anatomical parameter and the pressure parameter.

7. The method of claim 1, further comprising dividing the vessel into a legion segment, an upstream segment and a downstream segment, the lesion segment including a region of the vessel having a minimum lumen area (MLA) and delimited by proximal and distal boundaries, the upstream segment extending proximally from the proximal boundary by a proximal length that has a predetermined relation to a diameter of the vessel at the proximal boundary, the downstream segment extending distally from the distal boundary by a distal length that has a predetermined relation to a diameter of the vessel at the distal boundary.

8. The method of claim 1, wherein the WSS vector includes an axial component and a circumferential component.

9. The method of claim 1, wherein the MI index represents the likelihood that the lesion will rupture.

10. The method of claim 1, wherein the calculating the WSS descriptor further comprises:
- converting 3D reconstruction into a 3D volume mesh;
- utilizing computational fluid dynamics (CFD), to obtain velocities at volumetric elements throughout the 3D volume mesh, based on boundary conditions for the moments in time along at least the portion of the cardiac cycle;
- calculating the WSS vectors at the corresponding volumetric elements along the surface of the 3D volume mesh; and
- calculating the WSS descriptors based on the WSS vectors.

11. The method of claim 1, wherein the vessel of interest represents one of a single vessel, bifurcation, a branching vessel or vessel tree.

12. The method of claim 1, wherein the coronary tree includes a branching vessel that is not included in the 3D reconstruction, the method further comprising:
- identifying a branching vessel from the patient specific image data;
- projecting the branching vessel onto the 3D reconstruction of the vessel of interest;
- calculating a first flow within the vessel of interest proximal to the branching vessel;
- calculating a second flow within the vessel of interest distal to the branching vessel;
- assigning a difference between the first and second flow to the branching vessel; and
- assigning the boundary condition to the surface of the vessel of interest based on the difference, wherein the WSS descriptor is calculated in part based on the boundary condition.

13. A system, comprising:
- memory to store program instructions;
- a processor that, when executing the program instructions, is configured to:
  - retrieve patient specific image data;
  - create a 3D reconstruction of a vessel of interest from the patient specific image data, wherein the vessel of interest represents a subset of a coronary tree that includes a lesion;
  - determine boundary conditions that include inlet conditions that represent a set of velocity profiles, at a proximal side of the 3D reconstruction, over the multiple moments in time along at least the portion of the cardiac cycle;
  - calculate at least one of pressure parameters or anatomical parameters based at least in part on a portion of the 3D reconstruction that includes the lesion;
  - calculate a wall shear stress (WSS)) vectors, based on the 3D reconstruction, at corresponding surface elements for a segment of a surface of the vessel that includes the lesion,
  - calculate a WSS descriptor based on a divergence of the WSS vectors, the WSS descriptor including a topological shear variation index (TSVI) representing an amount of variation in contraction or expansion applied at surface elements within the segment during at least a portion of a cardiac cycle; and
  - calculate a myocardial infarction (MI) index based on the WSS descriptor and the at least one of the pressure or anatomical parameters, the MI index representing a likelihood that the lesion will result in an MI.

14. The system of claim 13, wherein a first velocity profile, from the set of velocity provides, represents a velocity profile across a cross section of the vessel at a proximal side of the 3D reconstruction at a corresponding momentum in time along the cardiac cycle.

15. The system of claim 13, wherein the TSVI is based on instantaneous divergence at corresponding moments in the cardiac cycle and an average divergence over the cardiac cycle.

16. The system of claim 15, wherein negative and positive values for the divergence are indicative of contraction and expansion, respectively, at the corresponding surface elements.

17. The system of claim 13, wherein the processor is further configured to calculate, for each of the surface elements, a time-averaged WSS (TAWSS) by averaging a magnitude of the WSS vector over the corresponding moments in time along the cardiac cycle.

18. The system of claim 13, wherein the processor is further configured to calculate the MI index by calculating a weighted sum of the WSS descriptor, the anatomical parameter and the pressure parameter.

19. The system of claim 13, wherein the processor is further configured to: divide the vessel into a legion segment, an upstream segment and a downstream segment, the lesion segment including a region of the vessel having a minimum lumen area (MLA) and delimited by proximal and distal boundaries, the upstream segment extending proximally from the proximal boundary by a proximal length that has a predetermined relation to a diameter of the vessel at the proximal boundary, the downstream segment extending distally from the distal boundary by a distal length that has a predetermined relation to a diameter of the vessel at the distal boundary.

20. The system of claim 13, wherein the MI index represents the likelihood that the lesion will rupture.

21. The system of claim 13, wherein the processor is further configured to calculate the WSS descriptor by:
- converting the 3D reconstruction into a 3D volume mesh;
- utilizing computational fluid dynamics (CFD), to obtain velocities at volumetric elements throughout the 3D volume mesh, based on boundary conditions for the moments in time along at least the portion of the cardiac cycle;
- calculating the WSS vectors at the corresponding volumetric elements along the surface of the 3D volume mesh; and
- calculating the WSS descriptors based on the WSS vectors.

22. The system of claim 13, wherein the vessel of interest represents one of a single vessel, bifurcation, a branching vessel or vessel tree.

23. The system of claim 13, wherein the coronary tree includes a branching vessel that is not included in the 3D reconstruction, wherein the processor is further configured to
- Identify a branching vessel from the patient specific image data;
- project the branching vessel onto the 3D reconstruction of the vessel of interest;
- calculate a first flow within the vessel of interest proximal to the branching vessel;
- calculate a second flow within the vessel of interest distal to the branching vessel;
- assign a difference between the first and second flow to the branching vessel; and assign the boundary condition to the surface of the vessel of interest based on the difference, wherein the WSS descriptor is calculated in part based on the boundary condition.

24. The method of claim 1, further comprising repeating the 3D reconstruction for multiple moments in time along at least a portion of a cardiac cycle to form a 3D+t reconstruction, the at least one of pressure parameters or anatomical parameters calculated based at least in part on a portion of the 3D+t reconstruction.

25. The system of claim 13, wherein the processor is further configured to repeat the 3D reconstruction for multiple moments in time along at least a portion of a cardiac cycle to form a 3D+t reconstruction, the at least one of pressure parameters or anatomical parameters calculated based at least in part on a portion of the 3D+t reconstruction.

* * * * *